(12) United States Patent
Diaz et al.

(10) Patent No.: US 11,844,931 B2
(45) Date of Patent: Dec. 19, 2023

(54) SYSTEM AND METHOD FOR SAFETY SYRINGE

(71) Applicant: CREDENCE MEDSYSTEMS, INC., Menlo Park, CA (US)

(72) Inventors: Stephen H. Diaz, Palo Alto, CA (US); Jeff Tillack, Foster City, CA (US); Alan E. Shluzas, San Carlos, CA (US); John F. Shanley, Emerald Hills, CA (US); Dan Thayer, Tustin, CA (US); Gary Steese-Bradley, San Jose, CA (US); John Merhige, Menlo Park, CA (US)

(73) Assignee: Credence MedSystems, Menlo Park, CA (US)

( * ) Notice: Subject to any disclaimer, the term of this patent is extended or adjusted under 35 U.S.C. 154(b) by 57 days.

(21) Appl. No.: 17/472,886

(22) Filed: Sep. 13, 2021

(65) Prior Publication Data

US 2022/0062554 A1    Mar. 3, 2022

Related U.S. Application Data

(63) Continuation of application No. 16/435,429, filed on Jun. 7, 2019, now Pat. No. 11,116,905.

(Continued)

(51) Int. Cl.
*A61M 5/19* (2006.01)
*A61M 5/31* (2006.01)
(Continued)

(52) U.S. Cl.
CPC ............ *A61M 5/19* (2013.01); *A61M 5/3129* (2013.01); *A61M 5/31511* (2013.01); *A61M 2005/1787* (2013.01); *A61M 2005/31598* (2013.01)

(58) Field of Classification Search
CPC .. A61M 5/19; A61M 5/3129; A61M 5/31511; A61M 2005/1787;
(Continued)

(56) References Cited

U.S. PATENT DOCUMENTS 2,653,607 A    9/1950 Deans
3,896,805 A *  7/1975 Weingarten ............. A61M 5/32
                                                            604/203
(Continued)

FOREIGN PATENT DOCUMENTS

JP              S64951 U       1/1989
WO      WO 2017/008850         1/2017
WO      WO 2018/085458 A1      5/2018

OTHER PUBLICATIONS

Non-Final Office Action for U.S. Appl. No. 16/435,429 dated Jan. 28, 2021.
(Continued)

*Primary Examiner* — James D Ponton
*Assistant Examiner* — Neeraja Gollamudi
(74) *Attorney, Agent, or Firm* — Vista IP Law Group LLP

(57) ABSTRACT

A system for serially injecting liquids includes a syringe body, proximal and distal stopper members disposed in the syringe body, a first liquid in a distal chamber, a second liquid in a proximal chamber, a plunger member, and a needle hub assembly coupled to a distal needle interface of the syringe body. The plunger member includes a needle retention feature disposed in a plunger interior, an energy-storage member disposed in the plunger interior, and an energy-storage member latching member disposed in the plunger interior. The needle assembly includes a needle having a needle proximal end feature, a hub, and a needle latching member configured to couple the needle to the hub. Manipulating the plunger member to insert the proximal stopper member distally relative to the syringe body initially (Continued)

expels the first liquid, then the second liquid. The needle is at least partially retractable into plunger interior.

26 Claims, 62 Drawing Sheets

Related U.S. Application Data

(60) Provisional application No. 62/729,880, filed on Sep. 11, 2018, provisional application No. 62/682,381, filed on Jun. 8, 2018.

(51) Int. Cl.
*A61M 5/315* (2006.01)
*A61M 5/178* (2006.01)

(58) Field of Classification Search
CPC ...... A61M 2005/31598; A61M 5/3291; A61M 5/3297; A61M 2005/287; A61M 2005/323; A61M 5/3221; A61M 5/3294; A61M 5/322
See application file for complete search history.

(56) References Cited

U.S. PATENT DOCUMENTS

| | | | |
|---|---|---|---|
| 4,413,991 A * | 11/1983 | Schmitz | A61M 5/2066 604/191 |
| 6,010,486 A | 1/2000 | Carter et al. | |
| 6,997,910 B2 | 2/2006 | Howlett et al. | |
| 2003/0004468 A1 | 1/2003 | Righi et al. | |
| 2004/0171984 A1* | 9/2004 | Greenfield | A61M 5/286 604/82 |
| 2013/0035664 A1 | 2/2013 | Mojdehbakhsh et al. | |
| 2014/0358091 A1 | 12/2014 | Johannesson et al. | |
| 2015/0148748 A1 | 5/2015 | Shluzas et al. | |
| 2016/0206834 A1* | 7/2016 | Shluzas | A61M 5/3276 |
| 2018/0117261 A1 | 5/2018 | Steese-Bradley et al. | |

OTHER PUBLICATIONS

Amendment Response to NFOA for U.S. Appl. No. 16/435,429 dated Apr. 28, 2021.
Notice of Allowance for U.S. Appl. No. 16/435,429 dated May 12, 2021.
PCT International Search Report and Written Opinion for International Appln. No. PCT/US2019/036176, Applicant Credence Medsystems, Inc., dated Aug. 22, 2019 (15 pages).
Non-Final Office Action for U.S. Appl. No. U.S. Appl. No. 16/234,054 dated Jun. 29, 2020.
Amendment Response for U.S. Appl. No. 16/234,054 dated Sep. 28, 2020.
Notice of Allowance for U.S. Appl. No. 16/234,054 dated Oct. 16, 2020.
Foreign OA for JP Patent Appln. No. 2020-568271 dated Jul. 5, 2022 (with English translation).
Foreign OA Response for JP Patent Appln. No. 2020-568271 dated Dec. 2, 2022.
Foreign FOA for JP Patent Appln. No. 2020-568271 dated Dec. 15, 2022 (with English translation).
Foreign FOA Response for JP Patent Appln. No. 2020-568271 dated May 22, 2023.
Foreign OA for CN Patent Appln. No. 201980051544.1 dated Dec. 24, 2021.
Foreign OA Response for CN Patent Appln. No. 201980051544.1 dated May 7, 2022.
Foreign NOA for CN Patent Appln. No. 201980051544.1 dated Sep. 15, 2022.
Foreign Exam Report for EP Patent Appln. No. 19733357.8 dated Apr. 8, 18, 2023.
Foreign Exam Report for IN Patent Appln. No. 202047057519 dated Sep. 15, 2022.
Foreign OA Response for IN Patent Appln. No. 202047057519 dated Mar. 14, 2023.
Foreign OA for JP Patent Appln. No. 2020-568271 dated Aug. 16, 2023 (with English translation).
Foreign Exam Report Response for EP Patent Appln. No. 19733357.8 dated Aug. 28, 2023.

* cited by examiner

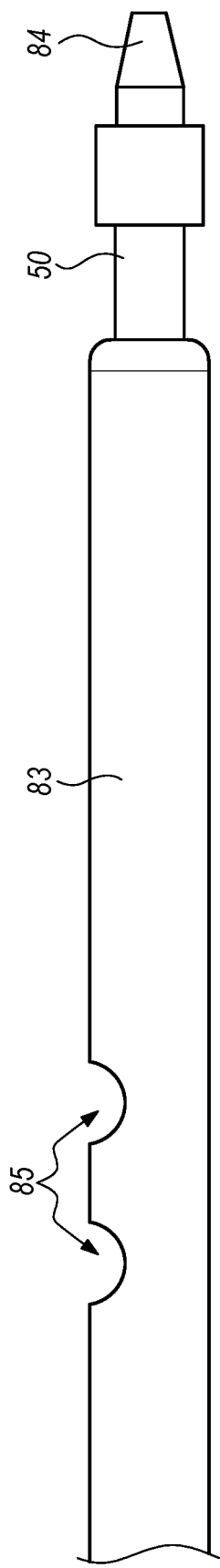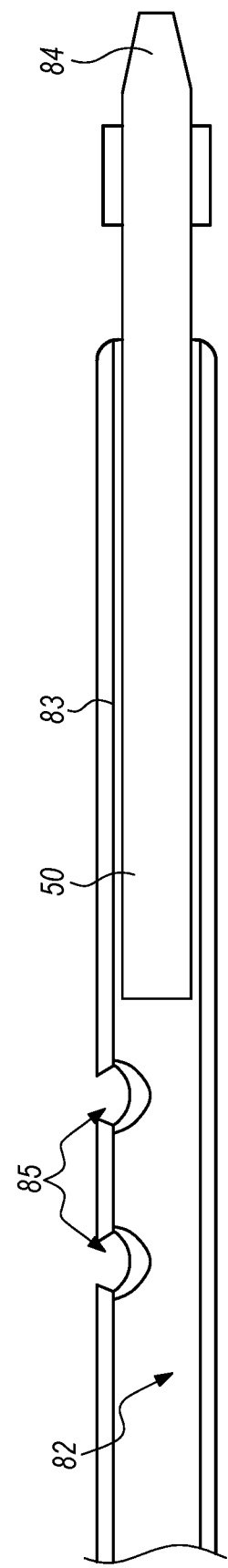

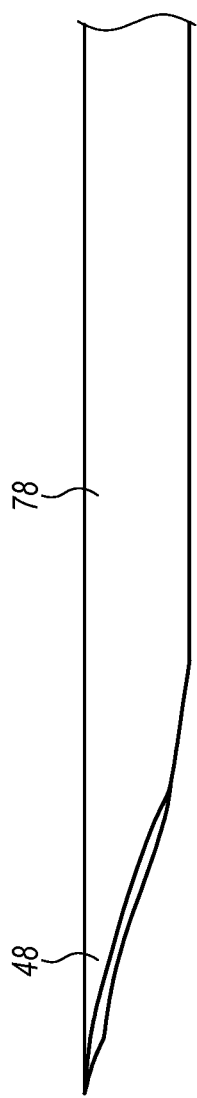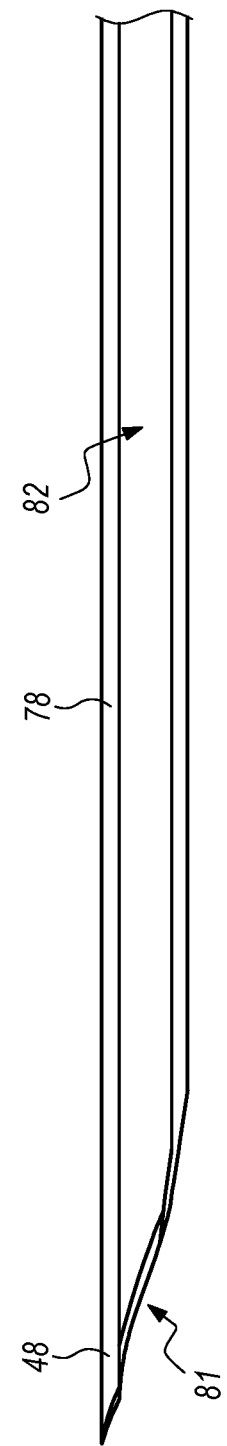

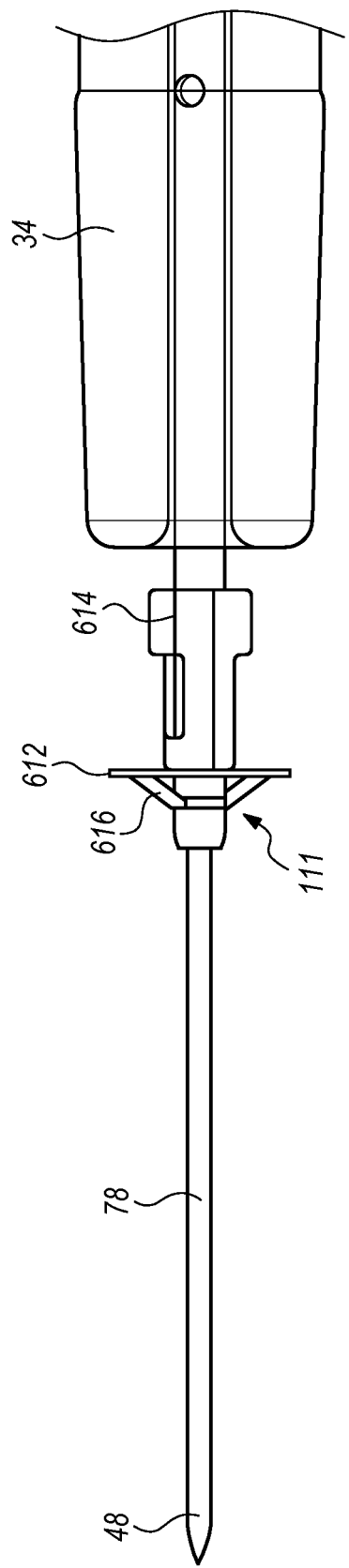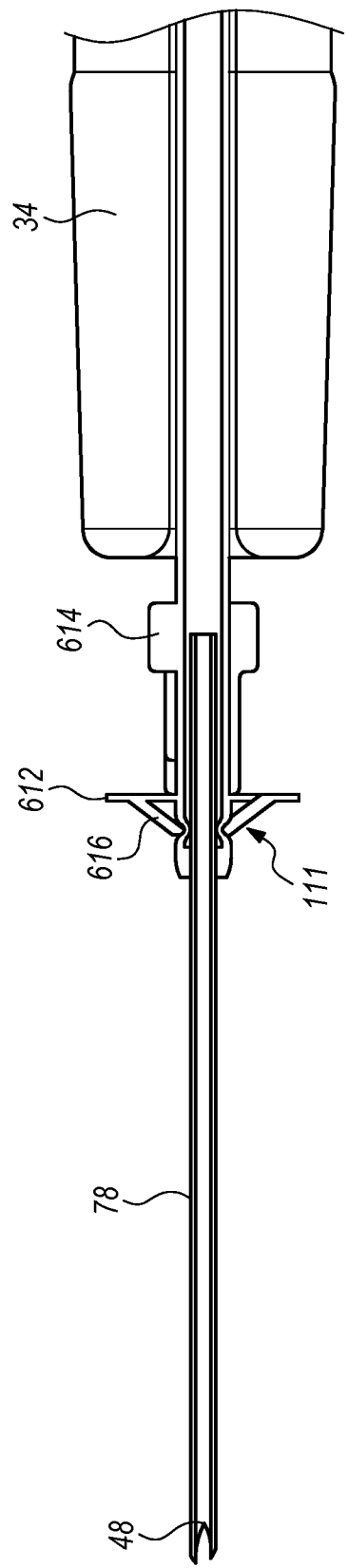

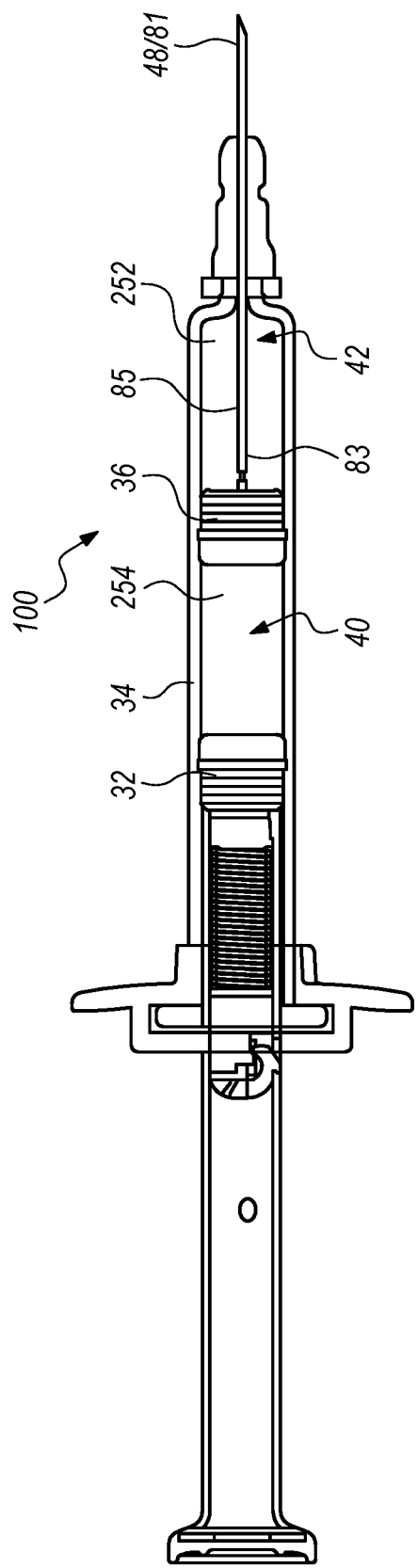
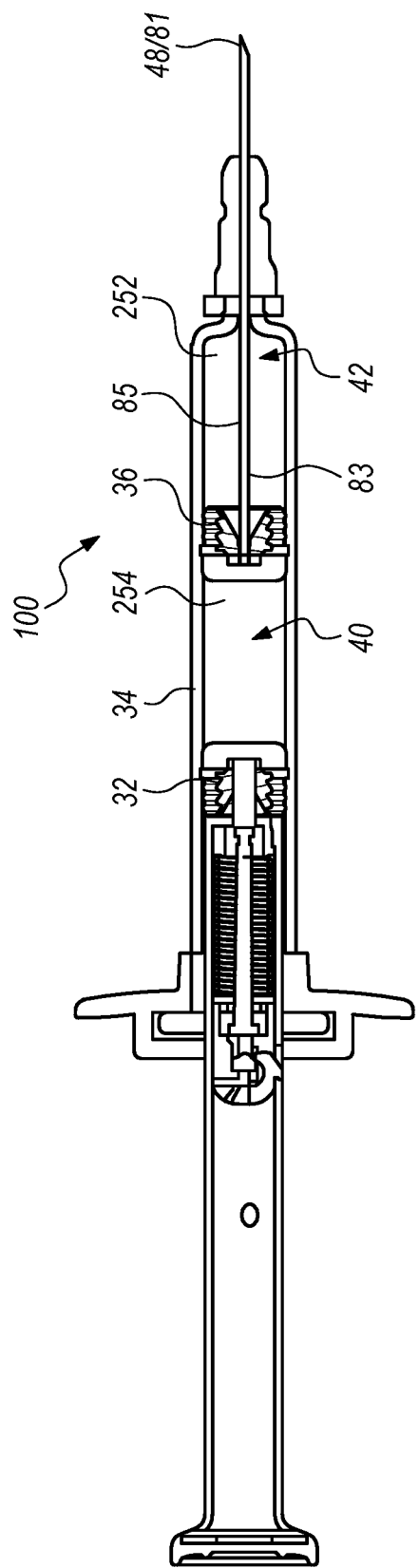

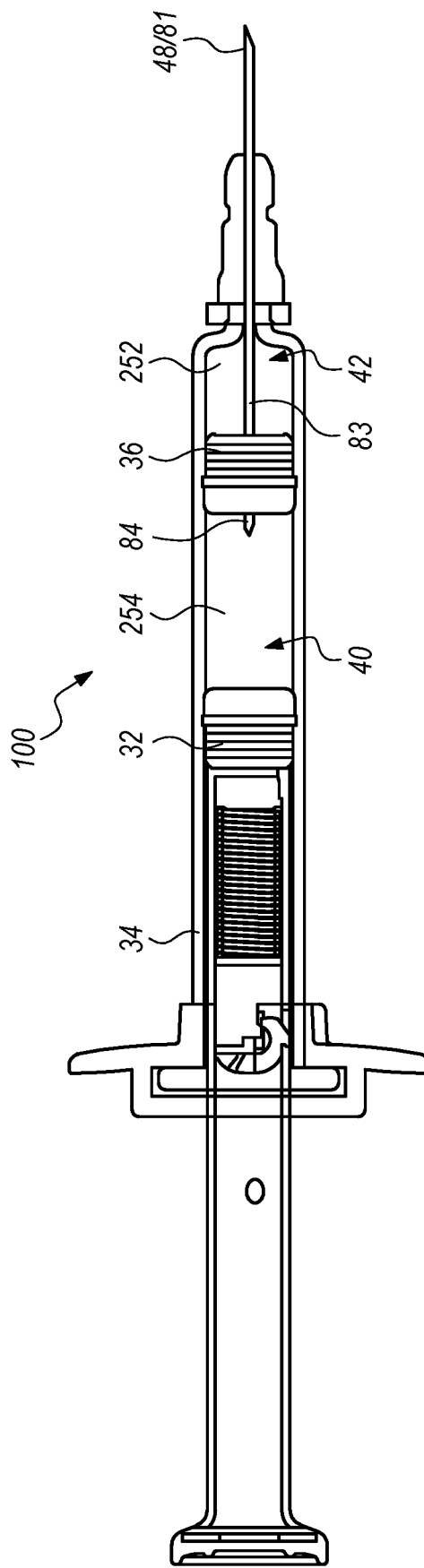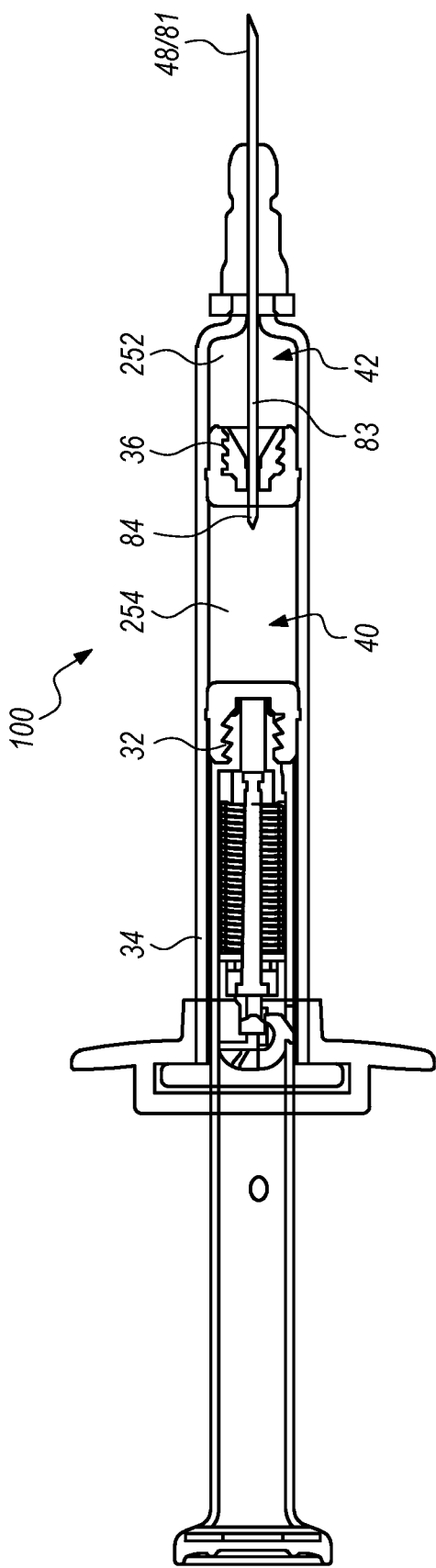

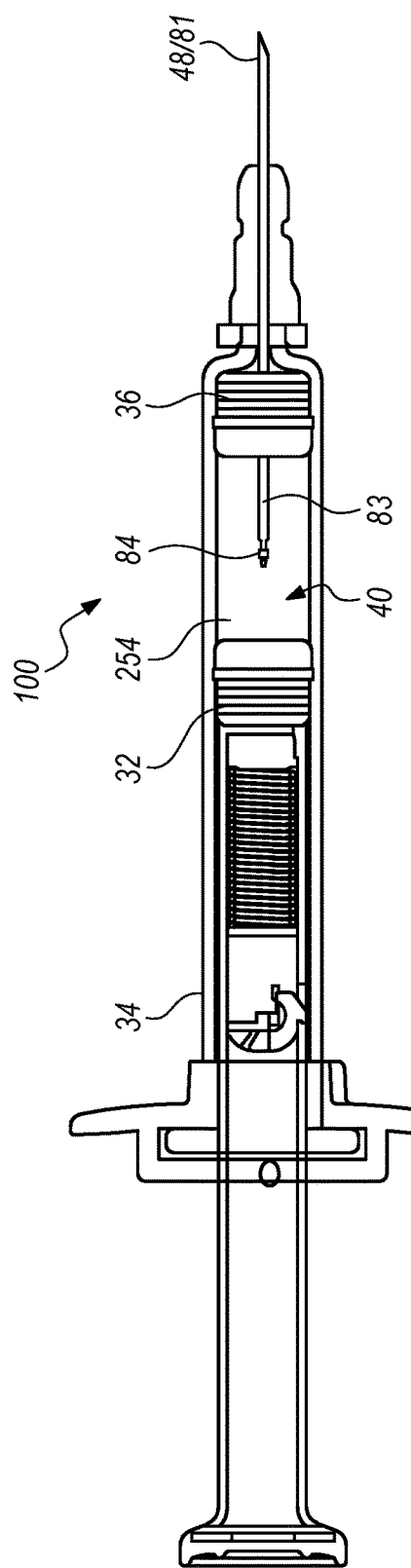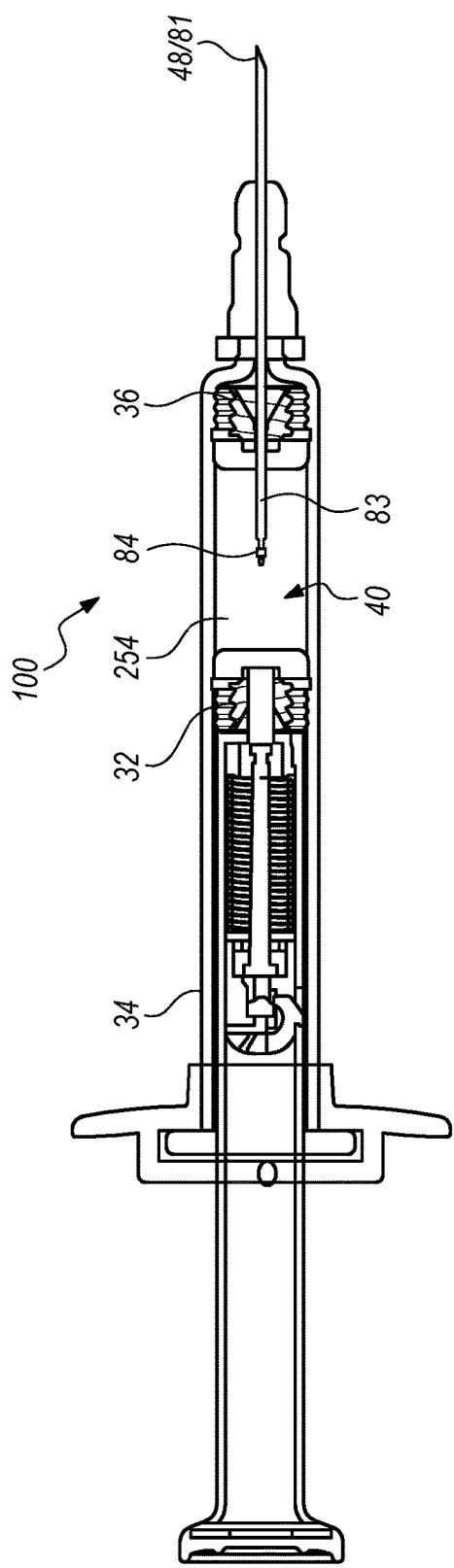
FIG. 7G
FIG. 7H

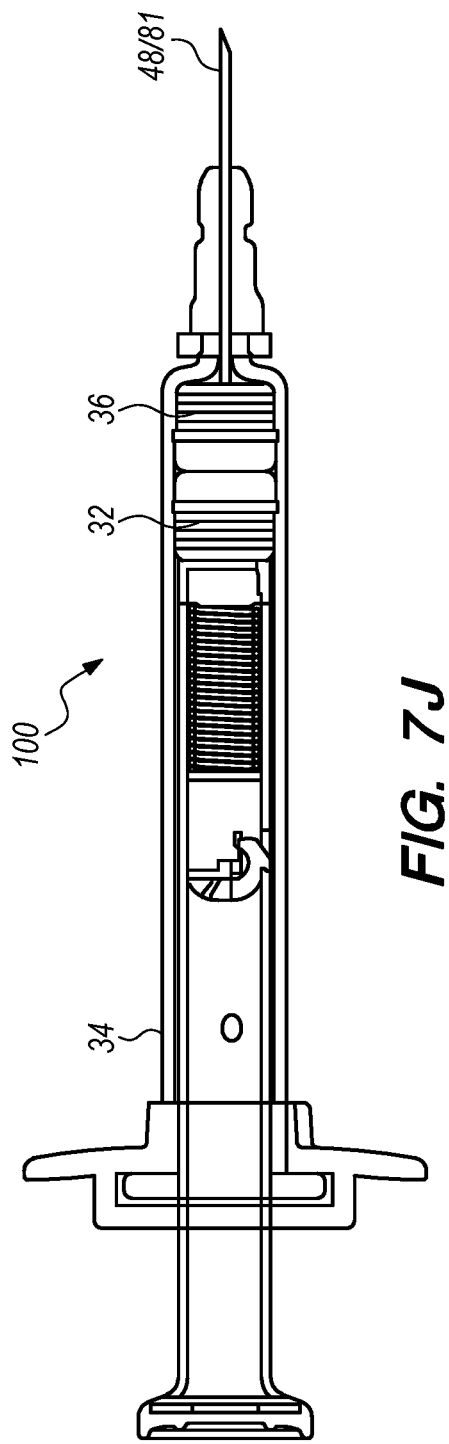
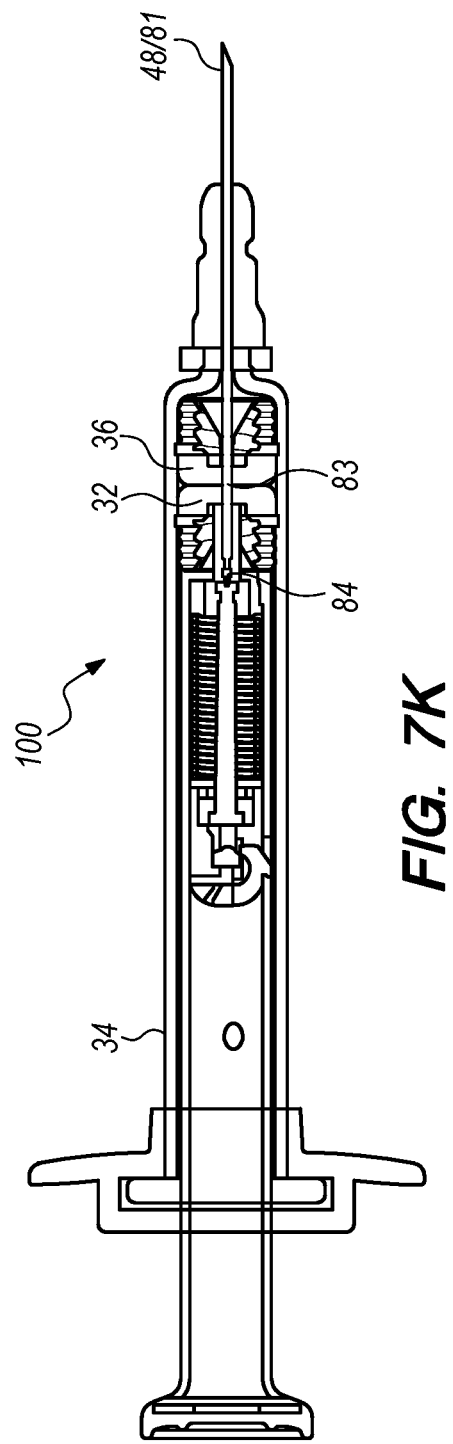

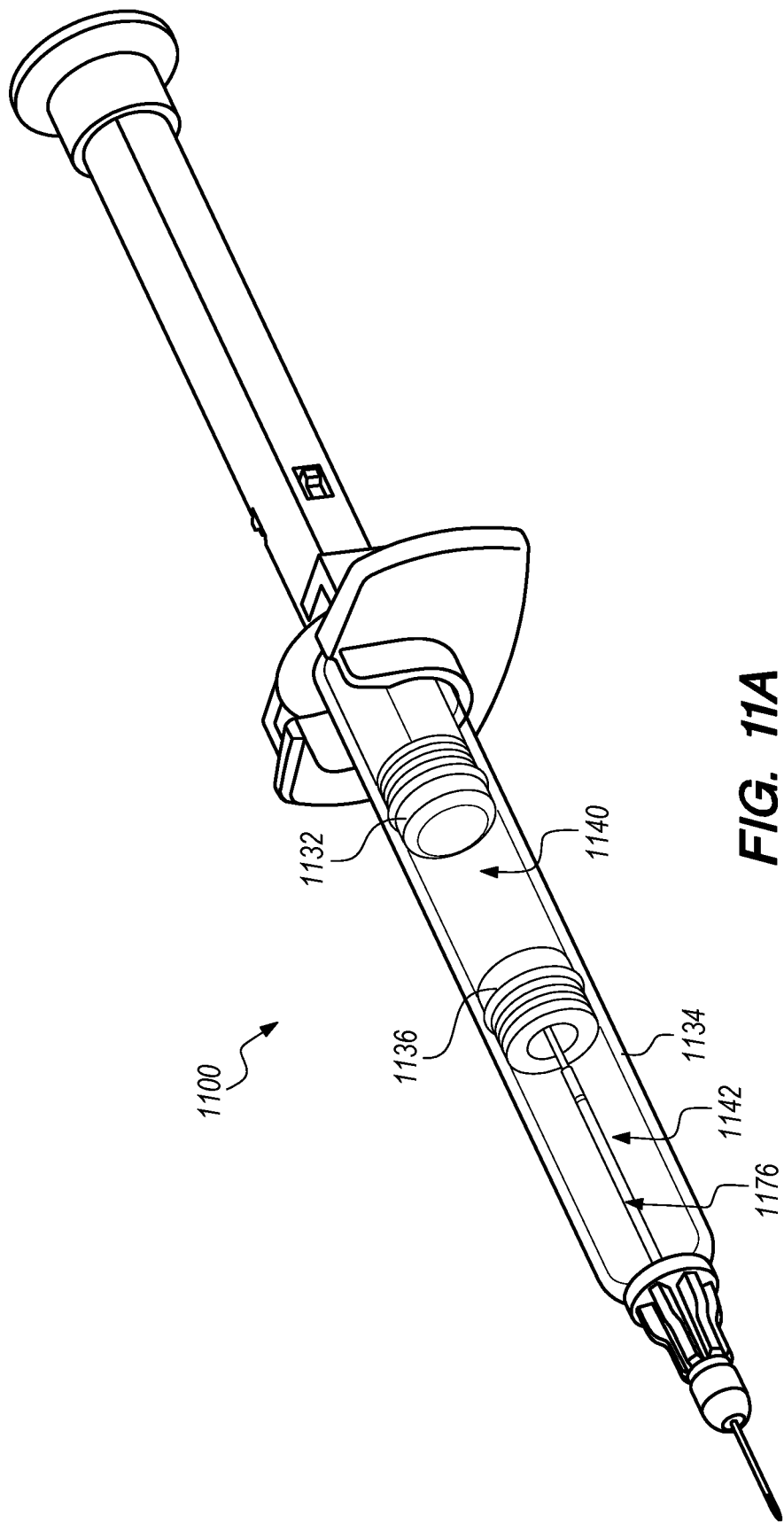

SYSTEM AND METHOD FOR SAFETY SYRINGE

The present application is a continuation of U.S. patent application Ser. No. 16/435,429 filed on Jun. 7, 2019 entitled "SYSTEM AND METHOD FOR SAFETY SYRINGE", which claims priority to (1) U.S. Provisional Patent Application Ser. No. 62/682,381, filed on Jun. 8, 2018 and entitled "SYSTEM AND METHOD FOR SAFETY SYRINGE"; and (2) U.S. Provisional Patent Application Ser. No. 62/729,880, filed on Sep. 11, 2018 and entitled "SYSTEM AND METHOD FOR SAFETY SYRINGE." This application includes subject matter similar to the subject matter described in the following co-owned U.S. patent applications: (1) U.S. Utility patent application Ser. No. 14/321,706, filed Jul. 1, 2014 and entitled "SAFETY SYRINGE"; (2) U.S. Utility patent application Ser. No. 14/543,787, filed Nov. 17, 2014 and entitled "SYSTEM AND METHOD FOR DRUG DELIVERY WITH A SAFETY SYRINGE"; (3) U.S. Utility patent application Ser. No. 14/696,342, filed Apr. 24, 2015 and entitled "SYSTEM AND METHOD FOR SAFETY SYRINGE"; (4) U.S. Utility patent application Ser. No. 15/801,239, filed on Nov. 1, 2017 and entitled "SYSTEM AND METHOD FOR SAFETY SYRINGE"; (5) U.S. Utility patent application Ser. No. 15/801,259, filed on Nov. 1, 2017 and entitled "SYSTEM AND METHOD FOR SAFETY SYRINGE"; (6) U.S. Utility patent application Ser. No. 15/801,281 filed on Nov. 1, 2017 and entitled "CARTRIDGE SAFETY INJECTION SYSTEM AND METHODS"; (7) U.S. Utility patent application Ser. No. 15/801,304 filed on Nov. 1, 2017 and entitled "SYSTEM AND METHOD FOR SAFETY SYRINGE"; and (8) U.S. Provisional Patent Application Ser. No. 62/809,369, filed on Feb. 22, 2019 and entitled "SYSTEM AND METHOD FOR SAFETY SYRINGE." The contents of the above-mentioned applications are fully incorporated herein by reference as though set forth in full.

FIELD OF THE INVENTION

The present invention relates generally to injection systems, devices, and processes for facilitating various levels of control over fluid infusion, and more particularly to systems and methods related to multiple chamber safety syringes in healthcare environments.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs. Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during assembly of a Luer coupling. The use of needle injection configurations, on the other hand, carries with it the risk of a sharp needle contacting or stabbing a person or structure that is not desired. For this reason, so called "safety syringes" have been developed.

One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for prefilled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface 14). Liquid medicine may reside in the volume, or medicine reservoir, (40) between the distal seal and the distal end (37) of the plunger tip (36). The plunger tip (36) may comprise a standard butyl rubber material and may be coated, such as with a biocompatible lubricious coating (e.g., polytetrafluoroethylene ("PTFE") or ethylene tetrafluoroethylene ("ETFE")), to facilitate preferred sealing and relative motion characteristics against the associated syringe body structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the chamber or reservoir (40), and to assist with expulsion of the associated fluid through the needle, a plunger tip (36) may be positioned within the syringe body (34). The syringe body (34) may define a substantially cylindrical shape (i.e., so that a plunger tip 36 having a circular cross-sectional shape may establish a seal against the syringe body (34)), or be configured to have other cross-sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

Moreover, an increasing number of injectable liquids (e.g., medicines) have an additional requirement that two or more components are preferably injected serially (e.g., into a patient) within a short time (e.g., seconds) of each other. Multiple components can be injected serially using separate injection devices (e.g., pre-loaded syringes) or using the same injection device to serially draw the multiple components from separate open containers and serially inject them. However, such serial injection using separate injection devices or serially drawing and injecting the multiple components necessarily results in multiple needle insertions into a patient, and can be inaccurate and lead to loss of components. Further, serial injection using separate injection devices or serially drawing the multiple components into a syringe can lead to unnecessary exposure of a user to one or more uncapped needles. Moreover, serial injection using separate injection devices or serially drawing and injecting the multiple components can cause an unacceptable lag between injections of the multiple components.

In some cases there may be a chemical reaction that takes place between the components of a multi-component injection. The use of traditional style dual chamber syringes, such as disclosed in U.S. Utility patent application Ser. No. 14/696,342, which was previously incorporated by reference herein, where the components are mixed together inside of the syringe, may not be compatible with these reactive components as the mixed components may not be suitable for injection. Some illustrative examples of this phenomenon include when the components are mixed together, the viscosity of the combined medicine increases such that the medicine cannot be easily injected through a needle. Also, other reactions such as exothermic, endothermic, etc. may take place that could prevent the use of a traditional dual chamber injection system.

Existing dual chamber injection systems (see e.g., U.S. Pat. No. 4,874,381) utilize an external bypass channel formed into the outer wall of the syringe body. The external bypass channel is positioned such that with distally directed motion of the plunger the distal stopper moves distally exposing the external bypass channel to both the proximal and distal chambers to allow liquid to travel from the proximal chamber around the distal stopper into the distal chamber, to be mixed with the medicine component in the distal chamber. If the needle or syringe is capped for drug storage, these external bypass channel style dual chamber injection systems experience an increase in pressure in the distal chamber during transfer and mixing. This increase in pressure causes resistance to transfer and difficulty in transferring all the liquid from the proximal chamber to the distal chamber. Additionally, the increase in pressure increases force the must be maintained on the plunger rod during mixing. To minimize the effects of the increase in pressure, external bypass dual chamber injection systems require the removal of a needle cap before fluid transfer and mixing, or to open the syringe and install the needle after mixing has occurred to allow for venting of the pressure in the distal chamber during transfer and mixing. These requirements increase the risk of needle stick injury, and/or require additional steps by the user. It would be beneficial to incorporate a shielded and vented pre-attached needle with integrated needle retraction to dual chamber injection systems. The shielded and vented needle shield inventions disclosed herein are applicable to external bypass style dual chamber injection systems. Additionally, it would be beneficial to integrate plunger position control methodologies to maintain precise control of the position of the distal stopper during transfer and mixing.

In addition, an increasing number of injectable liquids (e.g., medicines) have yet another requirement that time of exposure of the injectable liquid to metals (e.g., stainless steel of a needle) be minimized. Still another requirement is the desirability of systems suitable for patient self-injection.

It is also desirable to incorporate needle stick prevention technology into the injection system. The ability to retract the sharp end of the needle at least partially inside of the syringe protects the person giving the injection and the patient from inadvertent needle stick injuries.

There is a need for injection systems which address the shortcomings of currently-available configurations. In particular, there is a need for multiple chamber safety injection solutions which may utilize the existing and relatively well-controlled supply chain of conventionally delivered prefilled syringe assemblies such as those described in reference to FIGS. 5A and 5B.

SUMMARY

Embodiments are directed to injection systems. In particular, the embodiments are directed to multiple chamber safe injection systems that move the needle into a protected configuration to minimize accidental user injury and contamination with used needles.

In one embodiment, a system for serially injecting liquids includes a syringe body defining a syringe proximal opening and a distal needle interface at a distal end thereof. The system also includes proximal and distal stopper members disposed in the syringe body, forming a proximal chamber between the proximal and distal stopper members and a distal chamber between the distal stopper member and the distal end of the syringe body. The system further includes a first liquid in the distal chamber and a second liquid in the proximal chamber. Moreover, the system includes a plunger member defining a plunger interior and configured to be manually manipulated to insert the proximal stopper member distally relative to the syringe body. The plunger member includes a needle retention feature disposed in the plunger interior, an energy-storage member disposed in the plunger interior, and an energy-storage member latching member disposed in the plunger interior. In addition, the system includes a needle hub assembly coupled to the distal needle interface of the syringe body. The needle assembly includes a needle having a needle proximal end feature, a hub, and a needle latching member configured to couple the needle to the hub. Manipulating the plunger member to insert the proximal stopper member distally relative to the syringe body initially expels the first liquid from the distal chamber through the needle, and then serially expels the second liquid from the proximal chamber through the needle. The needle is at least partially retractable into plunger interior upon manipulation of the plunger member relative to the syringe body to transform the energy-storage member latching member from a latched state to an unlatched state.

In one or more embodiments, first and second sizes of the respective distal and proximal chambers can be modified by movement of the proximal and distal stopper members relative to the syringe body.

In one or more embodiments, the needle defines a needle interior, a distal end opening, a middle opening, and a proximal opening, where the distal end opening, the middle opening, and the proximal opening are fluidly coupled through the needle interior. A distance between the proximal opening and the distal end of the syringe body may be substantially equal to a length of the distal stopper member, such that when the distal stopper member is inserted to the distal end of the syringe body, the proximal stopper member is inserted distally relative to the needle to position the proximal opening in the proximal chamber. The proximal and distal stopper members and the syringe body may be configured such that distally directed force applied to the proximal stopper member is transmitted through the second liquid to the distal stopper member until the proximal stopper member is inserted distally relative to the needle to position the proximal opening in the proximal chamber. The system may have a first injection configuration where the proximal opening is disposed in the distal chamber, and a second injection configuration where the proximal opening is disposed in the proximal chamber, thereby allowing transfer of the second liquid from the proximal chamber, through the proximal opening and the needle interior, and out the distal end opening. The distal stopper member may obstruct the middle opening when the system is in the second injection configuration.

In one or more embodiments, the needle is configured to pierce entirely through at least the distal stopper member to be retracted at least partially into the plunger interior. In other embodiments, the needle may be configured to retract to a position where the distal tip thereof is disposed in the syringe body. The proximal and distal stopper members may include respective first and second polymer coatings on respective distal and proximal surfaces thereof, such that the proximal chamber is defined by the syringe body and the first and second polymer coatings.

In one or more embodiments, the distal stopper member has a funnel that tapers in a proximal direction, and a space disposed at a tapered proximal end of the funnel. The funnel may be configured to guide the needle proximal end feature into the space at the tapered proximal end of the funnel, to thereby align the needle proximal end feature with the needle retention feature in the plunger interior. The funnel may be configured to align the needle proximal end feature with the needle retention feature in the plunger interior during assembly of the system, and/or during manipulation of the plunger member to insert the proximal stopper member distally relative to the syringe body.

In one or more embodiments, the energy-storage member latching member is configured to transform from the latched state to the unlatched state at least partially retracting the needle into plunger interior after the second liquid has been expelled from the proximal chamber through the needle. The needle retention feature may be configured to actuate transformation of the energy-storage member latching member from the latched state to the unlatched state upon manipulation of the plunger member to insert the proximal stopper member to the distal end of the syringe body.

In one or more embodiments, the distal stopper member has a detent to resist passage of the needle proximal end feature therethrough. The detent may be configured such that a resistance to the needle proximal end feature passing therethrough is overcome by about 2 lbs. to about 5 lbs. of distally directed force applied to the plunger member. The detent may be modifiable to modulate the distally directed force required to overcome the resistance. The detent may have a "U" shape. The detent may include a bent wire. The detent may have a flattened cross-section. The detent may have a needle proximal end feature receiving feature. The needle proximal end feature receiving feature may have a beveled surface. The detent may include an annealed stainless alloy. The needle proximal end feature may have an angle of about 30 degrees.

In one or more embodiments, the needle has a shoulder to resist passage of the needle through the detent. The shoulder and the detent may be configured such that a resistance to the shoulder passing through the detent is overcome by about 2 lbs. to about 5 lbs. of distally directed force applied to the plunger member. The detent may be modifiable to modulate the distally directed force required to overcome the resistance. The shoulder may include an angle of about 50 degrees.

In one or more embodiments, the needle has a groove to resist passage of the needle through the detent. The groove and the detent may be configured such that a resistance to the groove passing through the detent is overcome by about 2 lbs. to about 5 lbs. of distally directed force applied to the plunger member. The detent may be modifiable to modulate the distally directed force required to overcome the resistance.

In another embodiment, a method for serially injecting first and second liquids into a patient includes providing a system including a syringe body defining a syringe proximal opening and a distal end. The system also includes proximal and distal stopper members disposed in the syringe body, forming a proximal chamber containing the second liquid between the proximal and distal stopper members and a distal chamber containing the first liquid between the distal stopper member and the distal end of the syringe body. The system further includes a plunger member defining a plunger interior and configured to be manually manipulated to insert the proximal stopper member distally relative to the syringe body. Moreover, the system includes a needle having a needle interior, a distal end opening, a middle opening, and a proximal opening, where the distal end opening, the middle opening, and the proximal opening are fluidly coupled through the needle interior. The method also includes advancing the plunger member to expel the first liquid from the distal chamber through the needle interior and the distal end opening. The method further includes further advancing the plunger member to expel the second liquid from the proximal chamber through the proximal opening, the needle interior and the distal end opening. Moreover, the method includes automatically retracting the distal needle tip into a needle hub or the syringe body when the first and second liquids been injected into the patient.

In one or more embodiments, the method also includes inserting a distal end of the needle into the patient before advancing the plunger member to expel the first liquid from the distal chamber, thereby positioning the distal end opening of the needle in the patient before expelling the first liquid. The method may also include removing air from the distal chamber before inserting a distal end of the needle into the patient. Removing air from the distal chamber may include holding the syringe body in a substantially vertical position, and manipulating the plunger member to insert the proximal stopper member distally relative to the syringe body.

In one or more embodiments, advancing the plunger member inserts the proximal stopper member distally relative to the syringe body, thereby exerting a distally-directed force through the second liquid to insert the distal stopper member distally relative to the syringe body to expel the first liquid from the distal chamber through the needle interior and the distal end opening.

In one or more embodiments, the system has a first injection configuration where the proximal opening is disposed in the distal chamber, and a second injection configuration where the proximal opening is disposed in the proximal chamber, thereby allowing transfer of the second liquid from the proximal chamber, through the proximal opening and the needle interior, and out the distal end opening. The system is in the first injection configuration when the plunger member is advanced to expel the first liquid from the distal chamber through the needle interior and the distal end opening. The system is in the second injection configuration when the plunger member is further advanced to expel the second liquid from the proximal chamber through the proximal opening, the needle interior and the distal end opening. The distal stopper member may obstruct the middle opening when the system is in the second injection configuration. The method may also include the needle piercing entirely through at least the distal stopper member, and retracting the needle at least partially into the plunger interior. In other embodiments, the method may also include retracting the needle to a position where the distal tip thereof is disposed in the syringe body.

In one or more embodiments, the distal stopper member has a funnel that tapers in a proximal direction, and a space disposed at a tapered proximal end of the funnel. The method also includes the funnel guiding the needle into the space at the tapered proximal end of the funnel, to thereby align the needle proximal end feature with the needle retention feature in the plunger interior.

In one or more embodiments, the needle also has a needle proximal end feature and the distal stopper member having a detent. The method also includes the detent resisting passage of the needle proximal end feature therethrough. Advancing the plunger member to expel the first liquid from the distal chamber through the needle interior and the distal end opening may include applying a distally directed force to the plunger member to overcome a resistance to the needle proximal end feature passing through the detent. The distally directed force may be from about 2 lbs. to about 5 lbs.

In one or more embodiments, the needle also has a shoulder and the distal stopper member having a detent. The method also includes the detent resisting passage of the shoulder therethrough. Further advancing the plunger member to expel the second liquid from the proximal chamber through the proximal opening, the needle interior and the distal end opening may include applying a distally directed force to the plunger member to overcome a resistance to the shoulder passing through the detent. The distally directed force may be from about 2 lbs. to about 5 lbs.

In one or more embodiments, the needle also has a groove and the distal stopper member having a detent. The method also includes the detent resisting passage of the groove therethrough. Further advancing the plunger member to expel the second liquid from the proximal chamber through the proximal opening, the needle interior and the distal end opening may include applying a distally directed force to the plunger member to overcome a resistance to the groove passing through the detent. The distally directed force may be from about 2 lbs. to about 5 lbs.

In still another embodiment, a system for serially injecting liquids includes a syringe body defining a syringe proximal opening and a distal interface at a distal end thereof. The system also includes proximal and distal stopper members disposed in the syringe body, forming a proximal chamber between the proximal and distal stopper members and a distal chamber between the distal stopper member and the distal end of the syringe body. The system further includes a first liquid in the distal chamber and a second liquid in the proximal chamber. Moreover, the system includes a plunger member configured to be manually manipulated to insert the proximal stopper member distally relative to the syringe body. In addition, the system includes a hub assembly coupled to the distal interface of the syringe body. The hub assembly includes a transfer pipe having a transfer pipe proximal end and a transfer pipe distal end, a hub, and a connector fluidly coupled to the transfer pipe distal end. Manipulating the plunger member to insert the proximal stopper member distally relative to the syringe body initially expels the first liquid from the distal chamber through the transfer pipe, then serially expels the second liquid from the proximal chamber through the transfer pipe.

In one or more embodiments, first and second sizes of the respective distal and proximal chambers can be modified by movement of the proximal and distal stopper members relative to the syringe body.

In one or more embodiments, the transfer pipe defines a transfer pipe interior, a distal end opening at the transfer pipe distal end, a middle opening, and a proximal opening, where the distal end opening, the middle opening, and the proximal opening are fluidly coupled through the transfer pipe interior. A distance between the proximal opening and the distal end of the syringe body may be substantially equal to a length of the distal stopper member, such that when the distal stopper member is inserted to the distal end of the syringe body, the proximal stopper member is inserted distally relative to the transfer pipe to position the proximal opening in the proximal chamber. The proximal and distal stopper members and the syringe body may be configured such that distally directed force applied to the proximal stopper member is transmitted through the second liquid to the distal stopper member until the proximal stopper member is inserted distally relative to the transfer pipe to position the proximal opening in the proximal chamber.

In one or more embodiments, the system has a first injection configuration where the proximal opening is disposed in the distal chamber, and a second injection configuration where the proximal opening is disposed in the proximal chamber, thereby allowing transfer of the second liquid from the proximal chamber, through the proximal opening and the transfer pipe interior, and out the distal end opening.

The distal stopper member may obstruct the middle opening when the system is in the second injection configuration. The proximal and distal stopper members may include respective first and second polymer coatings on respective distal and proximal surfaces thereof, such that the proximal chamber is defined by the syringe body and the first and second polymer coatings.

In one or more embodiments, the distal stopper member has a funnel that tapers in a proximal direction, and a space disposed at a tapered proximal end of the funnel. The funnel may be configured to guide the transfer pipe proximal end into the space at the tapered proximal end of the funnel, to thereby align the transfer pipe with the distal stopper member. The funnel may be configured to align the transfer pipe with the distal stopper member during assembly of the system, and/or during manipulation of the plunger member to insert the proximal stopper member distally relative to the syringe body.

In one or more embodiments, the distal stopper member has a detent to resist passage of the transfer pipe proximal end therethrough. The detent may be configured such that a resistance to the transfer pipe proximal end passing therethrough is overcome by about 2 lbs. to about 5 lbs. of distally directed force applied to the plunger member. The detent may be modifiable to modulate the distally directed force required to overcome the resistance. The detent may have a "U" shape. The detent may include a bent wire. The detent may have a flattened cross-section. The detent may have a transfer pipe proximal end receiving feature. The transfer pipe proximal end receiving feature may have a beveled surface. The detent may include an annealed stainless alloy. The transfer pipe proximal end may include a transfer pipe proximal end feature having an angle of about 30 degrees.

In one or more embodiments, the transfer pipe has a shoulder to resist passage of the transfer pipe through the detent. The shoulder and the detent may be configured such that a resistance to the shoulder passing through the detent is overcome by about 2 lbs. to about 5 lbs. of distally directed force applied to the plunger member. The detent may be modifiable to modulate the distally directed force required to overcome the resistance. The shoulder may include an angle of about 50 degrees.

In one or more embodiments, the transfer pipe having a groove to resist passage of the transfer pipe through the detent. The groove and the detent may be configured such that a resistance to the groove passing through the detent is overcome by about 2 lbs. to about 5 lbs. of distally directed force applied to the plunger member. The detent may be modifiable to modulate the distally directed force required to overcome the resistance.

In yet another embodiment, a method for serially injecting first and second liquids includes providing a system. The system includes a syringe body defining a syringe proximal opening and a distal end. The system also includes proximal and distal stopper members disposed in the syringe body, forming a proximal chamber containing the second liquid between the proximal and distal stopper members and a distal chamber containing the first liquid between the distal stopper member and the distal end of the syringe body. The system further includes a plunger member defining a plunger interior and configured to be manually manipulated to insert the proximal stopper member distally relative to the syringe body. Moreover, the system includes a transfer pipe having a transfer pipe interior, a distal end opening, a middle opening, and a proximal opening, where the distal end opening, the middle opening, and the proximal opening are fluidly coupled through the transfer pipe interior. In addition, the system includes a connector fluidly coupled to the transfer pipe interior. The method also includes advancing the plunger member to expel the first liquid from the distal chamber through the transfer pipe interior and the distal end opening. The method further includes further advancing the plunger member to expel the second liquid from the proximal chamber through the proximal opening, the transfer pipe interior and the distal end opening.

In one or more embodiments, the method also includes connecting the coupling member to an IV bag before advancing the plunger member to expel the first liquid from the distal chamber, thereby fluidly coupling the transfer pipe interior with the IV bag before expelling the first liquid. The method may also include removing air from the distal chamber before connecting the coupling member to the IV bag. Removing air from the distal chamber may include holding the syringe body in a substantially vertical position, and manipulating the plunger member to insert the proximal stopper member distally relative to the syringe body.

In one or more embodiments, advancing the plunger member inserts the proximal stopper member distally relative to the syringe body, thereby exerting a distally-directed force through the second liquid to insert the distal stopper member distally relative to the syringe body to expel the first liquid from the distal chamber through the transfer pipe interior and the distal end opening.

In one or more embodiments, the system has a first injection configuration where the proximal opening is disposed in the distal chamber, and a second injection configuration where the proximal opening is disposed in the proximal chamber, thereby allowing transfer of the second liquid from the proximal chamber, through the proximal opening and the transfer pipe interior, and out the distal end opening. The system is in the first injection configuration when the plunger member is advanced to expel the first liquid from the distal chamber through the transfer pipe interior and the distal end opening. The system is in the second injection configuration when the plunger member is further advanced to expel the second liquid from the proximal chamber through the proximal opening, the transfer pipe interior and the distal end opening. The distal stopper member may obstruct the middle opening when the system is in the second injection configuration.

In one or more embodiments, the distal stopper member has a funnel that tapers in a proximal direction, and a space disposed at a tapered proximal end of the funnel. The method also includes the funnel guiding a transfer pipe proximal end into the space at the tapered proximal end of the funnel, to thereby align the transfer pipe proximal end with the distal stopper member.

In one or more embodiments, the transfer pipe also has a transfer pipe proximal end and the distal stopper member having a detent. The method also includes the detent resisting passage of the transfer pipe proximal end therethrough. Advancing the plunger member to expel the first liquid from the distal chamber through the transfer pipe interior and the distal end opening may include applying a distally directed force to the plunger member to overcome a resistance to the transfer pipe proximal end passing through the detent. The distally directed force may be from about 2 lbs. to about 5 lbs.

In one or more embodiments, the transfer pipe also has a shoulder and the distal stopper member having a detent. The method also includes the detent resisting passage of the shoulder therethrough. Further advancing the plunger member to expel the second liquid from the proximal chamber through the proximal opening, the transfer pipe interior and the distal end opening may include applying a distally directed force to the plunger member to overcome a resistance to the shoulder passing through the detent. The distally directed force may be from about 2 lbs. to about 5 lbs.

In one or more embodiments, the transfer pipe also has a groove and the distal stopper member having a detent. The method also includes the detent resisting passage of the groove therethrough. Further advancing the plunger member to expel the second liquid from the proximal chamber through the proximal opening, the transfer pipe interior and the distal end opening may include applying a distally directed force to the plunger member to overcome a resistance to the groove passing through the detent. The distally directed force may be from about 2 lbs. to about 5 lbs.

In one embodiment, a system for mixing drug products and injecting includes a syringe body defining a proximal opening at a proximal end thereof and a distal needle interface at a distal end thereof. The system also includes proximal and distal stopper members disposed in the syringe body, forming a proximal drug chamber between the proximal and distal stopper members and a distal drug chamber between the distal stopper member and the distal end of the syringe body. The system further includes a plunger member defining a plunger interior and configured to be manually manipulated to insert the proximal stopper member relative to the syringe body. Moreover, the system includes a needle hub assembly coupled to the distal needle interface of the syringe body. The needle assembly includes a needle having a needle proximal end feature and a sharp needle distal end, and a hub. In addition, the system includes a needle cover having a threaded surface to removably couple the needle cover to the hub. The needle cover has a sealed configuration in which the needle cover prevents fluid flow through the needle distal end and a vented configuration in which the needle cover allows fluid flow through the needle distal end.

In one or more embodiments, pulling the needle cover distally relative to the syringe body moves the needle cover from the sealed configuration to the vented configuration. First and second sizes of the respective proximal and distal drug chambers may be modified by movement of the proximal and distal stopper members relative to the syringe body.

In one or more embodiments, the plunger member includes a needle retention feature disposed in the plunger interior, an energy-storage member disposed in the plunger interior, and an energy-storage member latching member disposed in the plunger interior. The needle is at least partially retractable into plunger interior upon manipulation of the plunger member relative to the syringe body to transform the energy-storage member latching member from a latched state to an unlatched state.

In one or more embodiments, the needle assembly also includes a needle latching member configured to couple the needle to the hub. The proximal and distal drug chambers may respectively contain first and second components of a drug to be mixed together prior to injecting into a patient.

In one or more embodiments, the system has a transport configuration where the needle proximal end feature is disposed in the distal drug chamber. The system also has a transfer configuration where the needle proximal end feature has at least partially pierced the distal stopper member and is at least partially disposed in the proximal drug chamber. The system further has a mixed configuration where the proximal and distal stopper members are in contact with each other, thereby transferring a first drug component from the proximal drug chamber to the distal drug chamber to mix the first drug component with a second drug component in the distal drug chamber.

In one or more embodiments, the needle also includes a distal end opening at the needle distal end, a middle opening disposed in the distal drug chamber when the system is in the transport, transfer, and mixed configurations, and a proximal opening disposed in the proximal drug chamber when the system is in the transport and transfer configurations. The proximal opening may be a slot.

In one or more embodiments, the needle cover also has a flexible finger configured to allow distal movement of the needle cover relative to the hub in the sealed configuration and to prevent distal movement of the needle cover relative to the hub in the vented configuration. The hub may have a threaded surface configured to interface with the threaded surface of the needle cover and the flexible finger, when the needle cover is in the vented configuration, to prevent distal movement of the needle cover relative to the syringe body without rotation of the needle cover relative to the syringe body.

In one or more embodiments, rotating the needle cover in a first direction relative to the syringe body moves the needle cover from the sealed configuration to the vented configuration. The hub may also include an interference member configured to removably couple the needle cover to the hub. Moving the plunger member distally relative to the syringe body may move the distal stopper member distally relative to the needle such that the needle proximal end feature penetrates the distal stopper member.

In another embodiment, a system for mixing drug products and injecting includes a syringe body defining a proximal opening at a proximal end thereof and a distal needle interface at a distal end thereof. The system also includes proximal and distal stopper members disposed in the syringe body, forming a proximal drug chamber between the proximal and distal stopper members and a distal drug chamber between the distal stopper member and the distal end of the syringe body. The system further includes a plunger member defining a plunger interior and including a threaded surface such that rotating the plunger member relative to the syringe body in a first direction advances the plunger member and inserts the proximal stopper member relative to the syringe body. Moreover, the system includes a needle hub assembly coupled to the distal needle interface of the syringe body. The needle assembly includes a needle having a needle proximal end feature and a sharp needle distal end, and a hub. In addition, the system includes a needle cover removably coupled to the hub.

In one or more embodiments, first and second sizes of the respective proximal and distal drug chambers can be modified by movement of the proximal and distal stopper members relative to the syringe body. The plunger member may include a needle retention feature disposed in the plunger interior, an energy-storage member disposed in the plunger interior, and an energy-storage member latching member disposed in the plunger interior. The needle may be at least partially retractable into plunger interior upon manipulation of the plunger member relative to the syringe body to transform the energy-storage member latching member from a latched state to an unlatched state.

In one or more embodiments, the needle assembly also includes a needle latching member configured to couple the needle to the hub. The proximal and distal drug chambers may respectively contain first and second components of a drug to be mixed together prior to injecting into a patient.

In one or more embodiments, the system has a transport configuration where the needle proximal end feature is disposed in the distal drug chamber. The system also has a transfer configuration where the needle proximal end feature has at least partially pierced the distal stopper member and is at least partially disposed in the proximal drug chamber. The system further has a mixed configuration where the proximal and distal stopper members are in contact with each other, thereby transferring a first drug component from the proximal drug chamber to the distal drug chamber to mix the first drug component with a second drug component in the distal drug chamber.

In one or more embodiments, the needle also includes a distal end opening at the needle distal end, a middle opening disposed in the distal drug chamber when the system is in the transport, transfer, and mixed configurations, and a proximal opening disposed in the proximal drug chamber when the system is in the transport and transfer configurations. The proximal opening may be a slot.

In one or more embodiments, the threaded surface of the plunger member has a double helical thread. The threaded surface of the plunger member may have a relatively large pitch thread. The threaded surface of the plunger member may have a pitch of 8.5 mm.

In one or more embodiments, the threaded surface of the plunger member is configured such that rotating the plunger member relative to the syringe body in the first direction can advance the plunger member and insert the proximal stopper member relative to the syringe body until the proximal stopper member is in contact with the distal stopper member. The threaded surface of the plunger member may be configured such that rotating the plunger member relative to the syringe body in the first direction can advance the plunger member and insert the proximal stopper member relative to the syringe body, but not until the proximal stopper member is in contact with the distal stopper member.

In one or more embodiments, the system also includes a flange coupled to the proximal end of the syringe body, the flange having a threaded surface configured to interface with the threaded surface of the plunger member to advance the plunger member and insert the proximal stopper member relative to the syringe body with rotation of the plunger member relative to the syringe body. The surface of the flange may include a removed wall. Rotating the plunger member relative to the syringe body in the first direction may move the distal stopper member distally relative to the needle such that the needle proximal end feature penetrates the distal stopper member.

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein:

FIGS. 7A to 7L illustrate various aspects of syringe based dual chamber safe injection systems during steps in methods for serially injecting liquids using same according to some embodiments.

FIGS. 11A and 11B illustrate various aspects of syringe based dual chamber safe injection systems according to some embodiments.

Figure 1A:
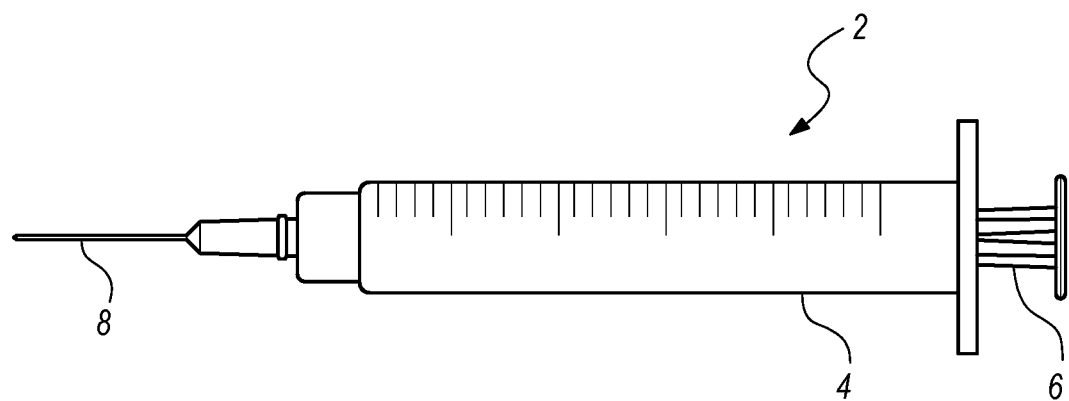
FIGS. 1A to 5C illustrate various aspects of conventional injection syringe configurations.
Figure 1B:
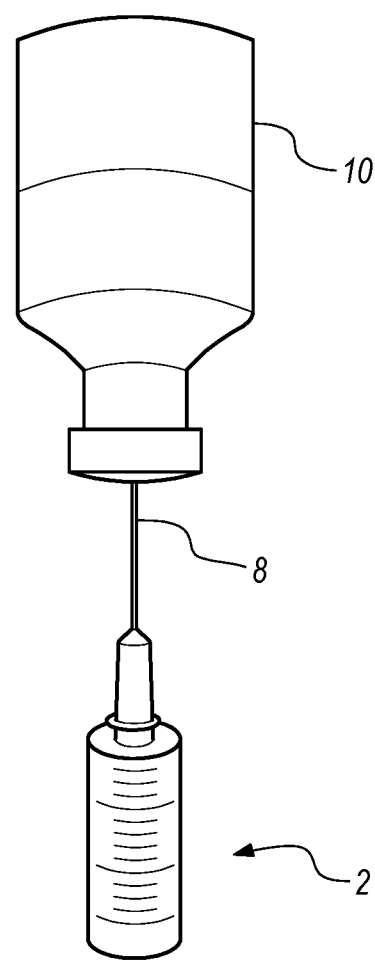
Figure 2A:
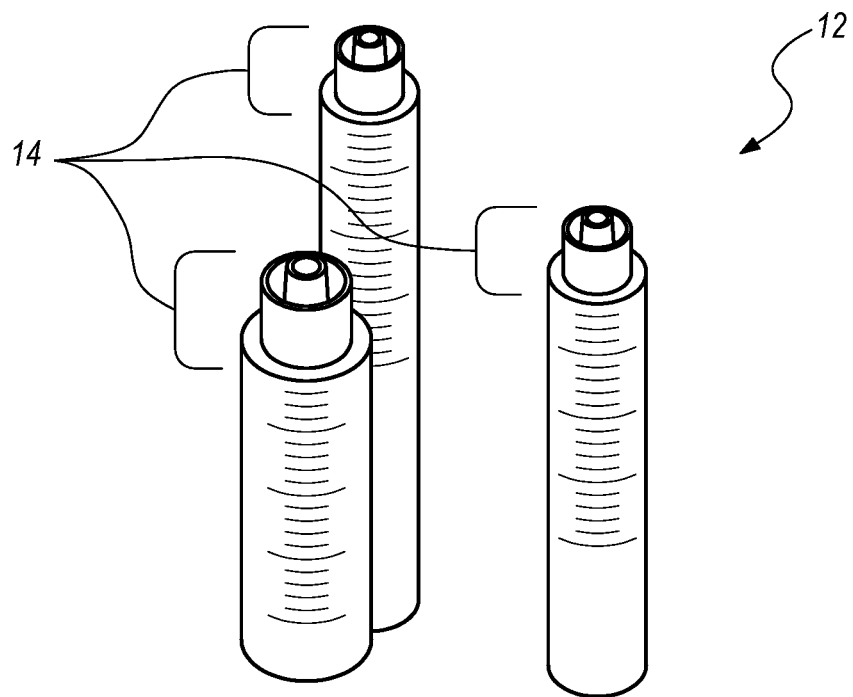
Figure 2B:
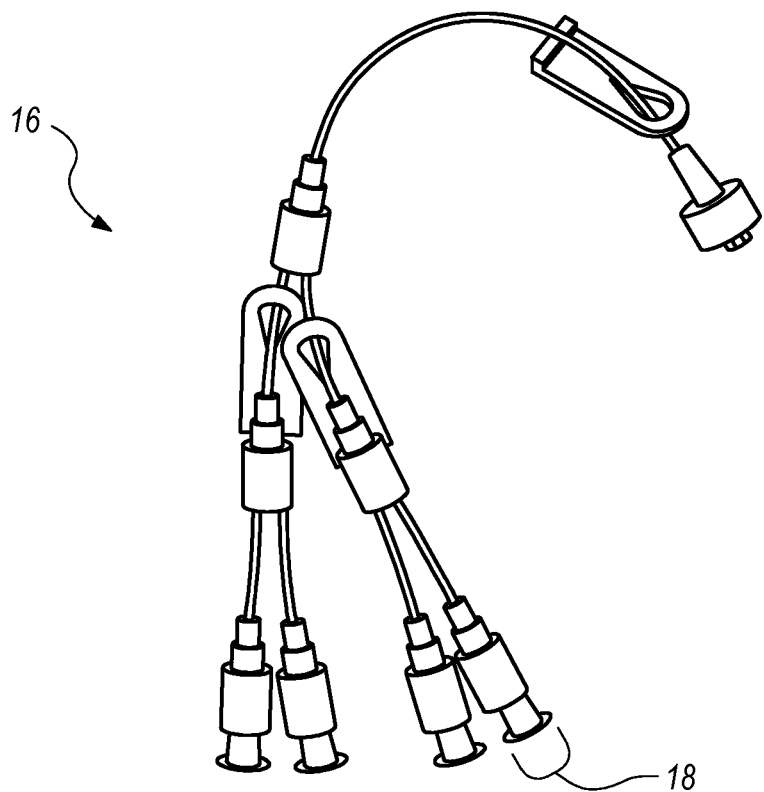
Figure 3:
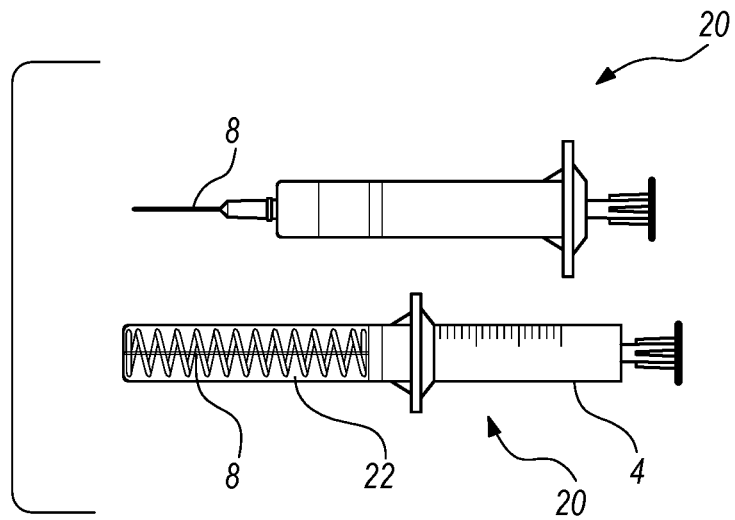
Figure 4A:
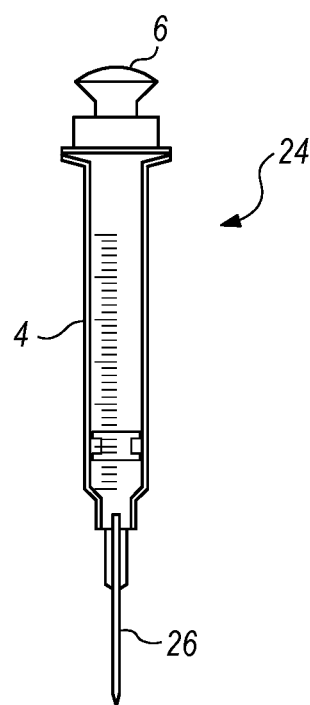
Figure 4B:
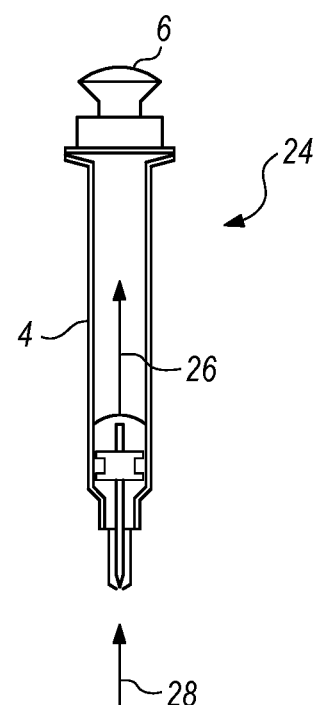
Figure 5A:
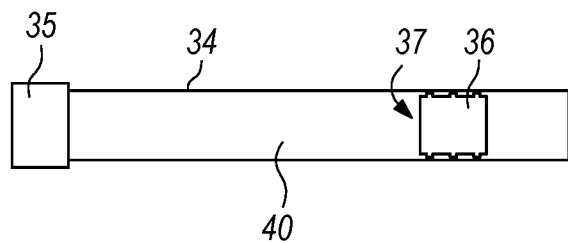
Figure 5B:
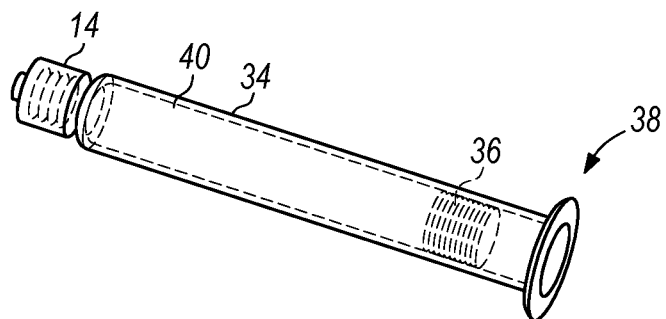
Figure 5C:
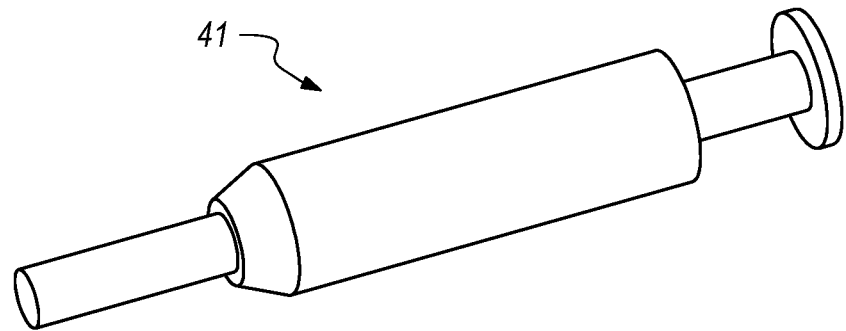

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Prefilled Dual Chamber Safe Injection Systems

Figure 6A:
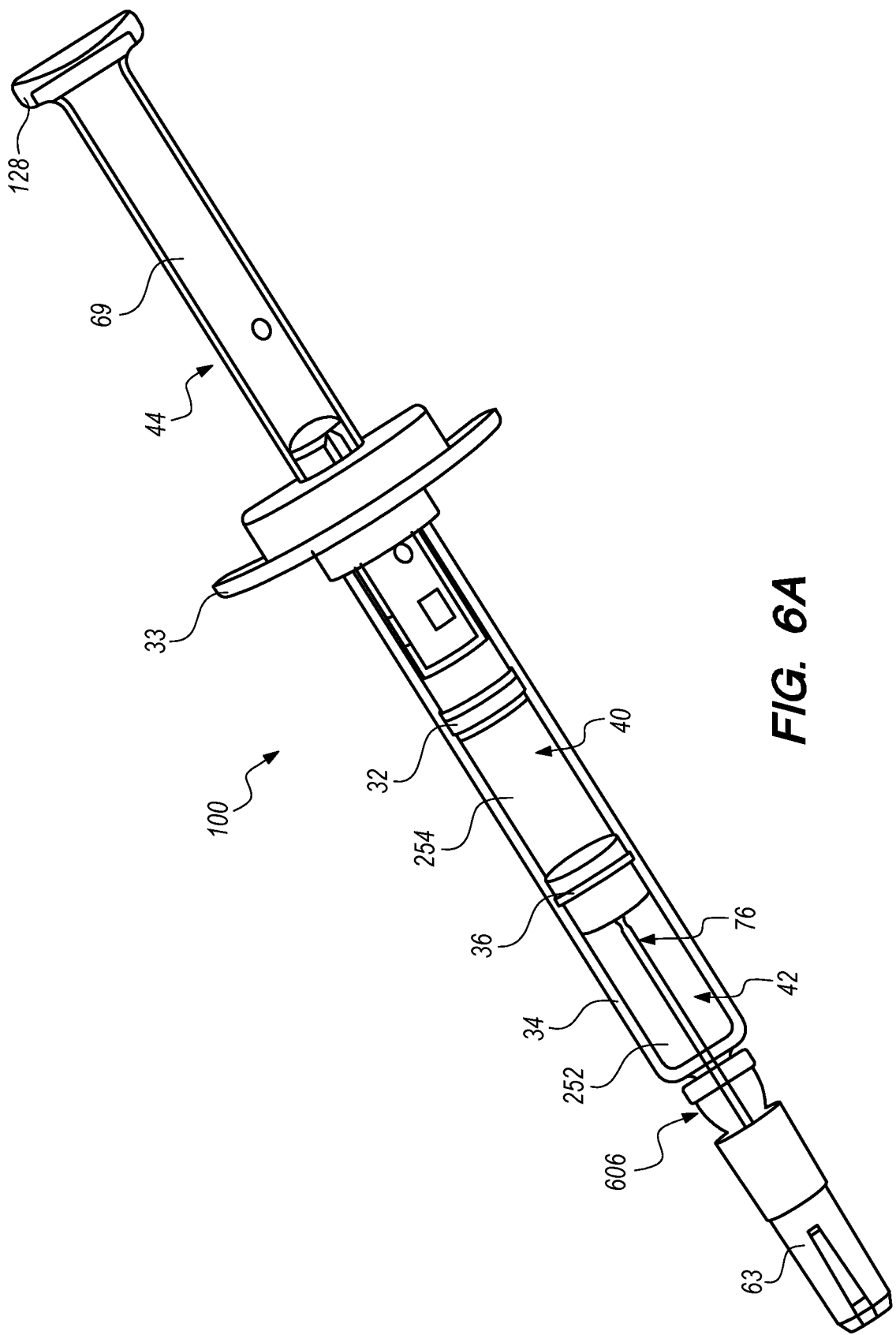
FIGS. 6A to 6Q illustrate various aspects of syringe based dual chamber safe injection systems wherein a distal needle end/tip may be withdrawn into a protected configuration after use according to some embodiments.
Figure 6B:
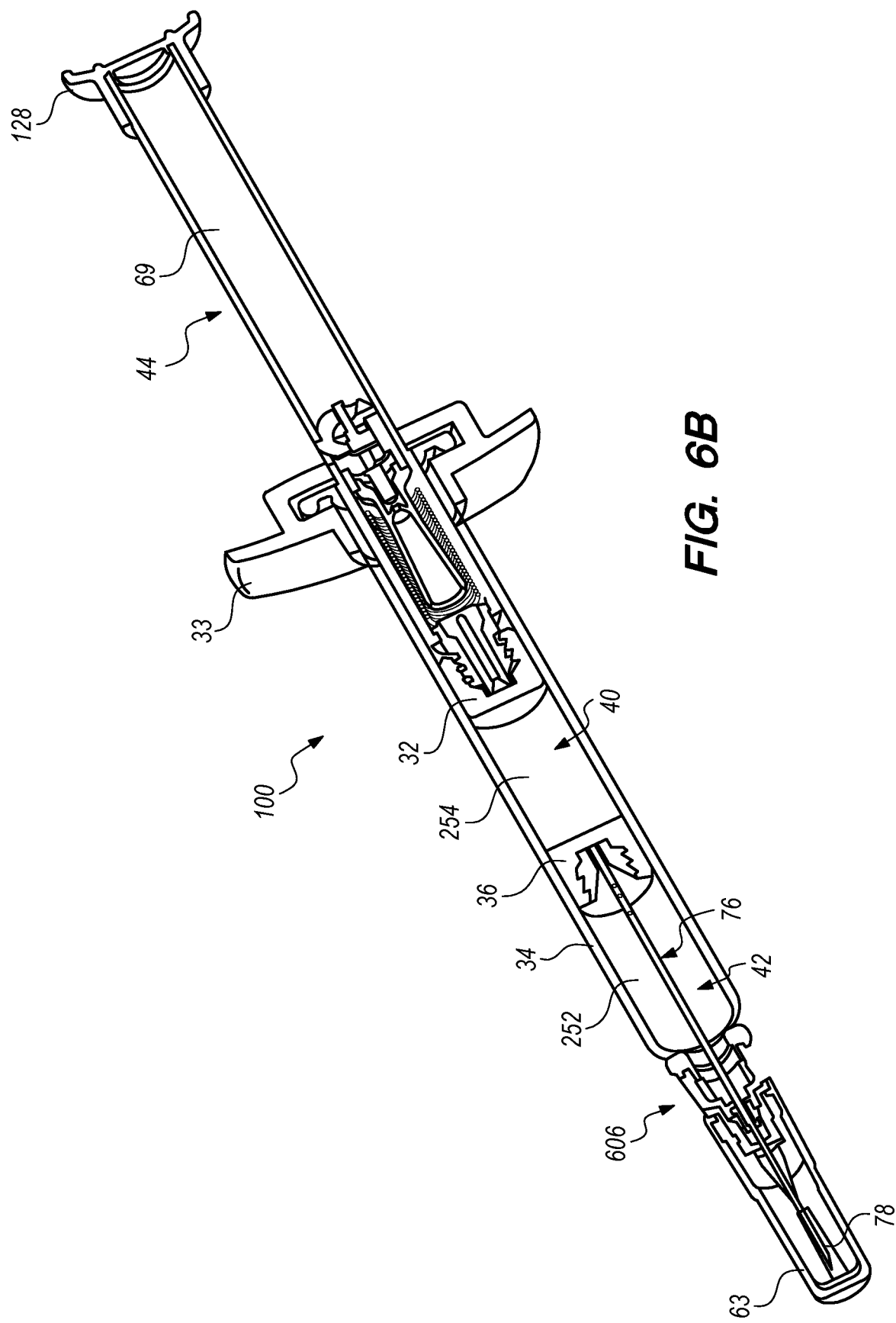

Referring to FIGS. 6A and 6B, a perspective and a longitudinal cross-section view of a prefilled dual chamber safe injection system (100) are shown, with a conventional off-the-shelf prefilled syringe body (34) with conventional proximal and distal stopper members (32, 36) disposed therein. The proximal and distal stopper members (32, 36) together with the syringe body (34) define proximal and distal chambers (40, 42). The proximal and distal stopper members (32, 36) occlude the proximal and distal ends of the proximal chamber (40). The distal stopper member (36) occludes a proximal end of the distal chamber (42). In some embodiments, the distal end of the proximal stopper member (32) and the proximal end of the distal stopper member (36) are each coated with a lubricious polymer coating (e.g., PTFE or ETFE), the first and second polymer coatings of the proximal and distal stopper members (32, 36), together with the syringe body (34) define the proximal chamber (40). The lubricious polymer coating also serves to isolate the rubber of the proximal and distal stopper members (32, 36) from the second liquid (254). The proximal and distal stopper members (32, 36) may be oriented as shown in FIGS. 6A and 6B or the distal stopper (36) may be flipped so the lubricious coating faces the distal chamber (42) such that the first liquid (252) in the distal chamber (42) contacts the lubricious coating for storage.

A needle coupling assembly (606) is disposed at the distal end of the distal chamber (42) with a needle cover member (63) installed for storage. The dual chamber safe injection system facilitates sequential injection of a first liquid (252) from the distal chamber (42) followed by injection of a second liquid (254) from the proximal chamber subject to sequential insertion of a plunger assembly (44) relative to the syringe body (34) to various degrees by a user. The plunger assembly (44) includes the proximal stopper member (32), a plunger housing member (69) and a plunger manipulation interface (128). The first and second liquids located in the distal and proximal chambers (42, 40) respectively may be any liquid or gel, such as aqueous or oil based medicine solutions.

The dual chamber safe injection system (100) has a staked needle configuration wherein upon presentation to the user, a needle assembly, including a needle spine assembly ("needle") (76) and a needle coupling assembly (606) are mounted in position ready for injection after removal of a needle cover member (63) which may comprise an elastomeric sealing material on its internal surface to interface with a needle distal end (78) and/or a distal housing portion (610, see FIGS. 6C and 6D) during storage. Alternatively, the needle cover member (63) may comprise a vent (shown and described below) for allowing pressure resulting from the transfer of the liquids (252, 254) to escape from inside the syringe body (34) while preventing contamination from entering the syringe body (34). While, the staked needle is depicted as mounted in position, the staked needle may be removably coupled to the syringe body (34) using a Luer slip or a Luer lock interface (not shown), with the proximal end (50) of the needle member extending through the Luer interface and into the distal chamber (42). Alternatively, the needle may be fixedly or removably mounted to the flange on a cartridge body instead of a syringe. Such cartridge injection systems are disclosed in U.S. Utility patent application Ser. No. 15/801,281, which was previously incorporated by reference herein. In the embodiments depicted in FIGS. 6A to 7L, a significant portion of the safe needle retraction hardware resides within a plunger housing.

Figure 6C:
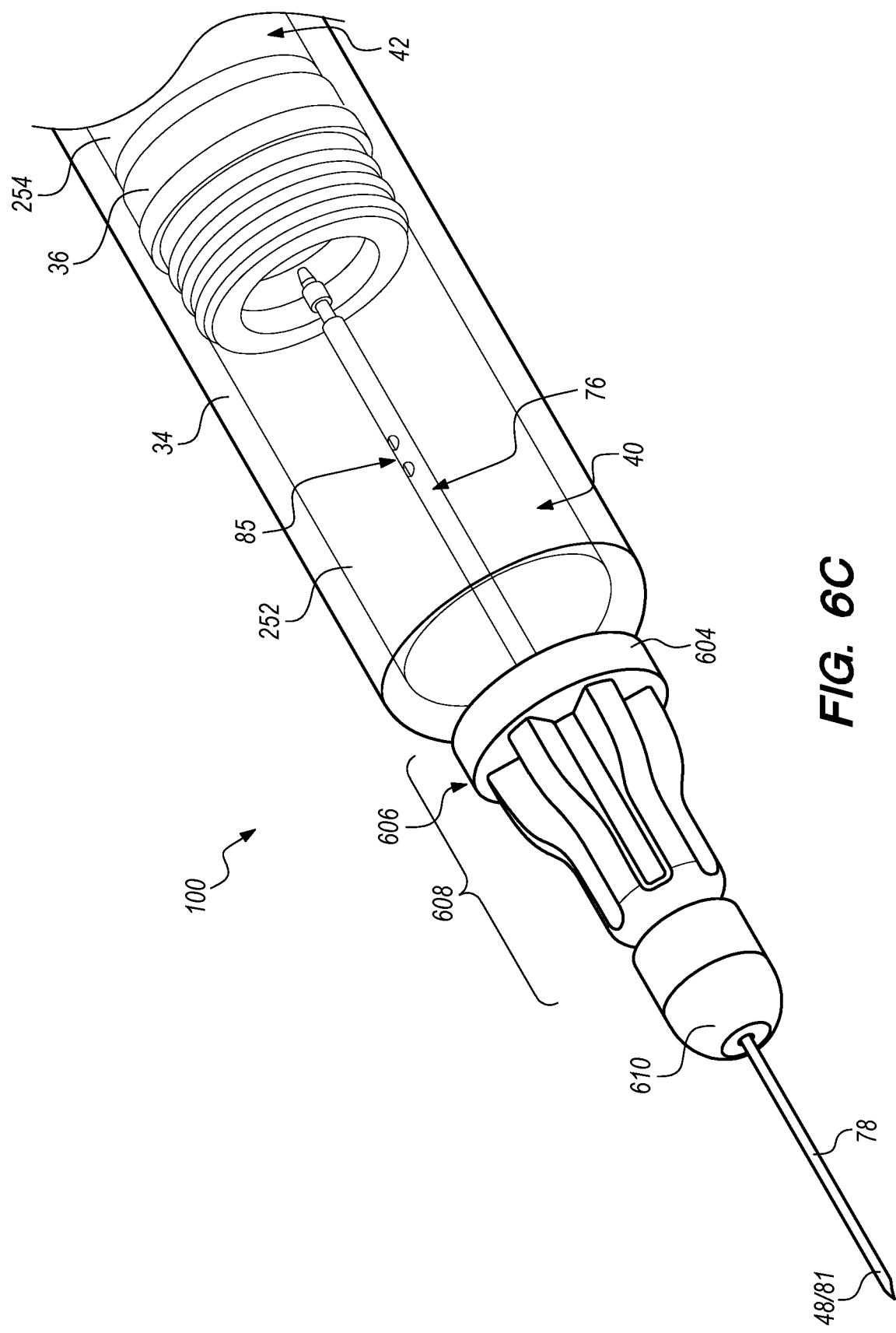
Figure 6D:
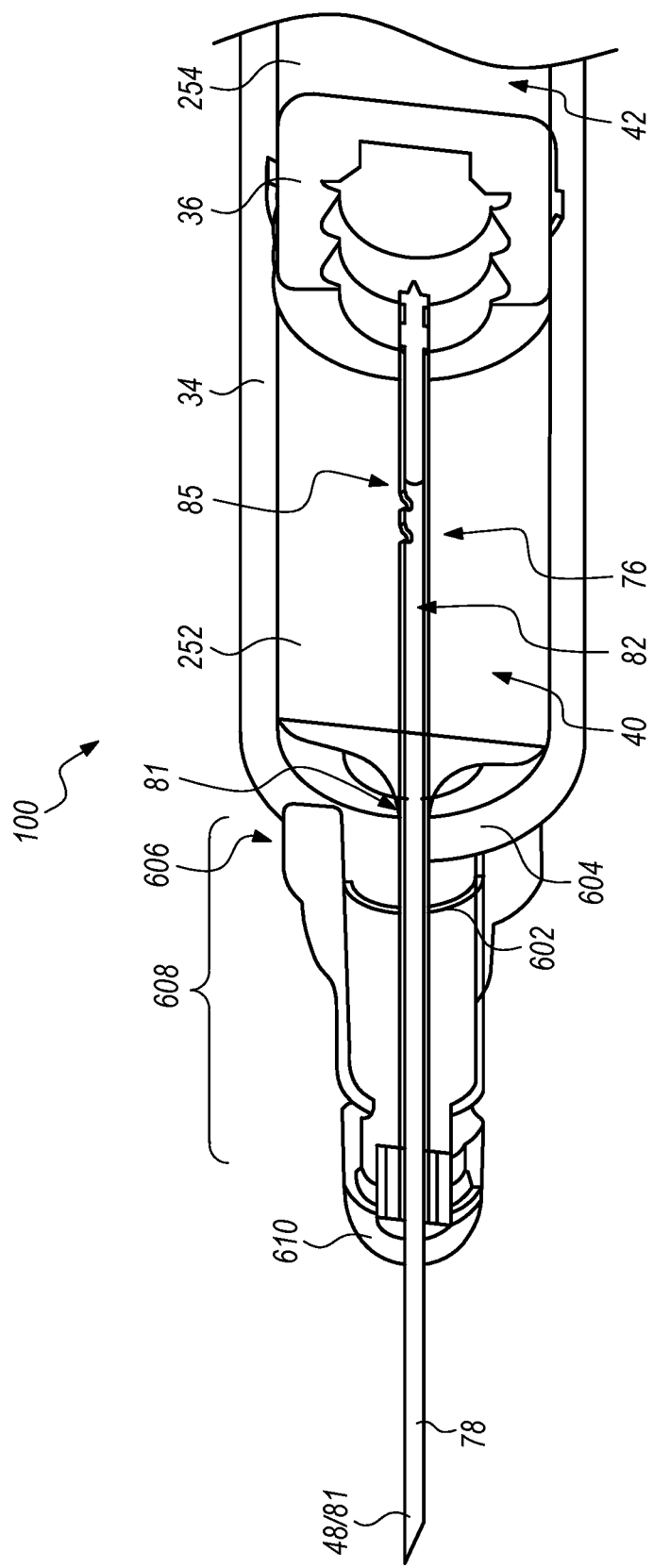

Referring to FIGS. 6C and 6D, at initial assembly time (i.e., in the factory or processing facility—not in the field in a "staked needle" configuration), the proximal housing assembly (608) is configured to snap-fit (i.e., using a snap ring element (604) comprising or coupled to the proximal housing assembly) over a slightly recessed radial portion (602) of the syringe body which is formed into the syringe body upon manufacture of the syringe body.

Figure 6E:
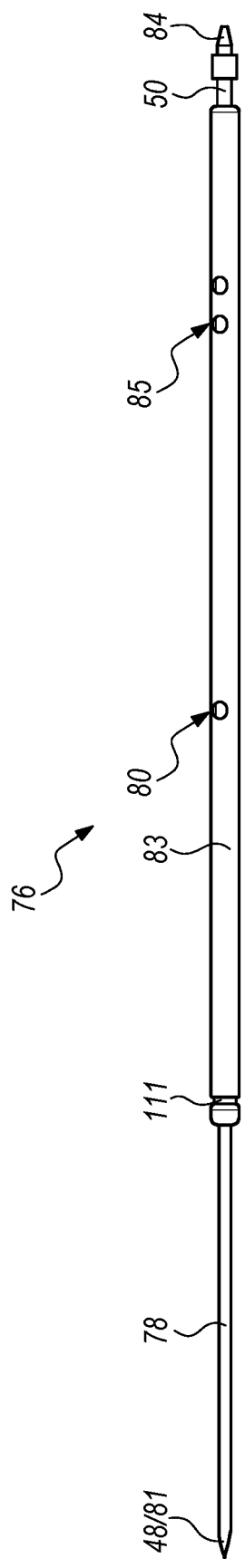

FIGS. 6E to 6O are various views of exemplary needle spine assemblies ("needles") (76) such as the one depicted in FIGS. 6A to 6D and various portions thereof according to some embodiments. FIGS. 6E/6F, 6G/6H, 6I/6J, 6K/6L, and 6M/6N are corresponding pairs of side and longitudinal cross-section views of needle spine assemblies (76) and various portions thereof. FIG. 6O is a perspective view of a needle spine assembly (76) according to some embodiments.

The needle spine assemblies (76) include a needle proximal end (50) and a needle distal end (78) coupled to opposite (i.e., respective proximal and distal) ends of a needle joining member (83). The needle joining member (83) is configured to have a necked-down or radially-reduced portion (111) that is configured to interface with a latching member (612) and movable block member (614) such that during injection, the needle joining member (83), the needle proximal end (50), and the needle distal end (78) remain fixed in a proximal direction relative to the syringe body (34) (see FIGS. 6P and 6Q). After complete insertion of the plunger assembly relative to a small diameter flange (33) (i.e., near or after full expulsion of the second liquid (254) which may be contained within the proximal chamber (40) of the syringe body (34)), the movable block member (614) is advanced relative to the distal housing portion (610) such that the plurality (two are illustrated) of cantilevered latch members (616) of the latch member (612) are urged out of the way by the movable block member (614). In particular, the needle spine assembly (76) is forced distally by complete advancement of the plunger assembly, advancing the movable block member (614) to move the cantilevered latch members (616). Moving the cantilevered latch members (616) allows the needle distal end (78), joining member (83), and proximal end (50) to be retracted through their coupling, thereby placing a sharpen needle tip (48) safely within the plunger housing member (69). Alternatively, the needle tip (48) may be retracted to a position proximal of the outer surface of the distal housing portion (610) to safely protect the sharp point from the user. In other words, the cantilevered latch members (616) retain the position of the needle tip (48) during injection and needle/syringe assembly, until they are pushed out of the way by the movable block member (614) at full plunger insertion as further described in U.S. Utility patent application Ser. No. 15/801,259, which was previously incorporated by reference herein. After the cantilevered latch members (616) are pushed out of the way by the movable block member (614), the needle (76) is free to be automatically withdrawn when triggered by further distal movement of the needle spine assembly (76) as described in U.S. patent application Ser. Nos. 14/696,342, which was previously incorporated by reference herein, and 62/416, 102, which is fully incorporated herein by reference as though set forth in full.

Figure 6F:
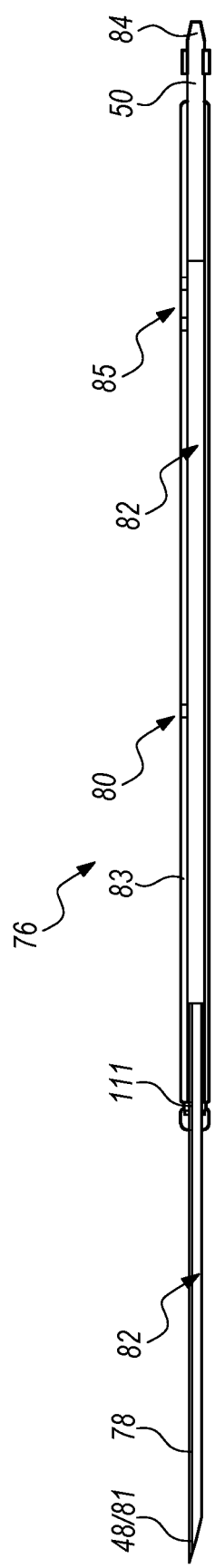
Figure 6I:
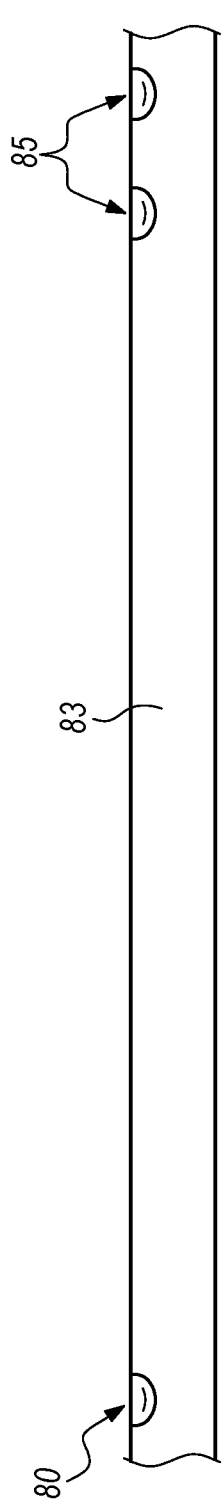
Figure 6J:
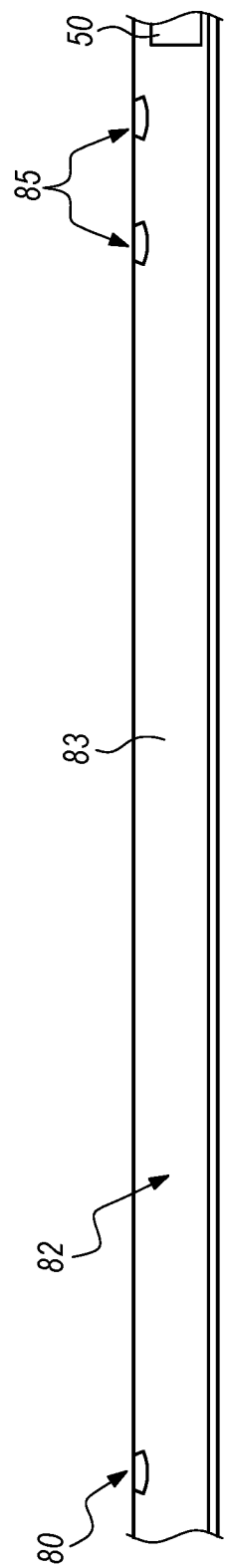
Figure 6K:
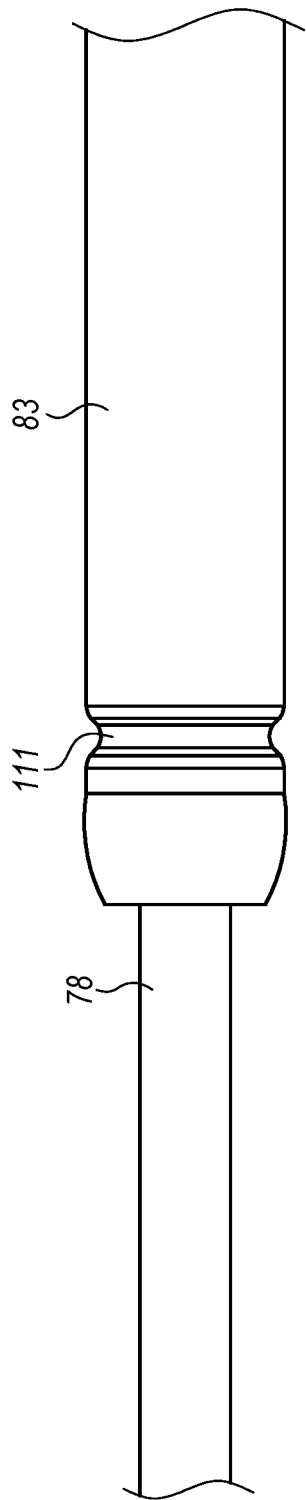
Figure 6L:
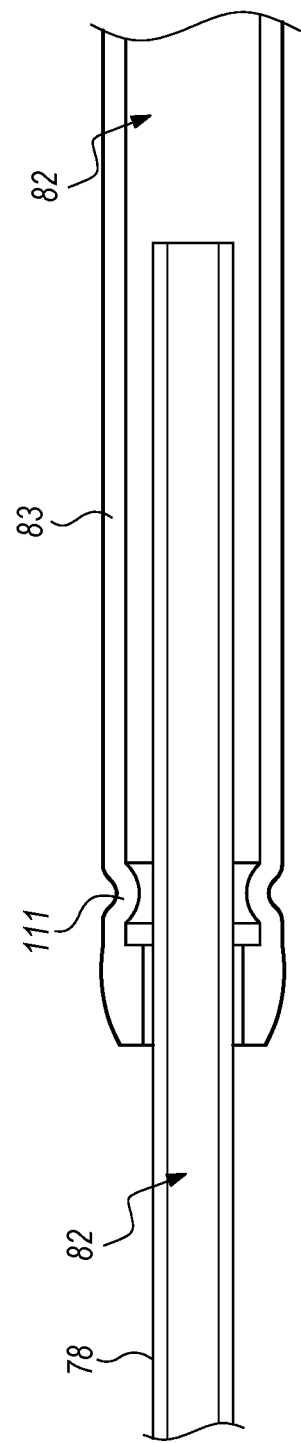
Figure 60:
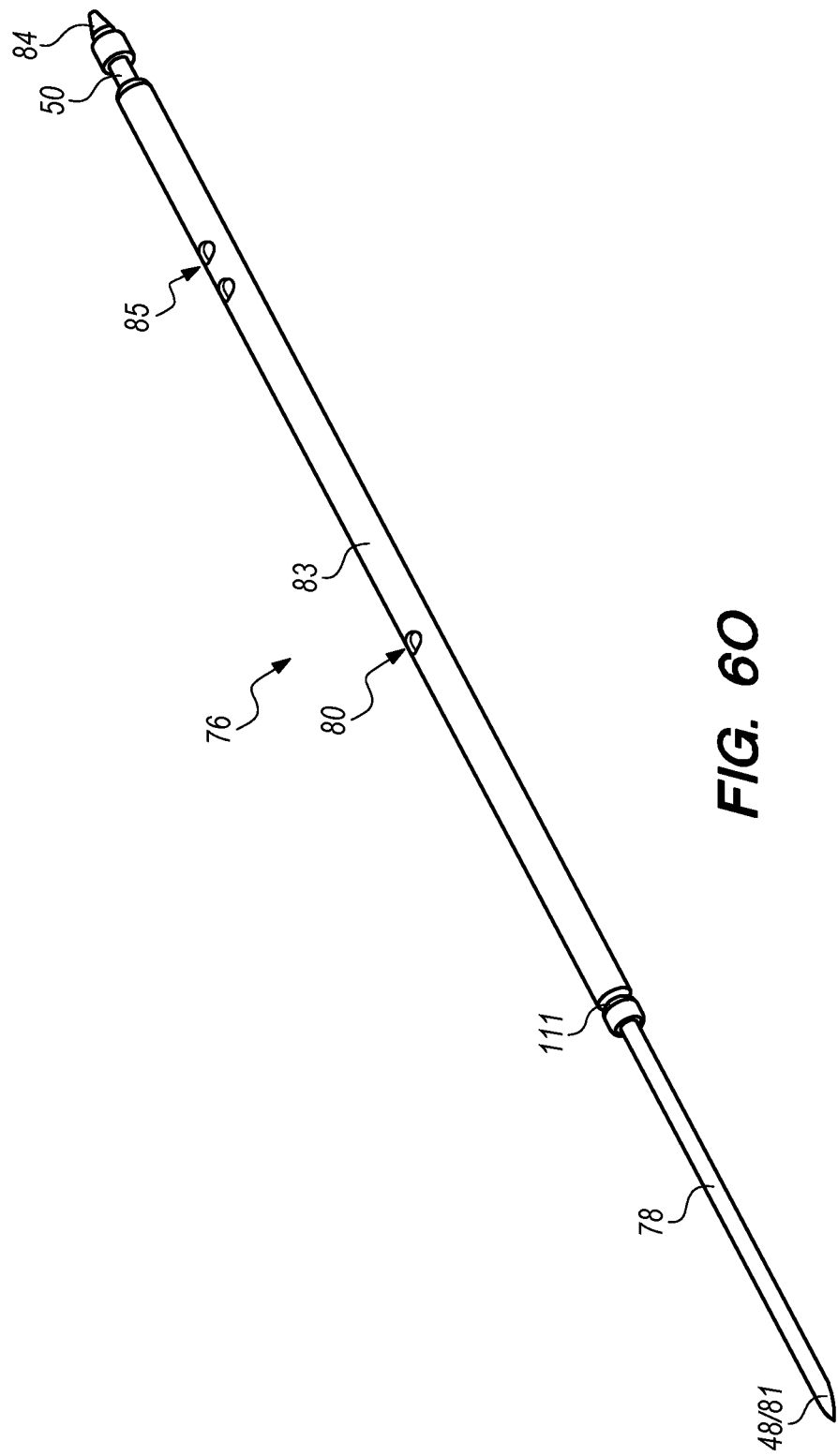

FIGS. 6E to 6O illustrate aspects of a needle spine assembly (76), comprising the elements of a needle assembly without the needle coupling assembly (606). As shown in FIGS. 6F and 6H, the needle proximal end (50) includes a coupling member (86) at a distal end thereof, and a sharpened proximal end (84). A needle joining member (83) couples the coupling member (86) to the needle distal end (78). The needle distal end (78), coupling member (86) on the needle proximal end (50), and needle joining member (83) may be held together with interference fits, welds, and/or adhesives. The needle proximal end (50) is coupled to the needle joining member (83) such that the interior of the needle joining member (83) is occluded at the proximal end thereof, preventing fluid flow through the proximal end of the needle joining member (see FIG. 6H). The proximal end (84) of the needle proximal end (50) in the depicted embodiment forms a "harpoon" style geometry configured to stab into and hold onto a compliant member to which it may be interfaced, for withdrawal of the needle spine assembly (76) into the plunger housing member (69). Withdrawal of the needle spine assembly (76) into the plunger housing member (69) using the proximal end (84) is further described in U.S. Utility patent application Ser. Nos. 15/801, 259 and 15/801,304, which were previously incorporated by reference herein. The needle proximal end (50) may be formed from a metal rod and a metal ring using welding, laser cutting, stamping, and/or machining techniques, for example.

Referring to FIGS. 6G to 6N, the needle joining member (83) and the needle distal end (78) may provide a fluid pathway selectively coupling the proximal and distal chambers (40, 42) to the exterior of the system (100). This fluid pathway may include one or more proximal openings (85) at the proximal end of the needle joining member (83) adjacent to the needle proximal end (50) as shown in FIGS. 6G to 6N. In the embodiment depicted in FIGS. 6E to 6O, there are two proximal openings (85). In other embodiments, there can be fewer (e.g., one) or more (e.g., three) proximal openings (85). The fluid pathway may also include one or more middle openings (80) distal of the one or more proximal openings (85). In the embodiment depicted in FIGS. 6E to 6O, there is one middle opening (80). In other embodiments, there can be more (e.g., two) middle openings (80). The proximal and middle openings (85, 80) may be formed by cutting (e.g., a hole or a slot) in the side wall of the hollow joining member (83).

The distal portion (78) of the needle spine assembly (76) comprises a sharpened hypodermic needle tip (48, see FIGS. 6M and 6N) formed on an extreme distal end of the distal portion (78). The fluid pathway may also include one or more distal openings (81) in the needle tip (48). In the embodiment depicted in FIGS. 6E to 6O, there is one distal opening (81). In other embodiments, there can be more (e.g., two) distal openings (81). The distal openings (81) may be formed by skiving or cutting the distal end of the distal portion (78) or cutting (e.g., a hole or a slot) in the side wall of the hollow joining member (83).

Figure 7C:
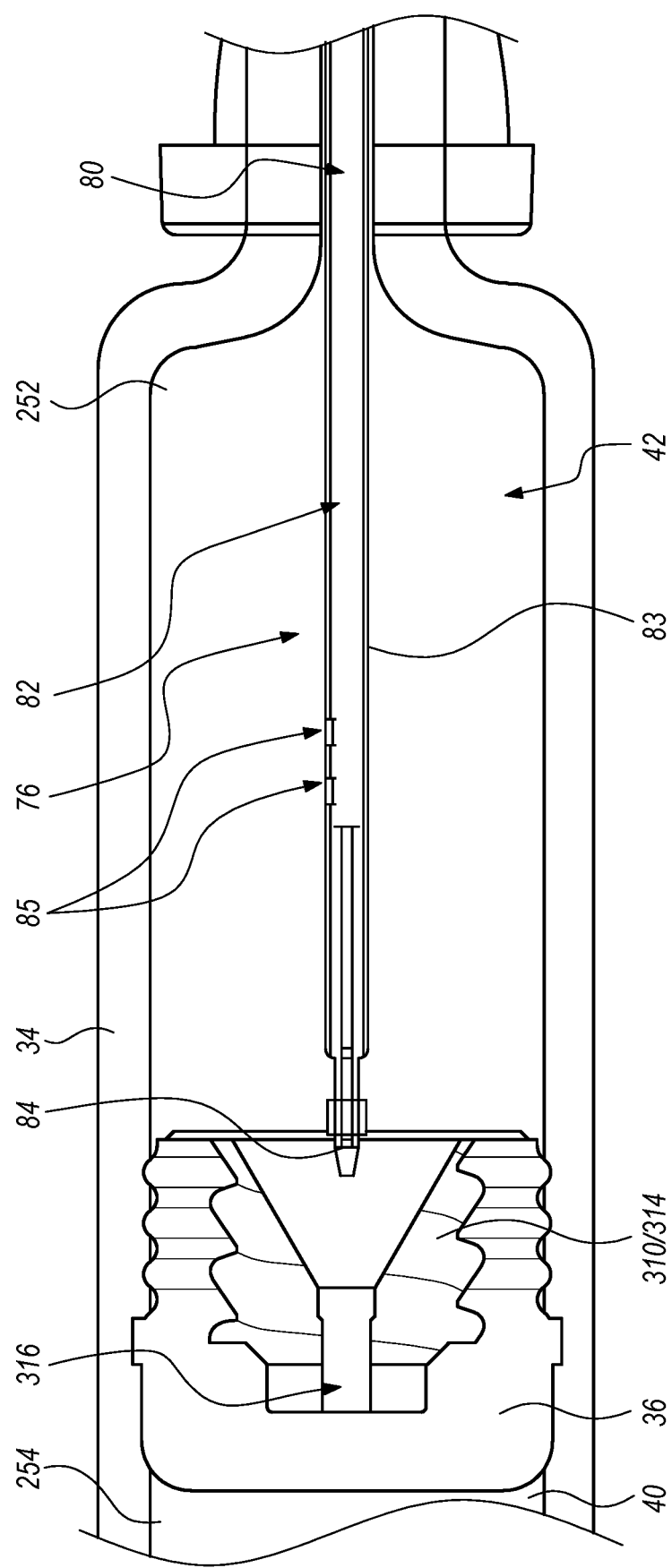

The proximal, middle, and distal openings (85, 80, 81) all fluidly communicate with an interior (82) of the needle spine assembly (76). The interior (82) of the needle spine assembly (76) extends from the proximal openings (85) to the distal opening (81). Modifying the relative positions of the needle spine assembly (76) and the proximal and distal stopper members (32, 36) selectively couples the proximal and distal chambers (40, 42) to the exterior of the system (100) through the interior (82) of the needle spine assembly (76). In the embodiment depicted in FIGS. 7A to 7I, the middle opening (80) is constantly disposed in the distal chamber (40) during injection. When the proximal openings (85) are also disposed in the distal chamber (40) (FIGS. 7A to 7C) or when one or more of the proximal openings (85) are obstructed by the distal stopper member (36), the distal chamber (42) is fluidly coupled to an exterior of the system (100) through one or more of the proximal openings (85) and/or the middle opening (80), the interior (82) of the needle spine assembly (76), and the distal opening (81). FIGS. 7A to 7C depict a first injection configuration in which the first liquid (252), but not the second fluid (254), may be injected via the interior (82) of the needle spine assembly (76) and the distal opening (81). When one or more of the proximal openings are disposed in the proximal chamber (42) and the middle opening (80) is obstructed by the distal stopper member (36) (FIGS. 7G to 7I), the proximal chamber (40) is fluidly coupled to an exterior of the system (100) through one or more of the proximal openings (85), the interior (82) of the needle spine assembly (76), and the distal opening (81). FIGS. 7G to 7I depict a second injection configuration in which the second liquid (254), but not the first fluid (252), may be injected via the interior (82) of the needle spine assembly (76) and the distal opening (81). As shown in FIG. 7I, the distal stopper member (36) obstructs fluid flow (e.g., of the second fluid (254)) to the middle opening (80).

FIGS. 7A to 7I depict a prefilled dual chamber safe injection system (100) according to one embodiment with the needle spine assembly (76) depicted in FIGS. 6E to 6O in various steps of a method for sequential injection.

FIGS. 7A to 7C depict the dual chamber safe injection system (100) in a first step of a method for sequential injection (side view, longitudinal cross-sectional view, detailed longitudinal cross-sectional view) with the system (100) in the first injection configuration. In the first step depicted in FIGS. 7A to 7C, the needle cover member (63, see FIGS. 6A and 6B) has been removed to prepare the system (100) for use. The distal chamber (42) may be optionally "de-bubbled" by holding the syringe body in a substantially vertical position, and manipulating the plunger member to insert the proximal stopper member distally relative to the syringe body. During de-bubbling, any air in the distal chamber (42) will exit the system (100) via the middle opening (80), the interior (82) of the needle spine assembly (76), and the distal opening (81) because the air will rise to the top of the distal chamber (42) where the little opening (80) is located.

FIG. 7C also shows that the distal stopper member (36) includes a distal stopper bushing (310) that defines an alignment funnel (314) to guide the proximal end (84) of the needle proximal end into position (in a space (316) at a tapered proximal end of the distal stopper bushing (310)) during injection. In other embodiments, the alignment funnel (314) is configured to guide the proximal end (84) of the needle proximal end into position during assembly the dual chamber safe injection system (100). Further details regarding the alignment funnel (314) are described in U.S. Utility patent application Ser. No. 15/801,259, which was previously incorporated by reference herein.

Figure 7F:
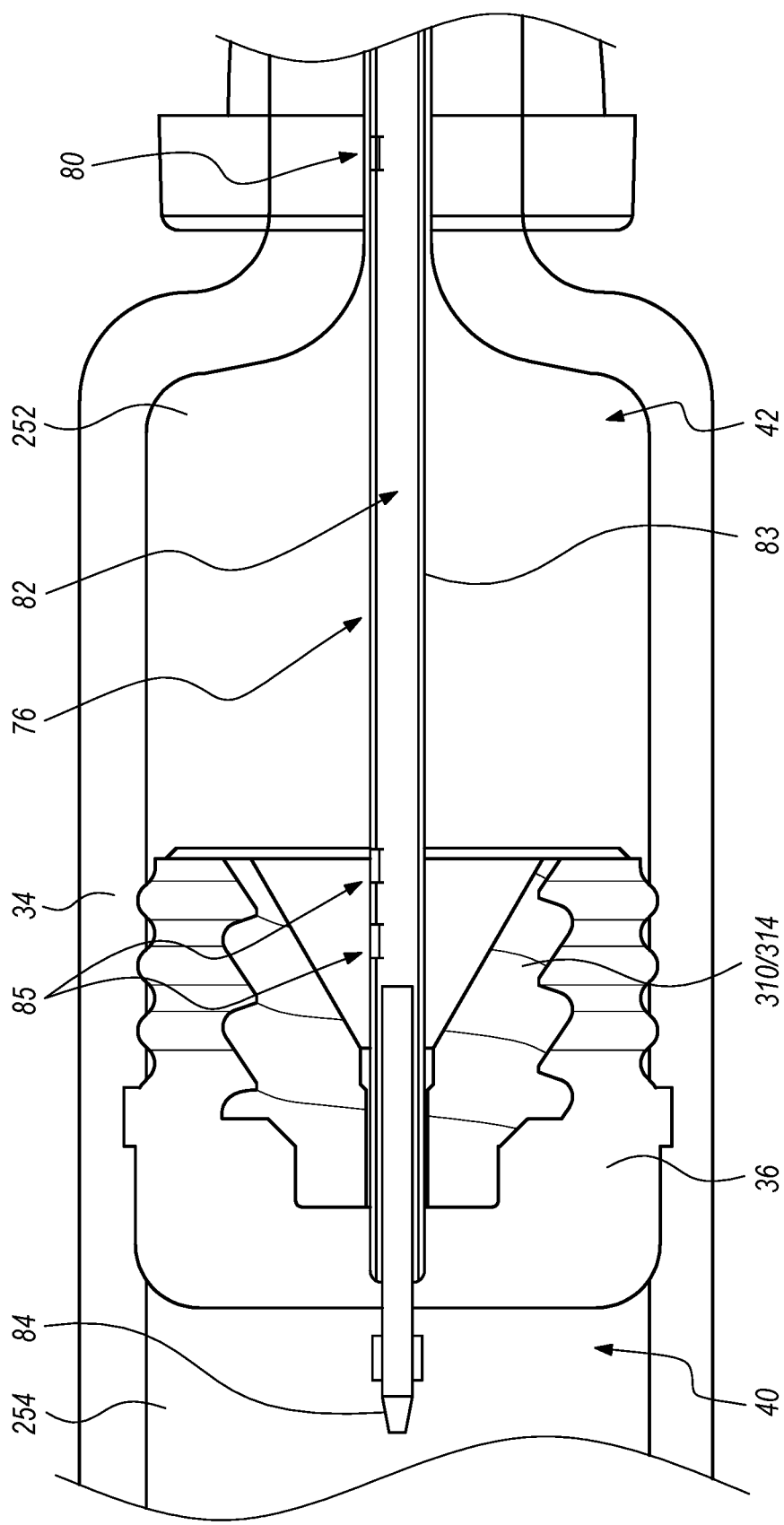
Figure 71:
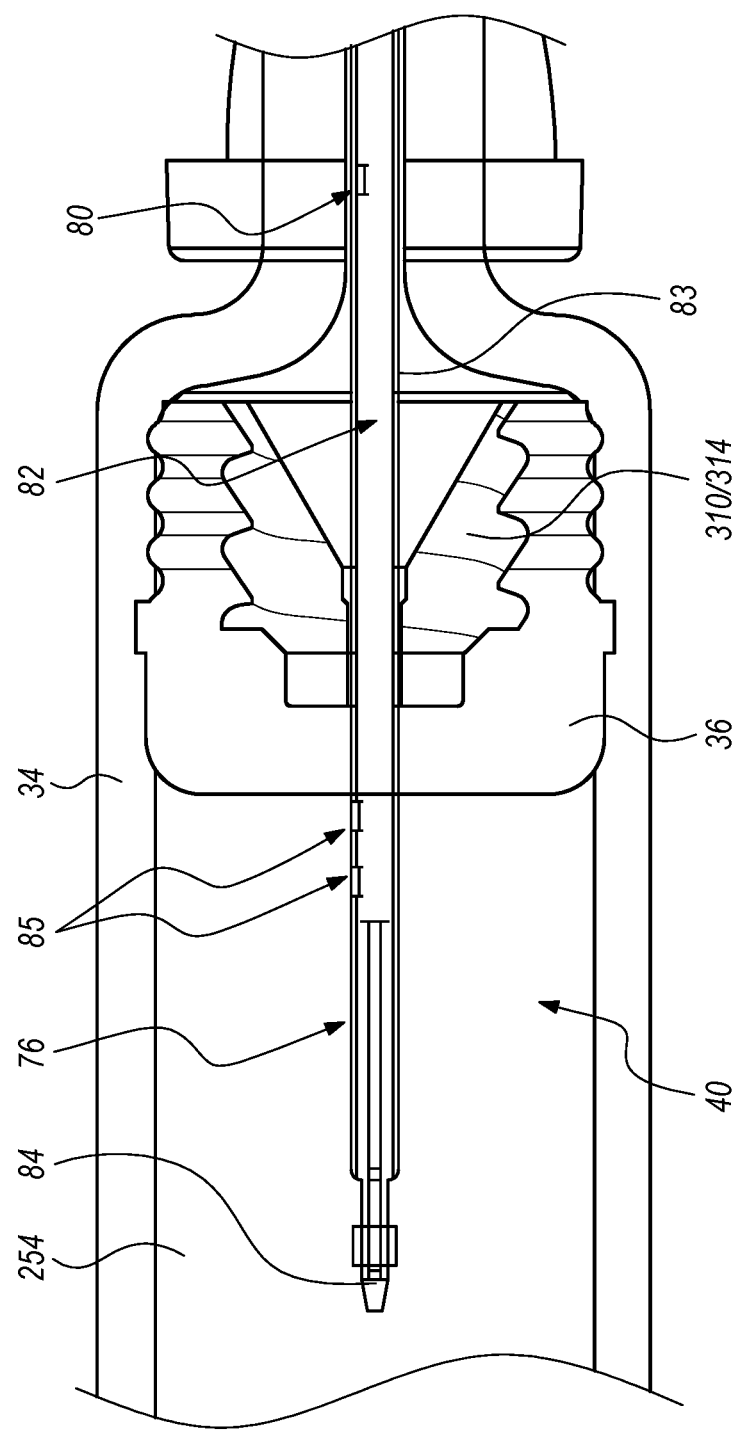

FIGS. 7D to 7F depict the dual chamber safe injection system (100) in a second step of the method for sequential injection (side view, longitudinal cross-sectional view, detailed longitudinal cross-sectional view) with the system (100) in the first injection configuration. In the second step depicted in FIGS. 7D to 7F, the proximal stopper member (32) has been moved distally relative to the syringe body (34) by applying a distally directed force to the plunger member as described in U.S. Utility patent application Ser. No. 15/801,259, which was previously incorporated by reference herein. Because the portion of the needle joining member (83) having the proximal openings (85) has not passed through the distal stopper member (36) to enter the proximal chamber (40), the proximal chamber (40) is essentially a closed chamber. Accordingly, distal movement of the proximal stopper member (32) moves the incompressible second liquid (254) in the proximal chamber (40) and the distal stopper member (36) by the same distance in the distal direction. Distal movement of the distal stopper member (36) increases the pressure in the distal chamber (42), thereby ejecting some of the first liquid (252) out of the distal chamber (42) and the system (100) through the proximal openings (85) and/or the middle opening (80), the interior (82) of the needle spine assembly (76), and the distal opening (81).

In some embodiments, the needle tip (48) and the distal opening (81) are disposed in (e.g., stabbed into) a patient before a distally directed force is applied to the plunger member to inject the first liquid (252) into the patient. The sharpened needle tip (48, see FIGS. 6M and 6N) facilitate such an injection.

FIG. 7F also shows that the proximal end (84) of the needle proximal end into position during injection has been guided through the middle of the distal stopper member (36) by the alignment funnel (314) defined by the distal stopper bushing (310). Further details regarding the alignment funnel (314) are described in U.S. Utility patent application Ser. No. 15/801,259, which was previously incorporated by reference herein.

FIGS. 7G to 7I depict the dual chamber safe injection system (100) in a third step of the method for sequential injection (side view, longitudinal cross-sectional view, detailed longitudinal cross-sectional view) with the system (100) at the end of the first injection configuration and the beginning of the second injection configuration. In the third step depicted in FIGS. 7G to 7I, the distal stopper member (36) has been advanced to a distal end of the syringe body (34), thereby collapsing the distal chamber (42, see FIGS. 7D to 7F) and ejecting substantially all of the first liquid (252, see FIGS. 7D to 7F) previously contained therein. The distal stopper member (36) effectively obstructs the middle opening (80) by separating it from the second liquid (254) in the proximal chamber (40).

As shown in FIG. 7I, the portion of the needle joining member (83) having the proximal openings (85) has passed through the distal stopper member (36) and entered the proximal chamber (40). Accordingly, the proximal chamber (40) is no longer close because it is open through the proximal openings (85). This places the system (100) in the second injection configuration. A distance between the most distal proximal opening (85) and the distal end of the syringe body (34) is substantially equal to a length of the distal stopper member (36). As such, when the distal stopper member (36) is inserted to the distal end of the syringe body (34), the proximal openings (85) are disposed in the proximal chamber (40).

Figure 7L:
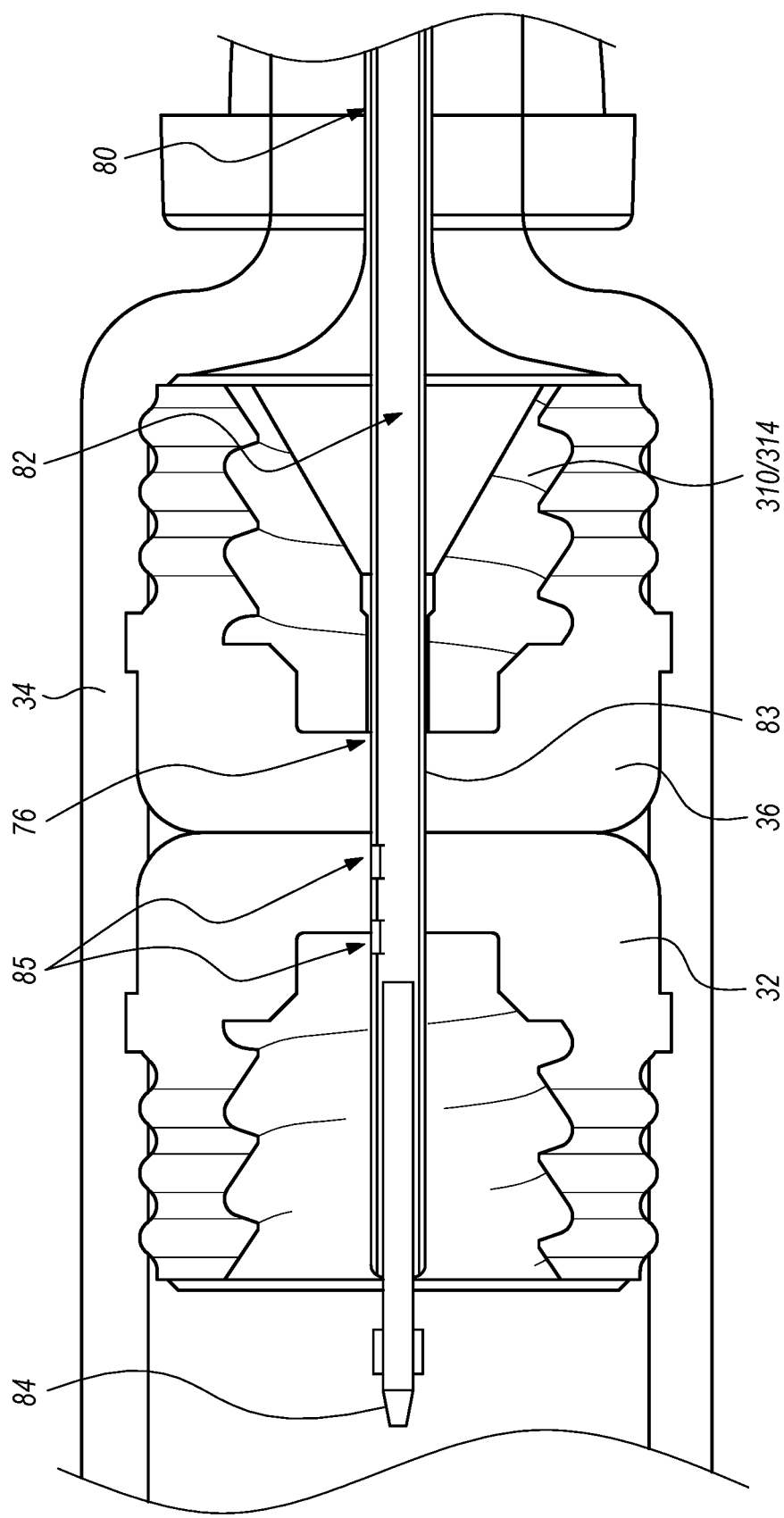

FIGS. 7J to 7L depict the dual chamber safe injection system (100) in a fourth step of the method for sequential injection (side view, longitudinal cross-sectional view, detailed longitudinal cross-sectional view) with the system (100) at the end of the second injection configuration. In the fourth step depicted in FIGS. 7J to 7L, the proximal stopper member (36) has been advanced to a proximal end of distal stopper member (36), which remains at a distal end of the syringe body (34), thereby collapsing the proximal chamber (40, see FIGS. 7G to 7I) and ejecting substantially all of the second liquid (254, see FIGS. 7G to 7I) previously contained therein. At the end of the fourth step as depicted in FIGS. 7J to 7L, the proximal end (84) has penetrated both the proximal and distal stopper members (32, 36), and has coupled with a coupling feature in the plunger rod for retraction of the needle spine assembly (76) at least partially into the plunger rod after the injection has been given to the patient as described in U.S. Utility patent application Ser. No. 15/801,259, which was previously incorporated by reference herein. In some embodiments, the system (100) retracts the needle spine assembly (76) to a position where the distal tip (48) thereof is disposed in the syringe body (34).

Exemplary Prefilled Dual Chamber Serial and Safe Injection Systems

Figure 8A:
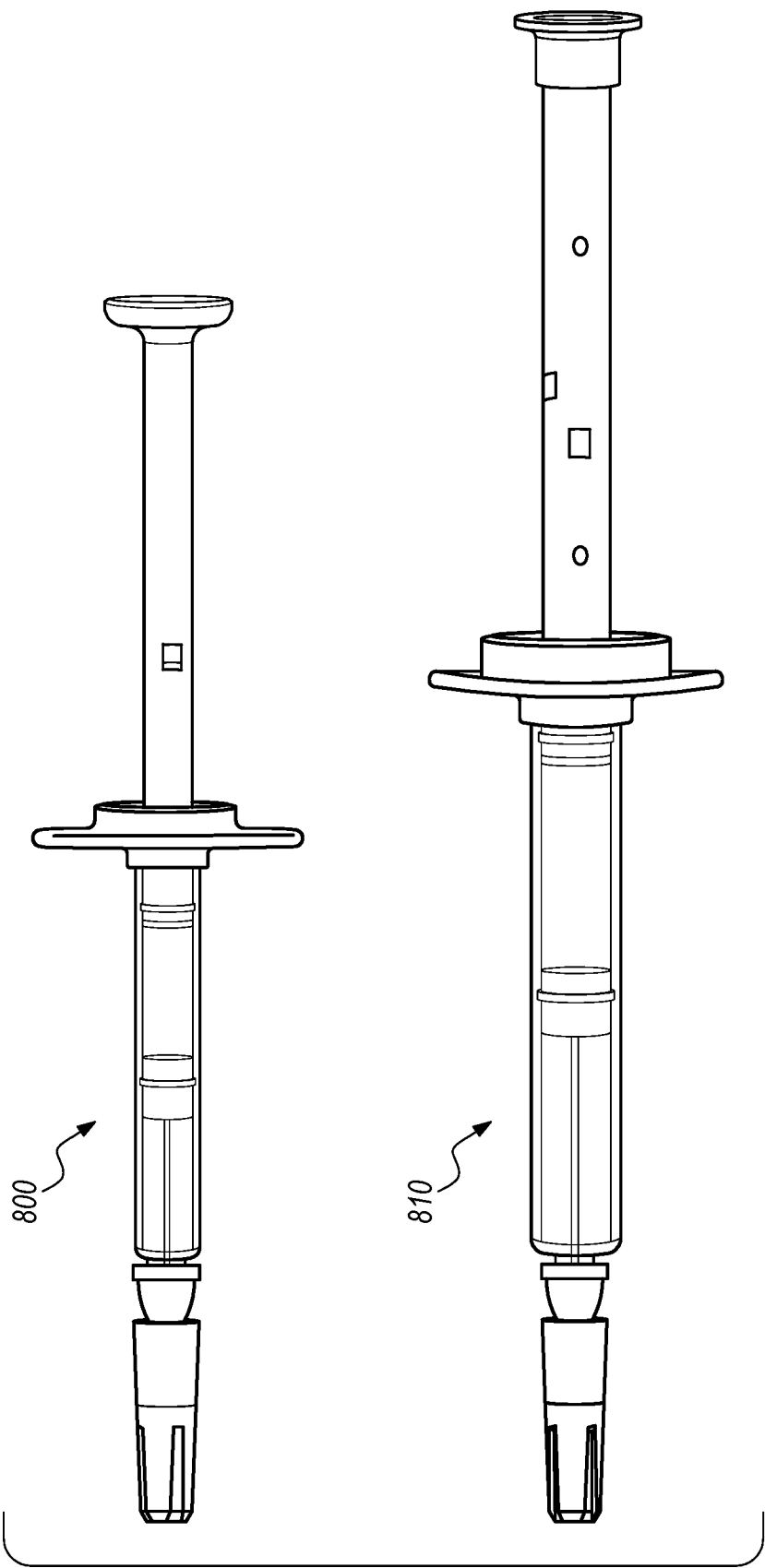
FIGS. 8A to 8C illustrate various aspects of syringe based dual chamber safe injection systems according to two embodiments.
Figure 8B:
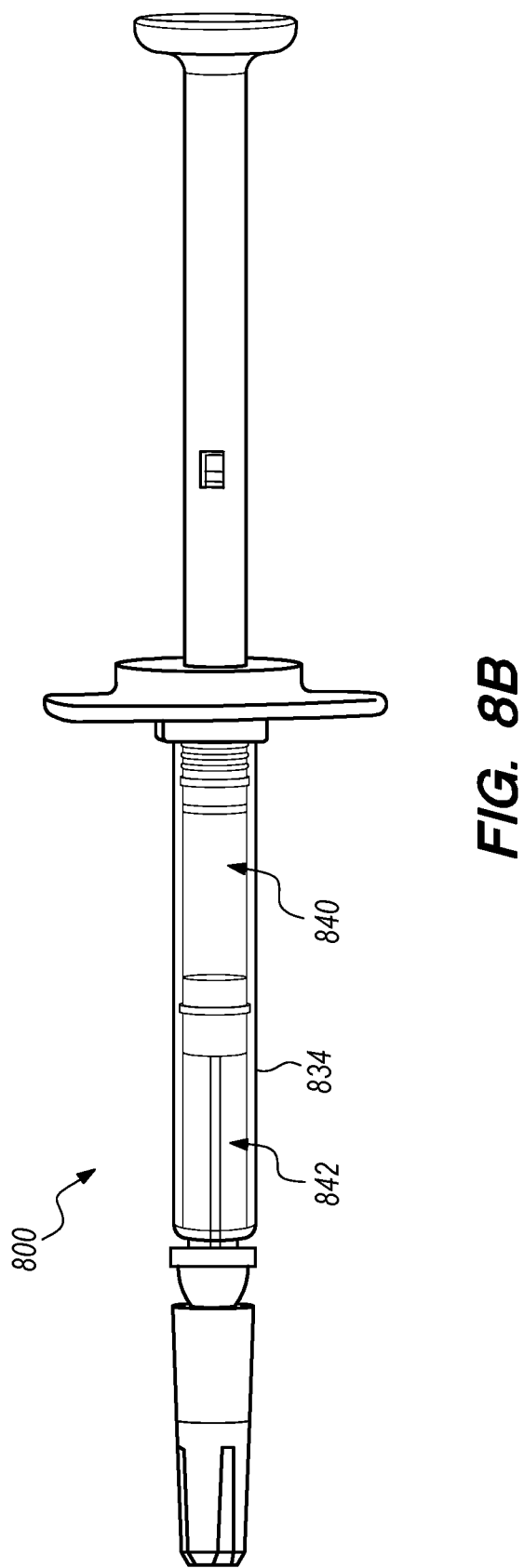
Figure 8C:
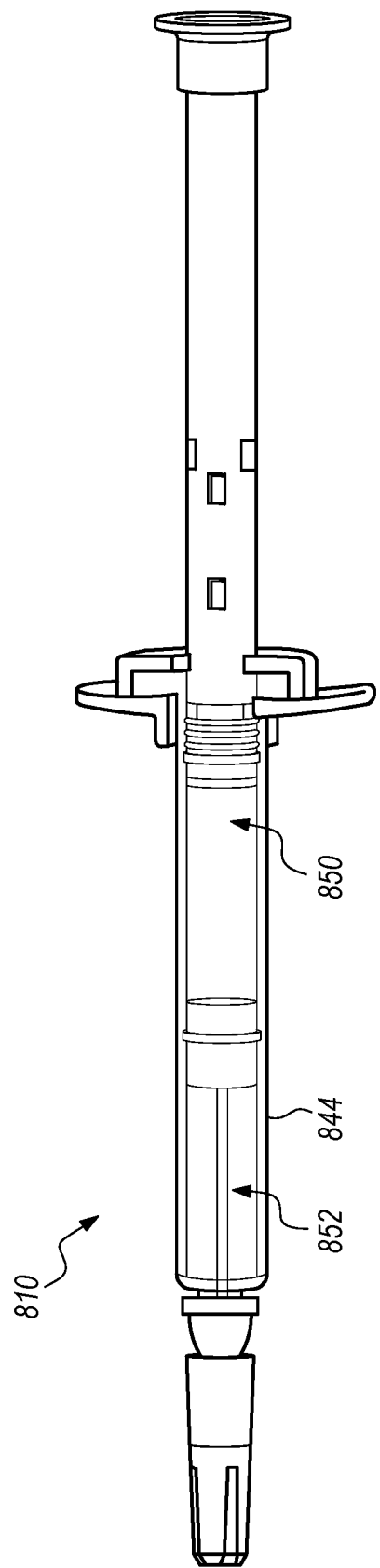

FIGS. 8A to 8C depict dual chamber safe injection systems (800, 810) according to two embodiments. The first system (800) has a total injection volume of 1 mL. The second system (810) has a total injection volume of 3 mL. The first system (800) uses a long glass syringe (834) with a total volume of approximately 1 mL, as shown in FIG. 8B. Each of the proximal and distal chambers (840, 842) in the first system (800) has a maximum capacity of approximately 0.5 mL.

The second system (810) uses a standard glass syringe (844) with a total volume of approximately 3 mL, as shown in FIG. 8C. Each of the proximal and distal chambers (850, 852) in the second system (810) has a maximum capacity of approximately 1.5 mL.

Figure 9A:
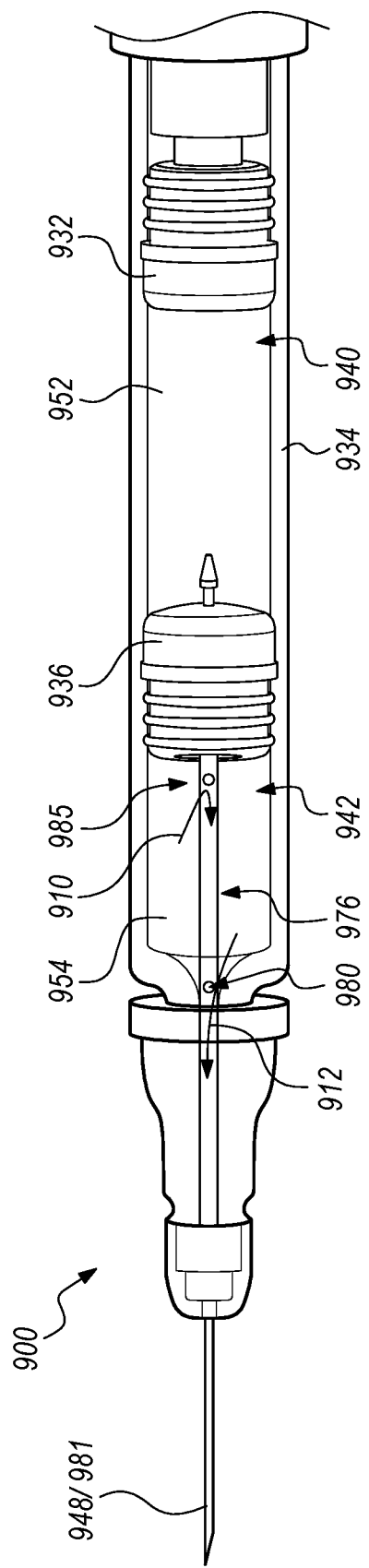
FIGS. 9A to 10B illustrate various aspects of syringe based dual chamber safe injection systems during steps in methods for serially injecting liquids using same according to some embodiments.
Figure 9B:
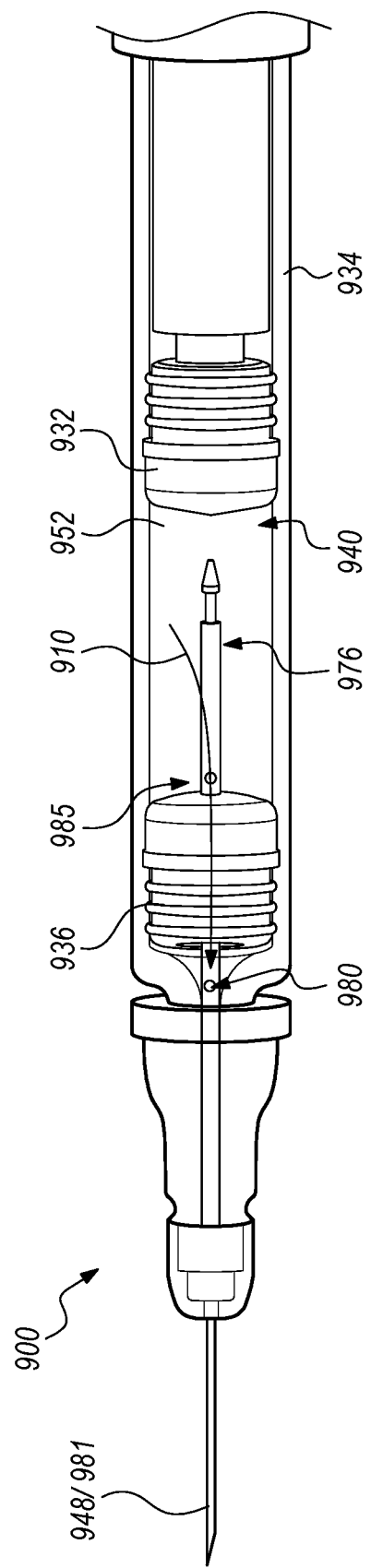
Figure 9C:
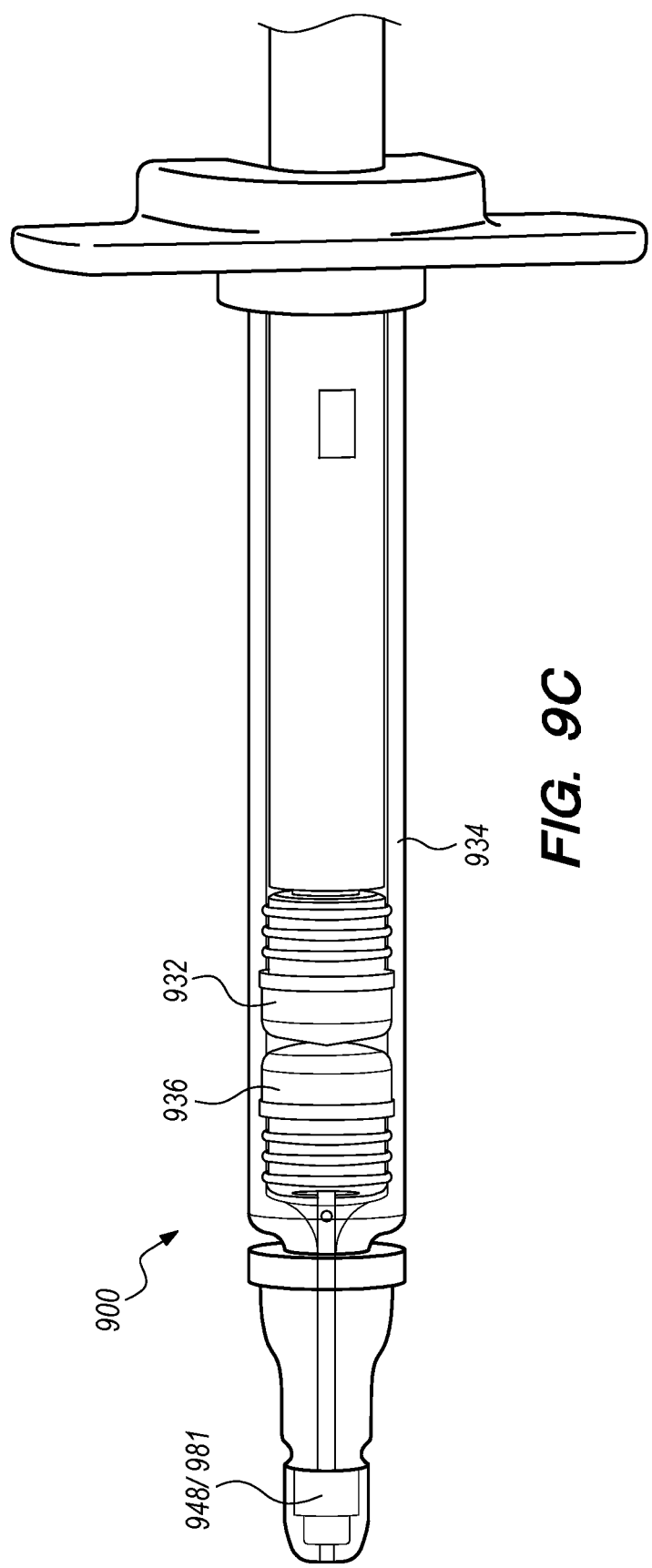

FIGS. 9A to 9C depict a prefilled dual chamber safe injection system (900) during various steps of sequential injection according to one embodiment. In the sequential injection step depicted in FIG. 9A, the system (900) is in the first injection configuration described above. In the first injection configuration, the proximal and distal stopper members (932, 936), the needle spine assembly (976), and the syringe body (934) are positioned such that, the proximal opening (985) is disposed in the distal chamber (942) and the proximal chamber (940) is closed. Accordingly, the first liquid (952) in the distal chamber (942) can exit the system (900) via one of two fluid paths (910, 912) that include the proximal and middle openings (985, 980), respectively. In the first configuration, the second liquid (952) cannot exit the system (900). Instead, the incompressible second liquid (952) transfers force applied to the proximal stopper member (932) to the distal stopper member (936).

FIG. 9B depicts the system (900) is in the second injection configuration described above in which the distal stopper member (936) has moved to a distal end of the syringe body (934) thereby collapsing the distal chamber (942, see FIG. 9A) and ejecting substantially all of the first liquid (952, see FIG. 9A) from the system (900). In the second injection configuration, the proximal and distal stopper members (932, 936), the needle spine assembly (976), and the syringe body (934) are positioned such that, the proximal opening (985) is disposed in the proximal chamber (940) thereby opening the proximal chamber (940). Accordingly, the second liquid (954) in the proximal chamber (940) can exit the system (900) via a fluid path (910) that includes the proximal openings (985). In the second configuration, distal stopper member (936) effectively obstructs the middle opening (980) by separating it from the second liquid (954) in the proximal chamber (940).

FIG. 9C depicts the system (900) after the proximal stopper member (932) has been moved distally until it abuts a proximal end of the distal stopper member (936). This collapses the proximal chamber (940, see FIG. 9B) and ejecting substantially all of the second liquid (954, see FIG. 9B) from the system (900). After the first and second liquids (952, 954, see FIG. 9A) have been ejected from the system (900), a slight further distal movement of the plunger member moves the needle spine assembly (976) distally, thereby releasing a needle latch to allow proximal retraction of the needle (976) such that the distal tip (948) is disposed inside of the syringe body (934) into a protected state. Release of the needle latch retraction of the needle (976) is further described in U.S. Utility patent application Ser. No. 15/801,259, which was previously incorporated by reference herein.

Figure 10A:
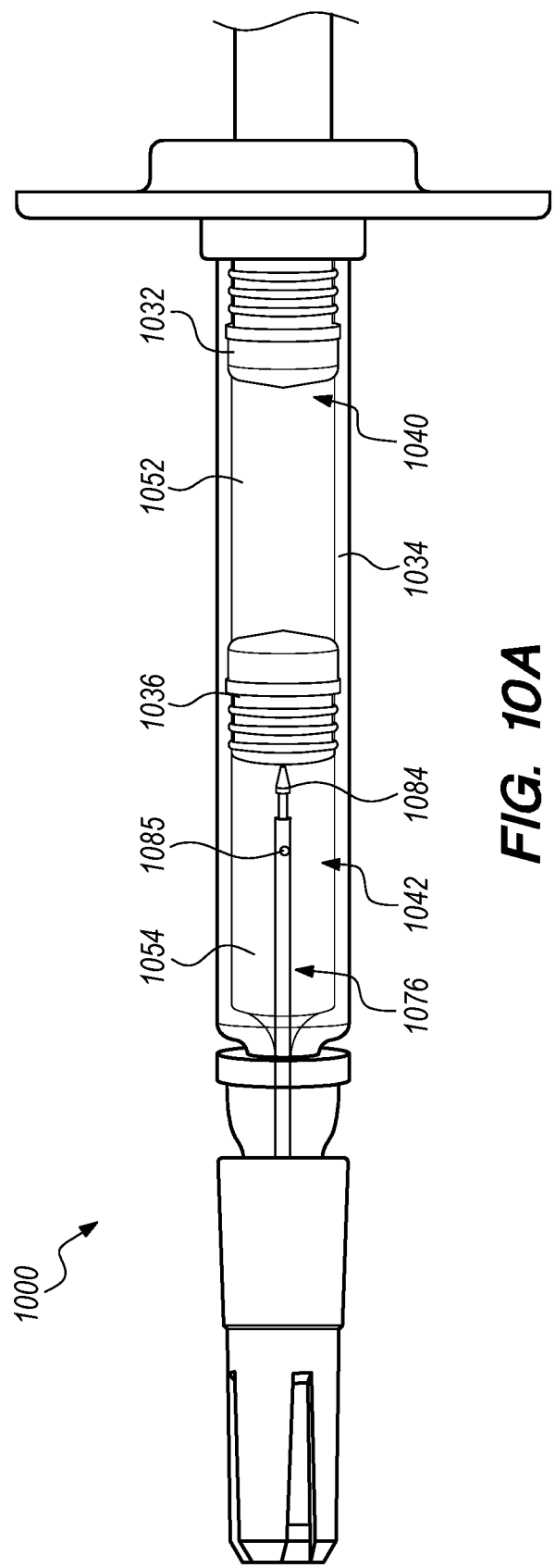
Figure 10B:
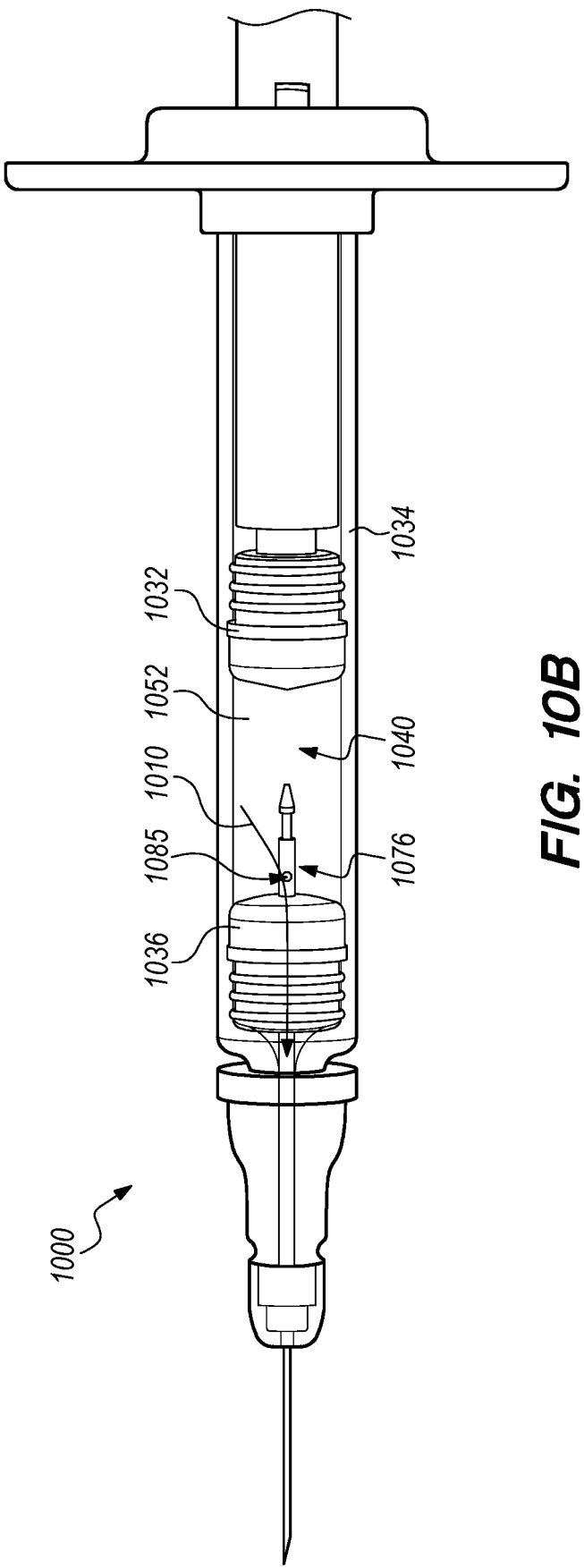

FIGS. 10A and 10B depict a prefilled dual chamber safe injection system (1000) during various steps of sequential injection according to another embodiment. The difference between the system (1000) depicted in FIGS. 10A and 10B and the system (900) depicted in FIGS. 9A to 9C is that the needle spine assembly (1076) is sized and positioned relative to the proximal and distal stopper members (1032, 1036) and the syringe body (1034) such that the proximal end (1084) of the needle (1076) is disposed in the distal chamber (1042) in the storage/transport configuration depicted in FIG. 10A. In this embodiment, a funnel guides the proximal end (1084) of the needle (1076) through the distal stopper member (1036) as described in U.S. Utility patent application Ser. No. 15/801,259, which was previously incorporated by reference herein.

FIG. 10B shows that in the second injection configuration, the proximal opening (1085) is disposed in the proximal chamber (1040) thereby opening the proximal chamber (1040). A distance between the proximal opening (1085) and the distal end of the syringe body (1034) is substantially equal to a length of the distal stopper member (1036). As such, when the distal stopper member (1036) is inserted to the distal end of the syringe body (1034), the proximal opening (1085) is disposed in the proximal chamber (1040). Use of a shorter needle spine assembly (1076) allows for retraction of the needle spine assembly (1076) into a shorter plunger member as described in U.S. Utility patent application Ser. No. 15/801,259, which was previously incorporated by reference herein.

Exemplary Distal Bushings with Detents in Dual Chamber Safe Injection Systems

Figure 11B:
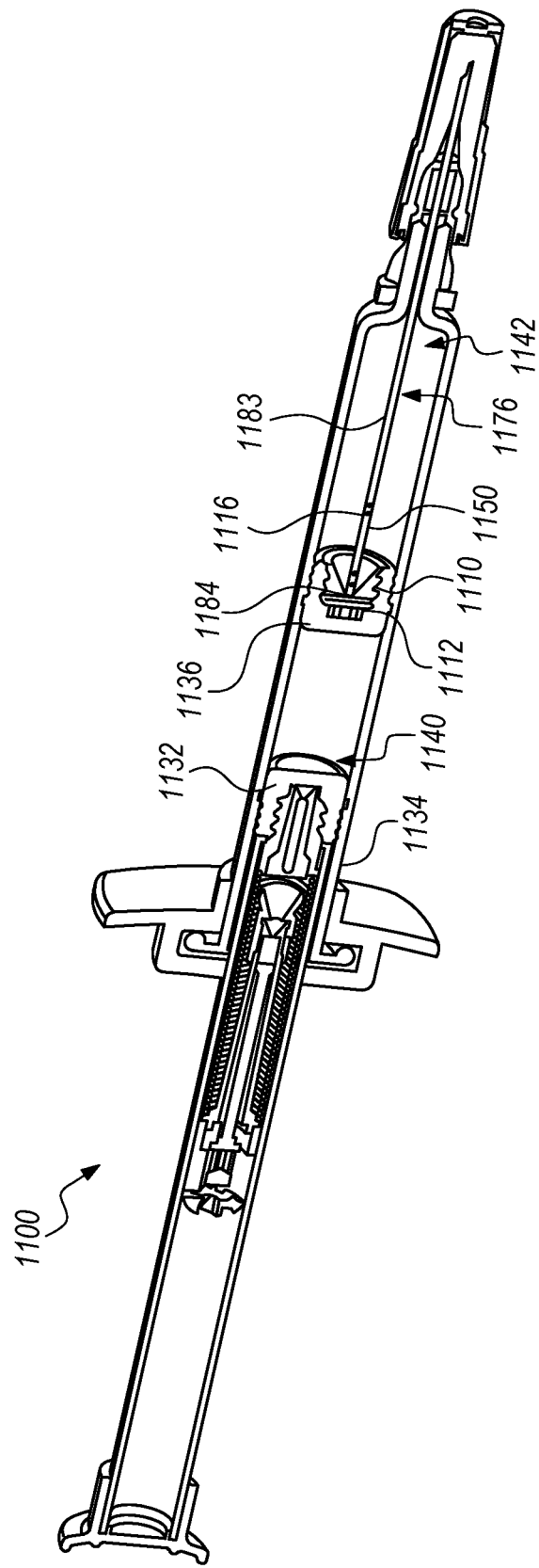

FIGS. 11A and 11B depict a prefilled dual chamber safe injection system (1100) according to some embodiments. The system (1100) is different from the other prefilled dual chamber safe injection systems depicted and described above in that the distal stopper member (1136) in that it is not a serial injection system, but rather a mix and inject system such as those described in U.S. Utility patent application Ser. No. 15/801,259, which was previously incorporated by reference herein. In these systems, a liquid is transferred from a proximal chamber (1140) to a distal chamber (1142) to rehydrate a lyophilized component (not shown) in the distal chamber (1142) before the rehydrated mixture is injected into a patient. Various aspects and benefits of such systems are described in U.S. Utility patent application Ser. No. 15/801,259, which was previously incorporated by reference herein.

The system (1100) includes a stopper bushing (1110) having a detent (1112) disposed therein. The detent (1112) is configured to interact with the sharpened proximal end (1184) of the needle spine assembly (1176) and a shoulder (1116) at the junction between the needle proximal end (1150) and the needle joining member (1183) to provide resistance to distal movement of the distal stopper member (1136) relative to the needle spine assembly (1176). The interaction between the detent (1112) and the proximal end (1184) maintains the distal stopper member (1136) in a ready to use position during storage and transport, such as the configuration depicted in FIGS. 11A and 11B. This interaction will maintain the position of the distal stopper member (1136) even with a vacuum or partial vacuum (e.g. for the lyophilized component) in the distal chamber (1142). Without the detent (1112) and with a vacuum in the distal chamber (1142), the distal stopper member (1136) will eventually move distally relative to the needle spine assembly (1176) and be penetrated thereby. This would render the system unusable for serial injection.

The interaction between the detent (1112) and the shoulder (1116) maintains the distal stopper member (1136) in a transfer position during transfer of the liquid from the proximal chamber (1140) to the distal chamber (1142). This interaction allows the user to apply a wider range of force to the plunger member to transfer the liquid while minimizing the risk of premature movement of the distal stopper member (1136).

Figure 12A:
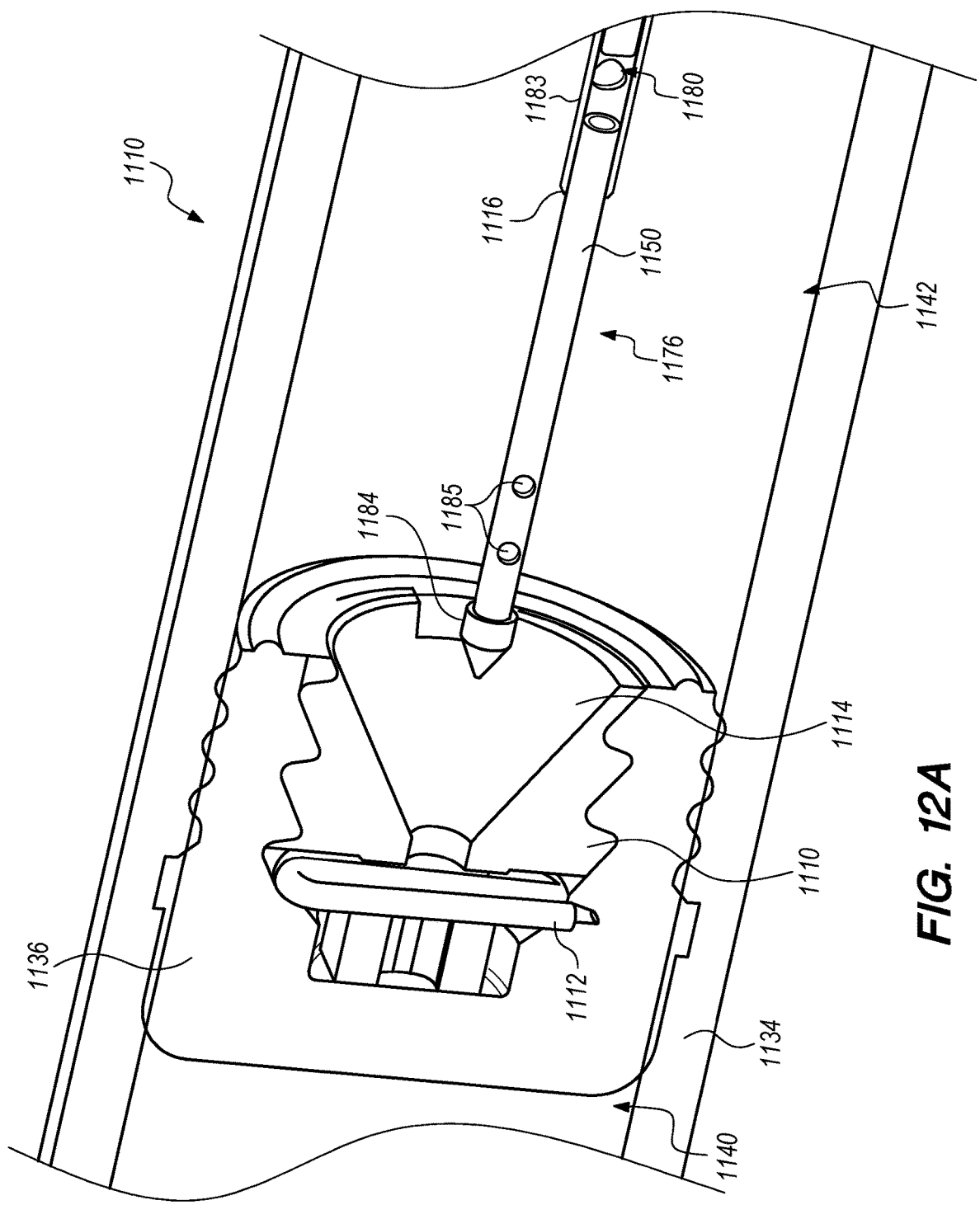
FIGS. 12A to 12C illustrate various aspects of a distal stopper member having a stopper bushing with a detent for use with syringe based dual chamber safe injection systems during steps in methods for serially injecting liquids using same according to some embodiments.
Figure 12B:
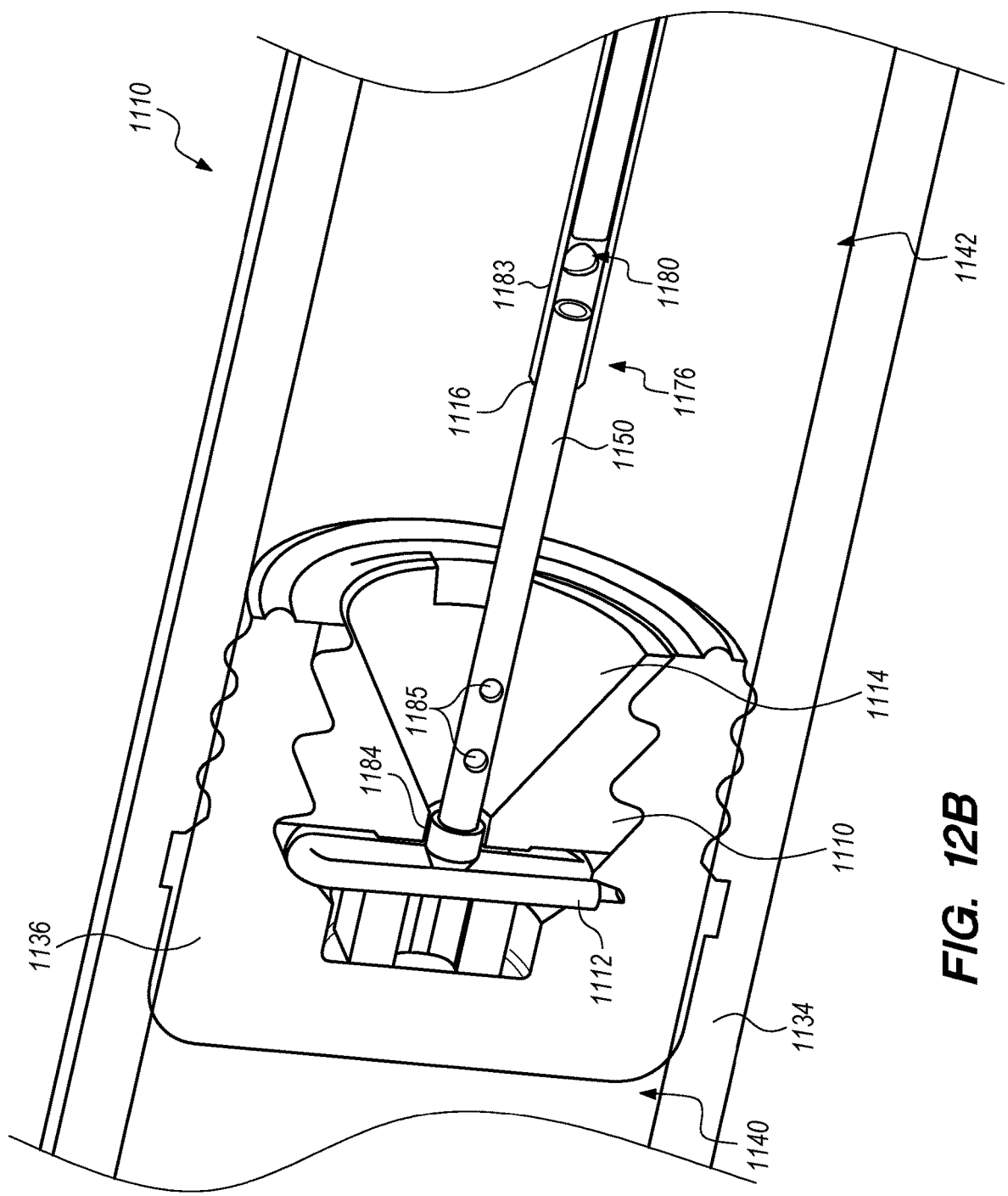
Figure 12C:
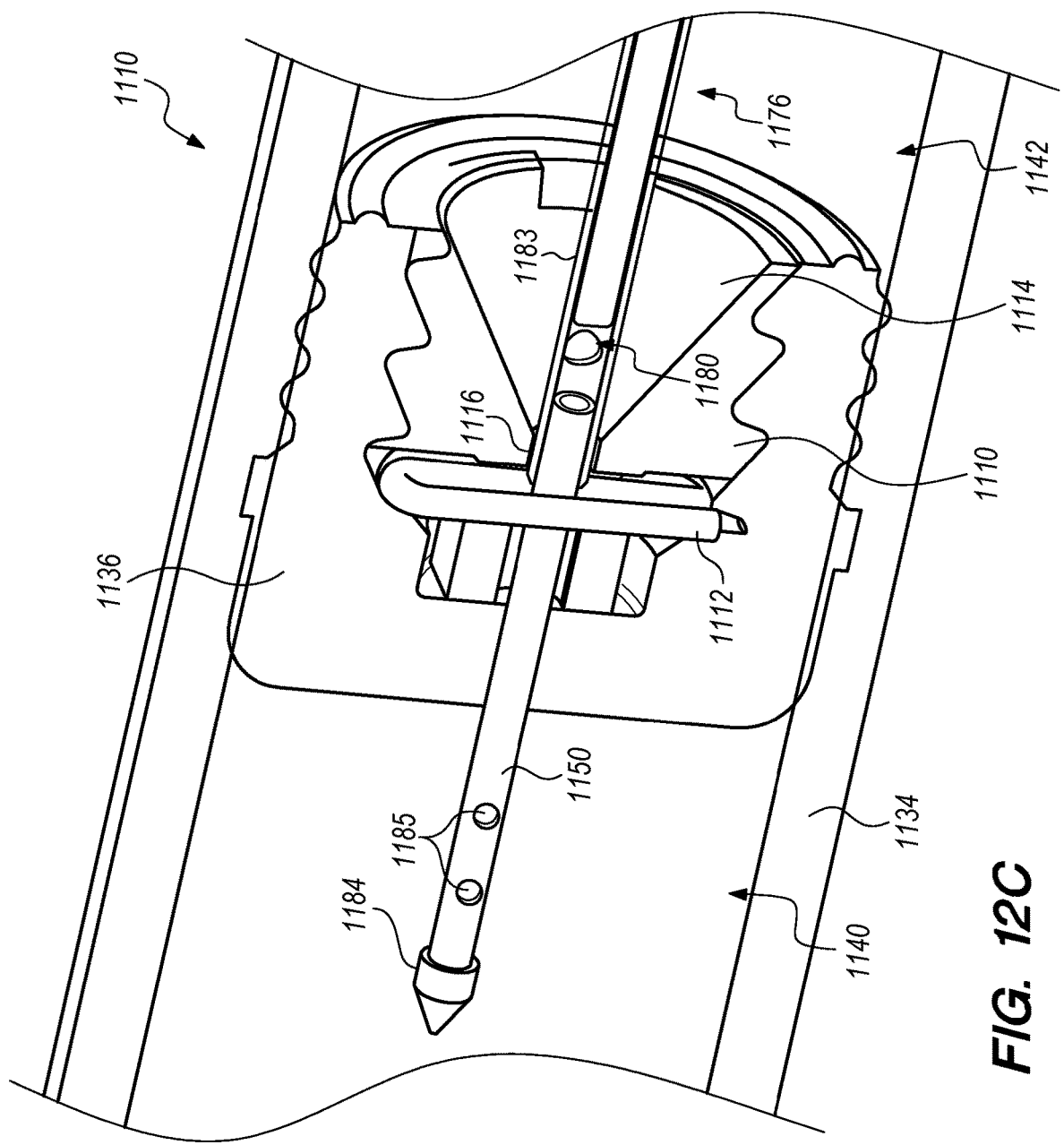

FIGS. 12A to 12C depict the interactions between the detent (1112) and the sharpened proximal end (1184) of the needle spine assembly (1176) and a shoulder (1116) on the needle spine assembly (1176) in the prefilled dual chamber safe injection system (1100) depicted in FIGS. 11A and 11B. FIG. 12A shows a distal stopper member (1136) having a stopper bushing (1110) with a detent (1112) and defining an alignment funnel (1114). In FIG. 12A the alignment funnel (1114) guides a proximal end (1184) of the needle spine assembly (1176) into positioned adjacent the detent (1112).

FIG. 12B shows the storage/transport configuration of the system (1100). In this configuration, the sharpened proximal end (1184) of the needle spine assembly (1176) is disposed adjacent to and partially within the detent (1112). Various properties of the proximal end (1184) and the detent (1112) (e.g., geometric, material, etc.) can be modified to modulate the force required to push the proximal end (1184) past the detent (1112). These properties are described in detail below. In one embodiment, the force required to push the proximal end (1184) past the detent (1112) is from about 2 pounds to about 5 pounds. As described above, even with a vacuum or partial vacuum in the distal chamber (1142) urging the distal stopper member (1136) in a distal direction, the interaction between the proximal end (1184) and the detent (1112) prevents premature movement of the distal stopper member (1136) relative to the needle spine assembly (1176). This allows the prefilled dual chamber system (1100) to be stored while minimizing the risk of premature movement of the distal stopper member (1136), which can render the system (1100) unusable.

FIG. 12C shows the transfer configuration of the system (1100). In this configuration, the distal stopper member (1136) has been pushed distally past the sharpened proximal end (1184) of the needle spine assembly (1176) by user provided force on the plunger member. The proximal openings (1185) are disposed in the proximal chamber (1140) allowing liquid to transfer from the proximal chamber (1140) to the distal chamber (1142). While a vacuum in the distal chamber (1142) withdraw the liquid out of the proximal chamber (1140), user generated force applied to the proximal stopper member (1132) via the plunger member will assist the liquid transfer. In this configuration, a shoulder (1116) on the needle spine assembly (1176) is disposed adjacent to the detent (1112). Various properties of the shoulder (1116) and the detent (1112) (e.g., geometric, material, etc.) can be modified to modulate the force required to push the shoulder (1116) past the detent (1112). These properties are described in detail below. In one embodiment, the force required to push the shoulder (1116) past the detent (1112) is from about 2 pounds to about 5 pounds. The shoulder is formed at the joint between the needle proximal end (1150) and the needle joining member (1183). While the interaction between the shoulder (1116) and the detent (1112) holds the system (1100) in the transfer configuration depicted in FIG. 12C, pressure applied to the plunger member will aid liquid transfer from the proximal chamber (1140) to the distal chamber (1142). The force required to overcome the interference between the shoulder (1116) and the detent (1112) provides more latitude for a user to press the plunger member to aid in the liquid transfer. This increases the chances of complete liquid transfer.

Figure 13A:
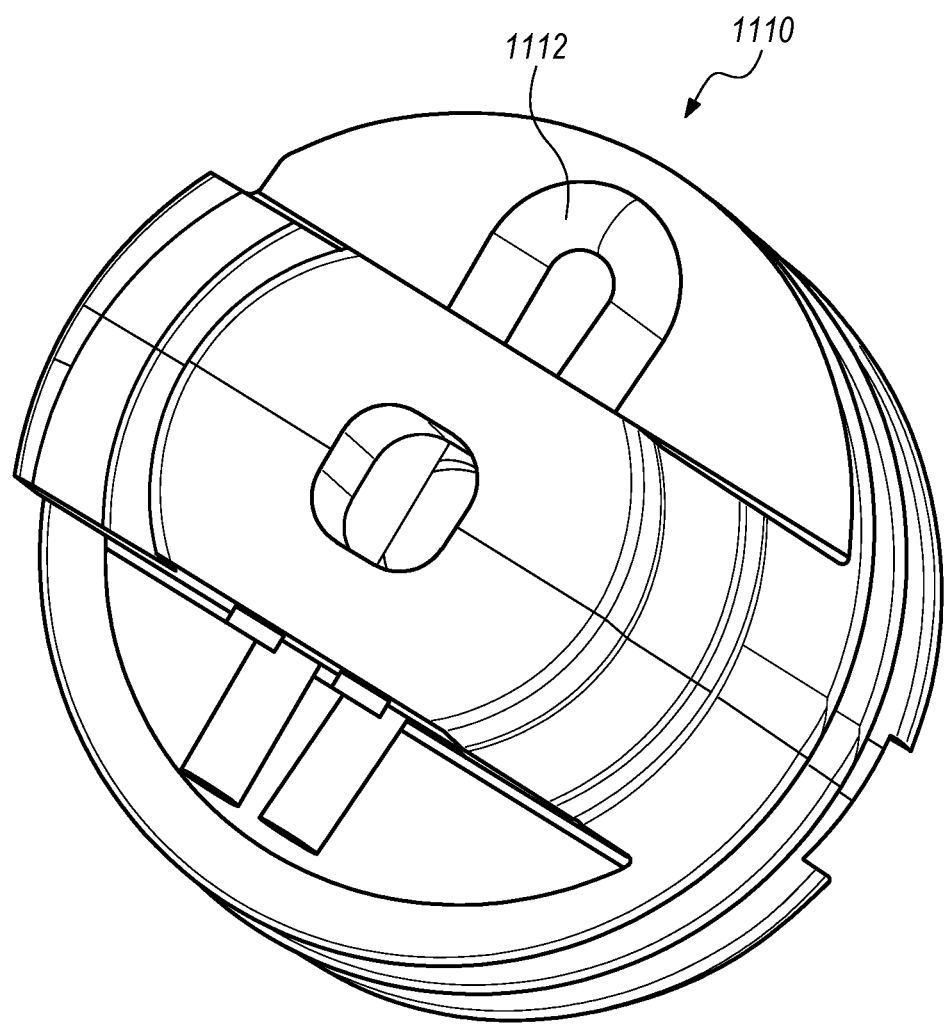
FIGS. 13A to 13C illustrate various aspects of a stopper member bushing with a detent for use with syringe based dual chamber safe injection systems according to some embodiments.
Figure 13B:
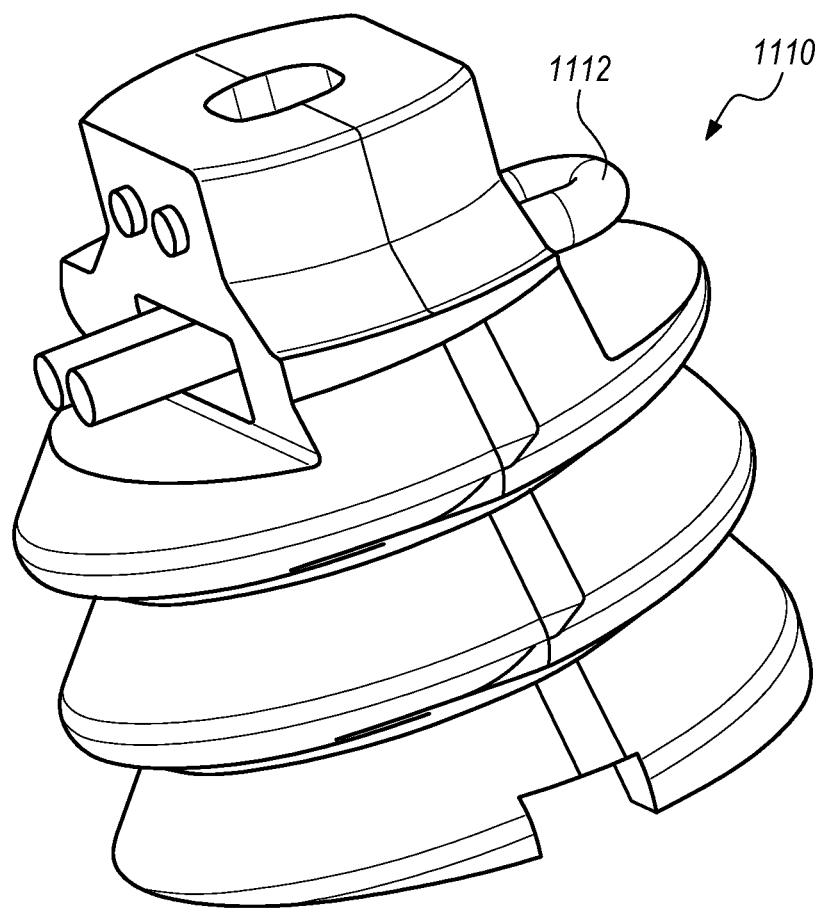
Figure 13C:
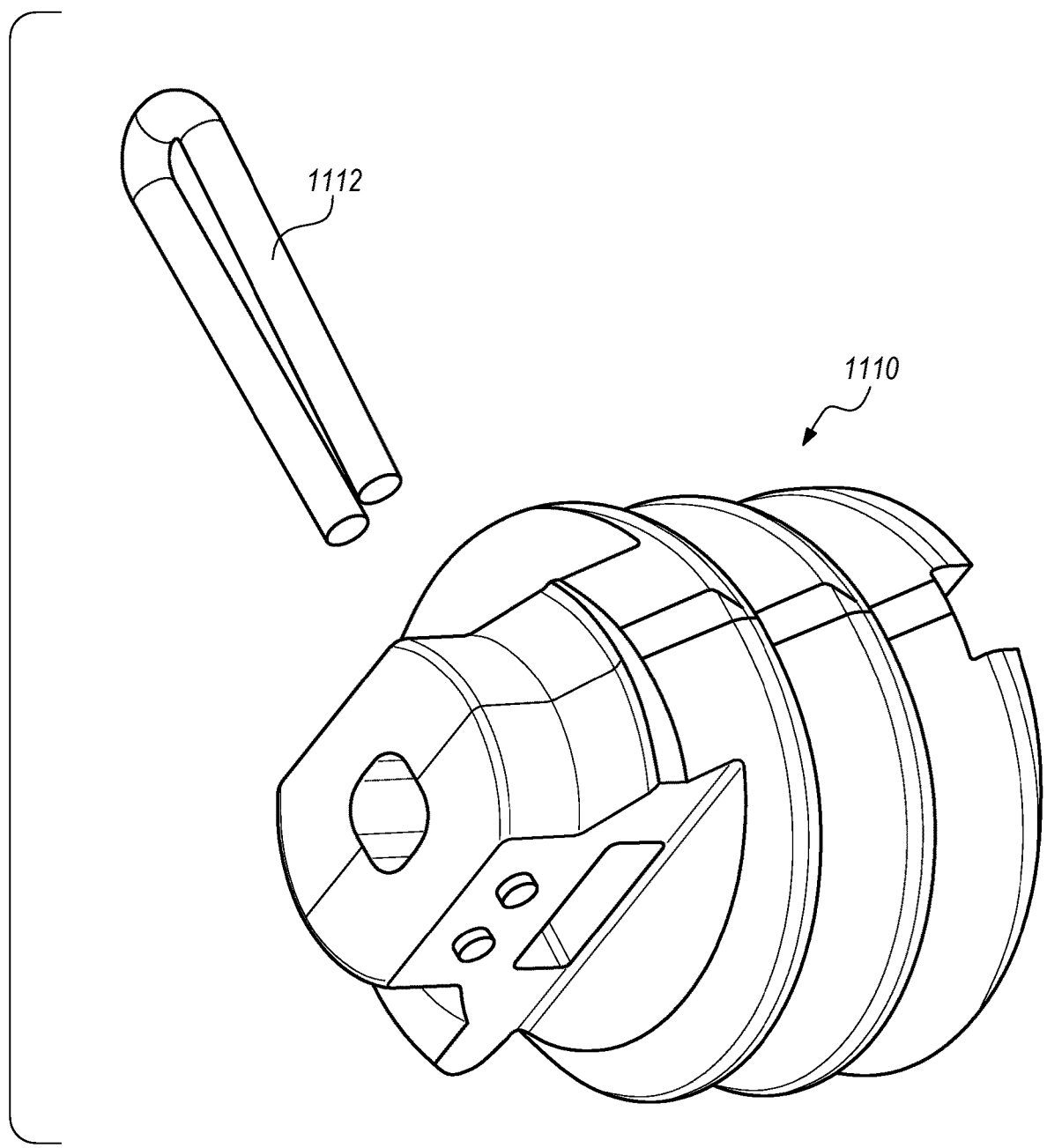

FIGS. 13A to 13C depict a stopper bushing (1110) for use with the prefilled dual chamber safe injection system (1100) depicted in FIGS. 11A and 11B. The stopper bushing (1110) has a detent (1112) inserted into a slot in the bushing (1110) along an axis orthogonal to the longitudinal axis of the needle spine assembly. As shown in FIG. 13C, the detent may be made of a bent wire having a "U" shape.

Figure 14A:
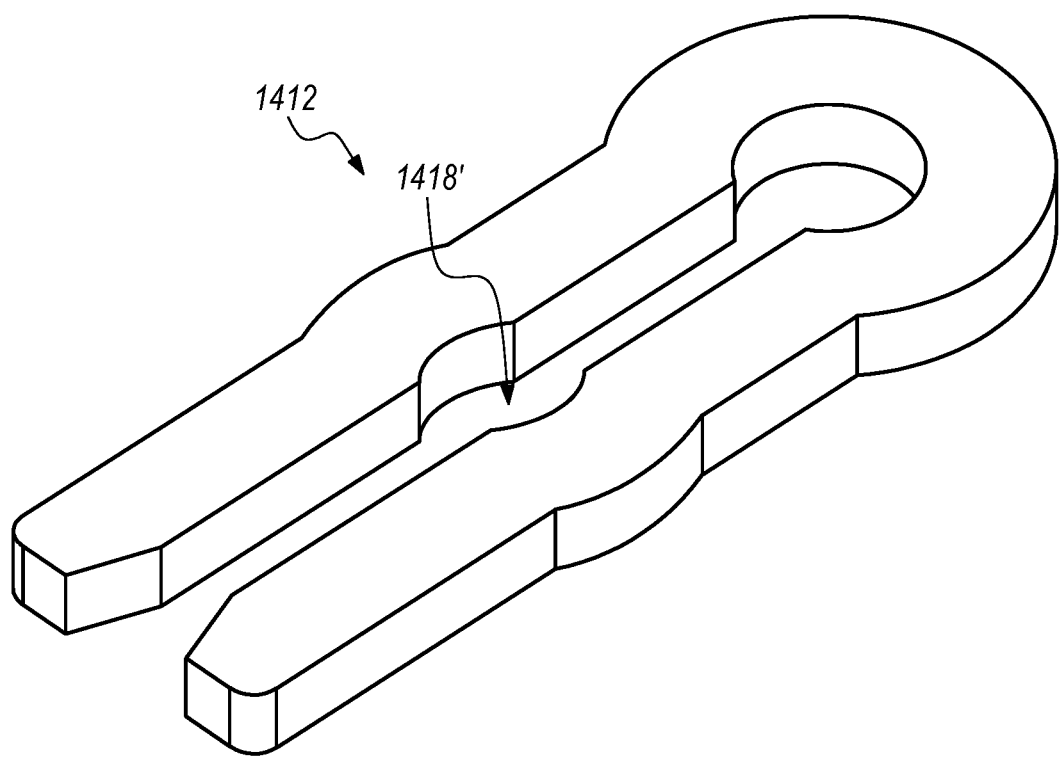
FIGS. 14A to 14C illustrate various aspects of a detent for use with a stopper member bushing for use with syringe based dual chamber safe injection systems according to some embodiments.
Figure 14B:
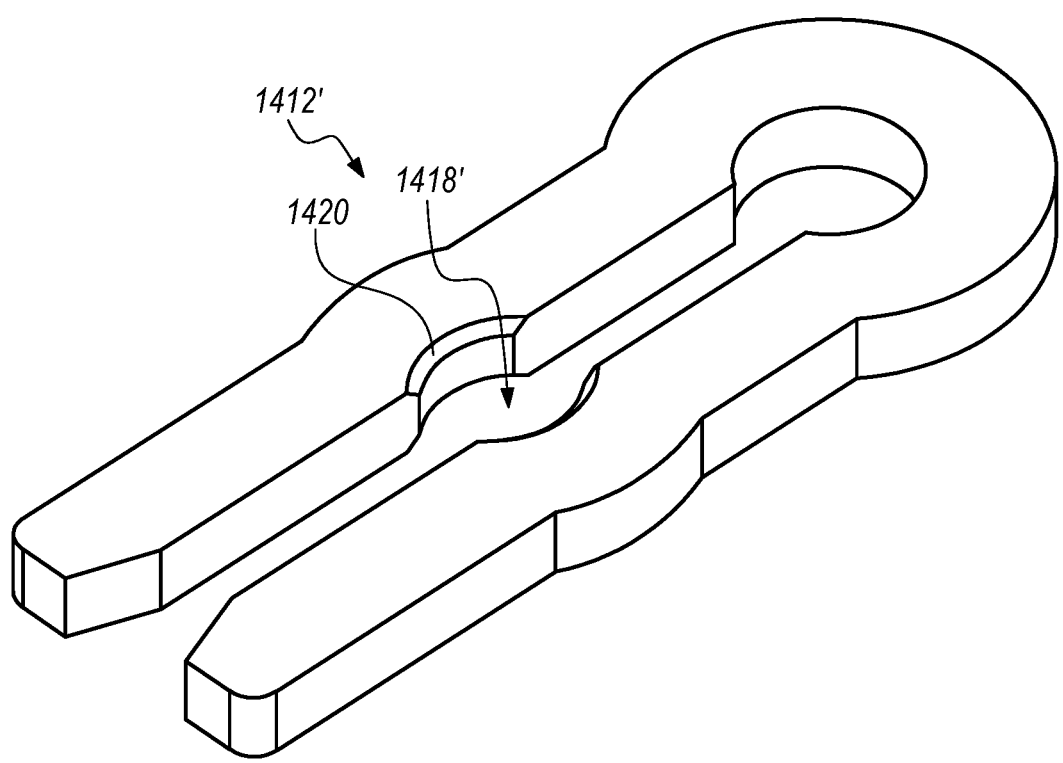
Figure 14C:
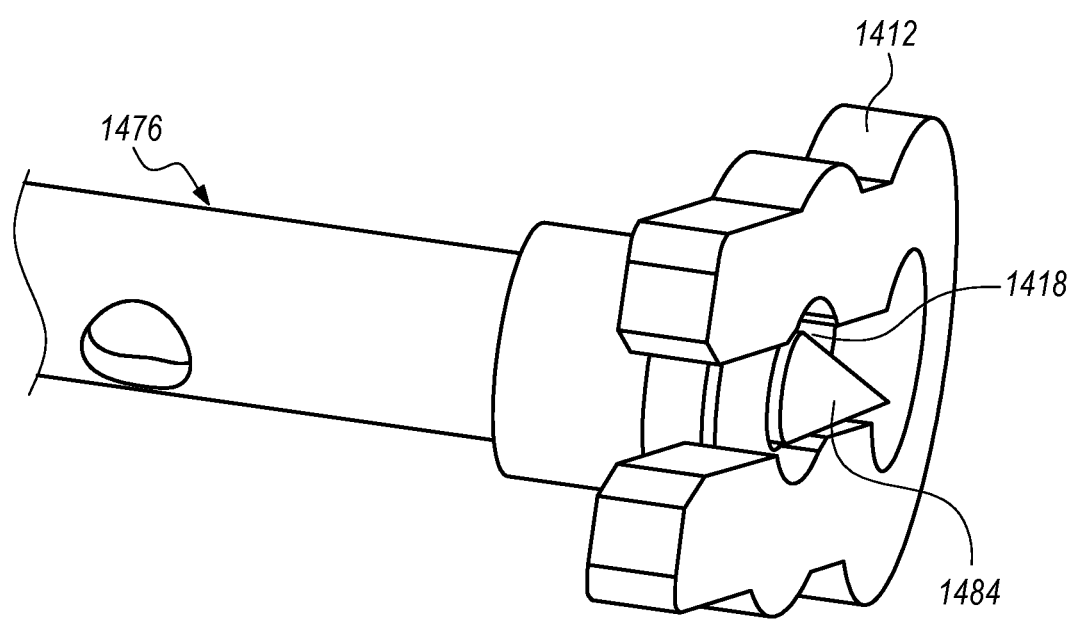

FIGS. 14A to 14C show detents (1412, 1412') for use with stopper bushings of prefilled dual chamber safe injection systems according to various embodiments. The detents (1412, 1412') are formed from a sheet of metallic material, and thus have a flat cross-section. The detents (1412, 1412') all have a "U" shape and include a notch (1418) configured to receive a round shape, such as those on sharpened proximal ends and shoulders of the needle spine assemblies. The detent (1412') depicted in FIG. 14B includes a chamfered/baffled penetration surface (1420) around a circumference of the notch (1418) on the side of the detent (1412') adjacent the sharpened proximal ends of the needle spine assemblies in the storage/transport configuration described above. The beveled penetration surface (1420) can be modified to modulate the amount of force required to penetrate the detent (1412').

FIG. 14C depicts the sharpened proximal end (1484) of a needle spine assembly (1476) disposed in the notch (1418) of a detent (1412), such as in a storage/transport configuration.

In one embodiment, the resistance force provided by the detent (1412) as it slides over a sharpened proximal end (1484) of a needle spine assembly (1476) is variable. The detent (1412) resist penetration by the proximal end (1484) during storage (e.g., for several years). With the application of a predetermined amount of force by the user, the proximal end (1484) slides through the detent (1412). Then, the resistance force to movement of the needle spine assembly (1476) through the detent (1412) is minimal until the detent (1410) the detent (1412) reaches the shoulder (1116, see FIG. 12C). When the detent (1412) abuts the shoulder, resistance force increases to reliably stop the progress of the detent (1412) (and distal stopper member) relative to the needle (1478). After liquid transfer described above, the user applies another predetermined amount of force to push the detent (1412) will over the shoulder. After the shoulder is cleared, the friction from the interaction of the detent (1412) and the needle (1476) is minimal to facilitate giving the injection and needle retraction.

The predetermined amount of force can be modulated to accommodate a combination of the system function requirements and the aesthetic impression on the user. If the activation force is too low, it may work, but be too difficult for the user to apply the force lightly enough, and the user may overshoot. If the force is too high, the user may find that it is "too hard" to activate the system. Fortunately, the predetermined amount of force can be "tuned" into a range by modifying various component characteristics.

Figure 15:
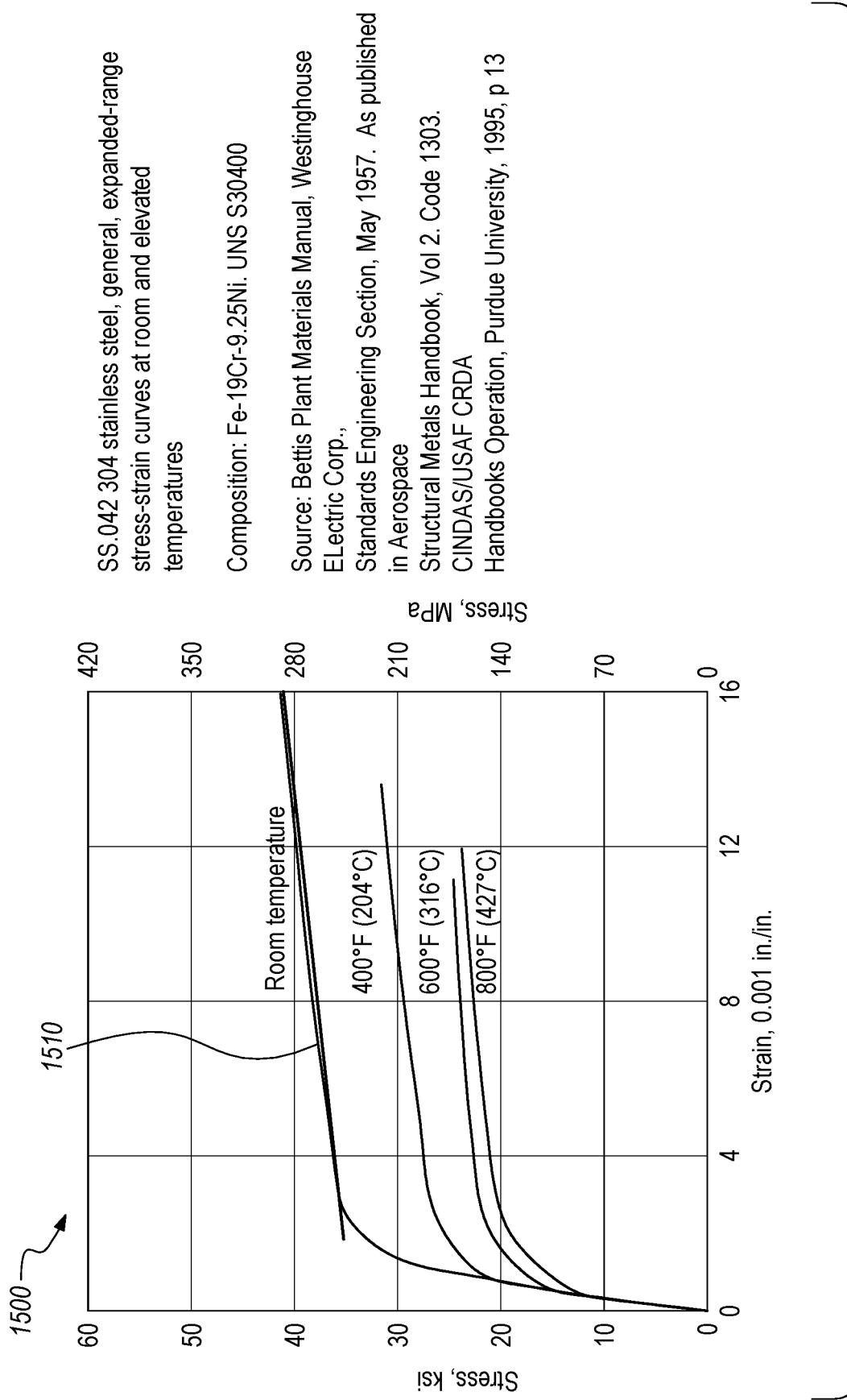
FIG. 15 is a graph plotting stress vs. strain for a material from which a detent for use with a stopper member bushing for use with syringe based dual chamber safe injection systems according to some embodiments can be made.

FIG. 15 depicts a graph (1500) of stress versus strain for stainless steel from which the detent may be made. Using annealed stainless steel places the detent material on the flat yield plateau (1510), which limits the gripping force of the detent after the proximal end or shoulder has moved passed the detent, because the detent has become permanently "bent" or yielded after it passes over the proximal end or shoulder. By selecting different materials, the elasticity of the detent relative to the deformation required for the proximal and/or shoulder to pass can be modified to modulate the force required to push these components past the detent.

Figure 16:
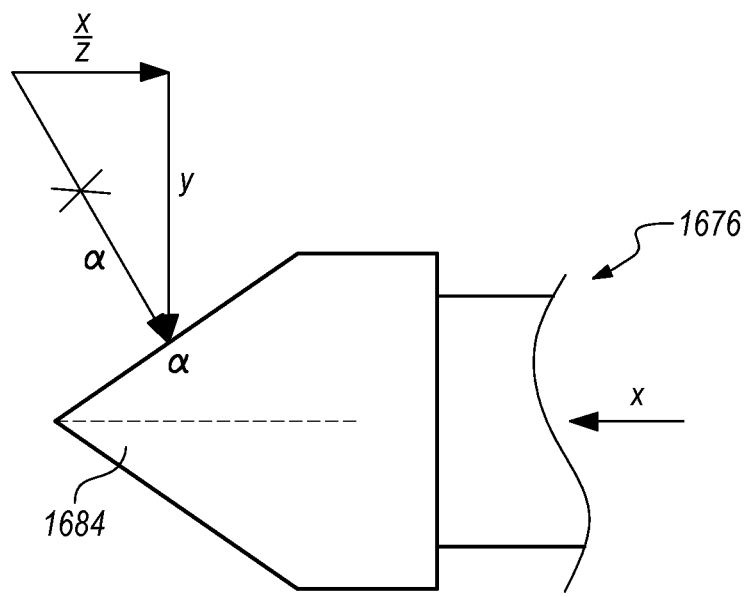
FIGS. 16 and 17 illustrate various harpoon and shoulder geometries for use with a stopper member bushing with a detent for use with syringe based dual chamber safe injection systems according to some embodiments.
Figure 17:
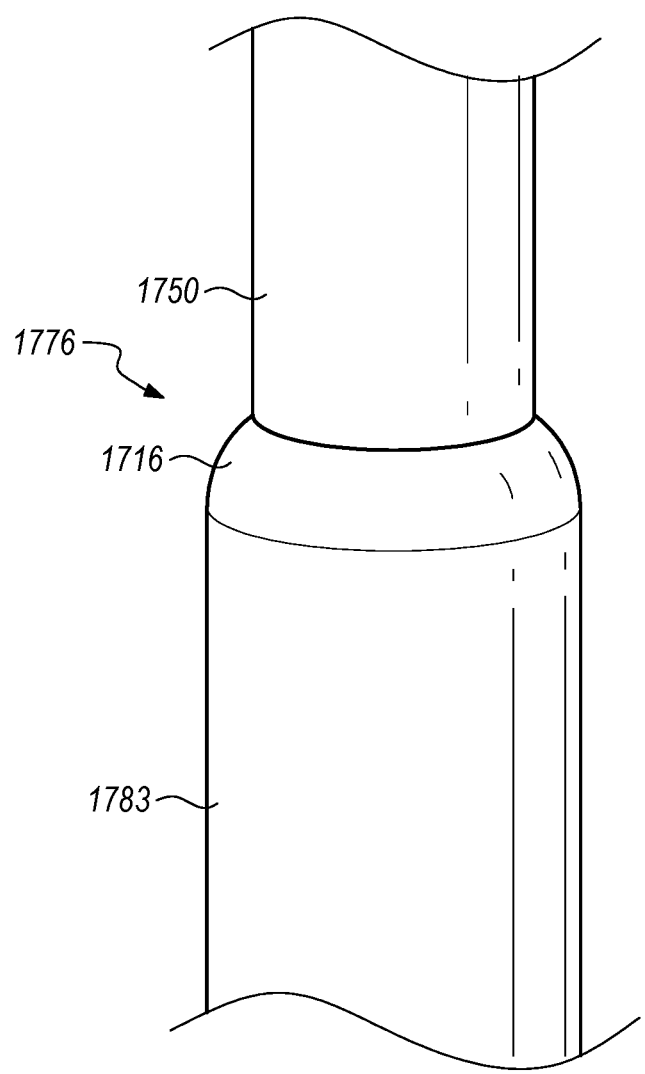

FIG. 16 depicts a geometry of a proximal end (1684) of a needle spine assembly (1676) and its effect on the force required to push the proximal end (1684) pass a detent. To fine tune the resistance forces passing over the arrowhead shaped proximal end (1684) and passing over the shoulder (1716, see FIG. 17), the ramp angles over each one can be independently adjusted as needed. Ignoring friction as an approximation, the effect of ramp angle on the resistance force (X) is shown in the equations in FIG. 17. Since the Tangent function can have values from zero to a very large number, theoretically, any force can be achieved. Adding friction will add more force to the value calculated by using the equations. Values of about 30 degrees for the arrowhead shaped proximal end (1684) and about 50 degrees for the shoulder (1716) provide resistance forces many users find acceptable.

Figure 18:
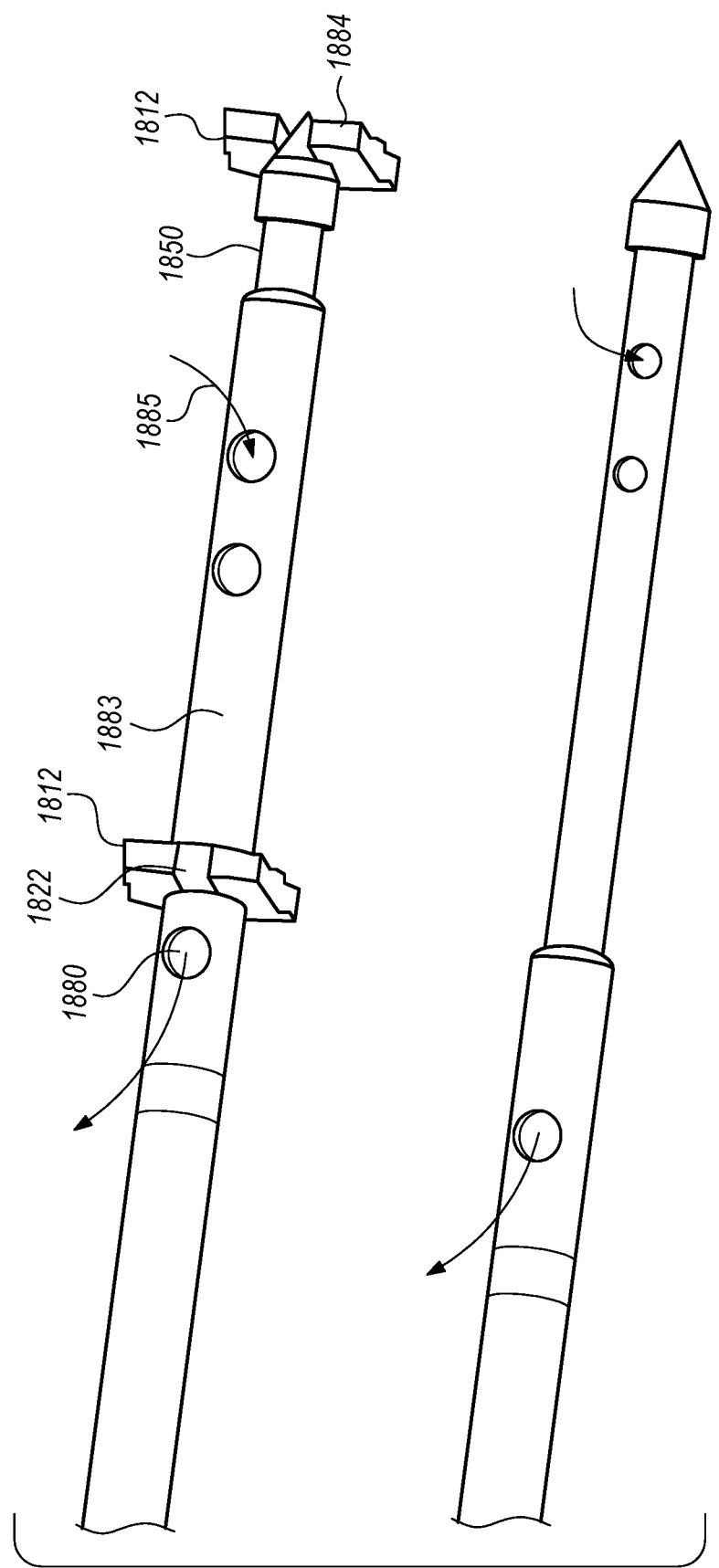
FIGS. 18 and 19 illustrate various aspects of needle spine assemblies of syringe based dual chamber safe injection systems according to some embodiments.
Figure 19:
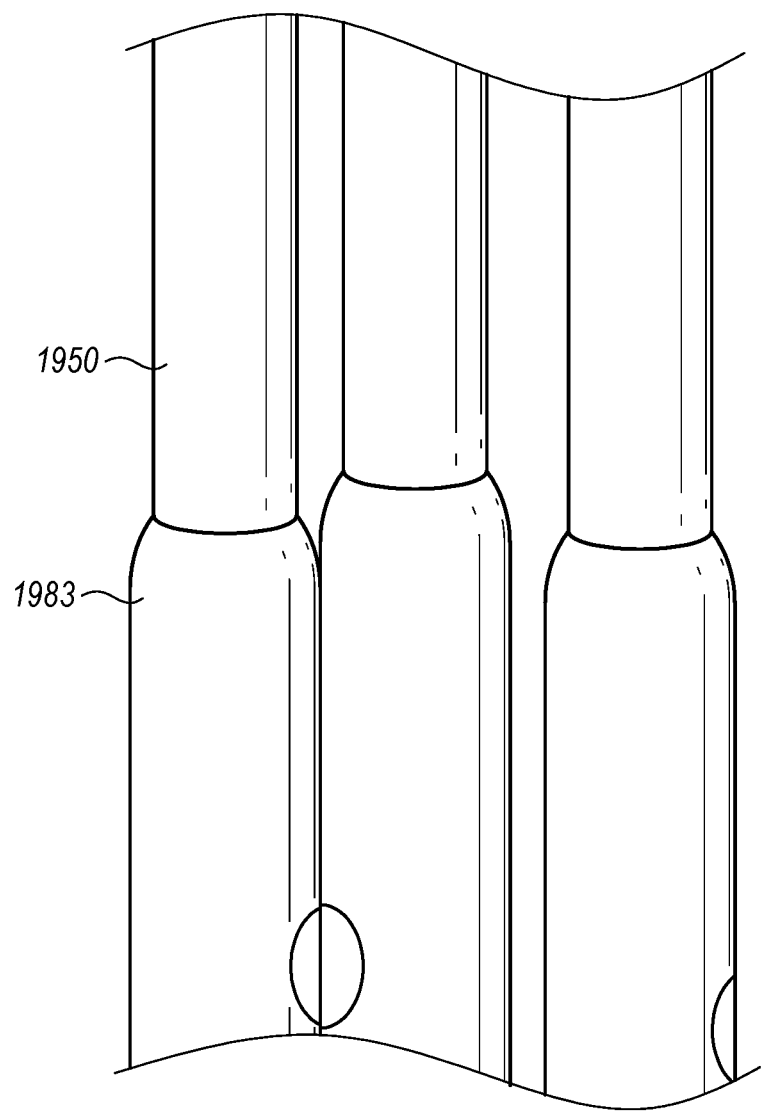

FIGS. 18 and 19 depict a solid needle proximal end (1850) for use with dual chamber safe injection systems according to some embodiments. Using a solid proximal end simplifies manufacturing and reduces the cost thereof. The needle proximal end (1850) is formed from a shoulder solid metal stem and a longer needle joining member (1883). This eliminates the need to drill side holes in the hollow stem, and also eliminates a need for the plug at the point end. The solid needle proximal end (1850) design uses a longer needle joining member (1883) with proximal openings (1885) near the proximal end (1884) to provide a liquid passage between the chambers. The weld between the needle joining member (1883) and the solid needle proximal end (1850) is smooth and rounded to have minimal resistance to the passage of the detent (1812) (see FIG. 19). A wide groove (1822) is formed on the needle joining member (1883) to catch the detent (1812) and hold the distal stopper member in the correct position for liquid transfer into transfer configuration.

Threaded Plunger Member

While dual chamber safe injection systems are known, users must exercise extreme care when applying a distally directed force on the plunger member to move the proximal stopper member distally to transfer fluid from the proximal chamber to the distal chamber. Applying either too much or too little distally directed force on the plunger member can result in incomplete fluid transfer from the proximal chamber to the distal chamber. Applying too much force on the plunger member can move the distal stopper member too far distally, thereby occluding the fluid transfer openings and rendering the system unusable. Applying too little force on the plunger member can result in incomplete fluid transfer until more force is applied, which may move the distal stopper member too far distally and occlude the fluid transfer openings. The threaded plunger member embodiments described herein address the problems described above. Addressing these problems renders dual chamber safe injection systems more user-friendly for accurate and safe mixed injectables delivery.

Figure 20:
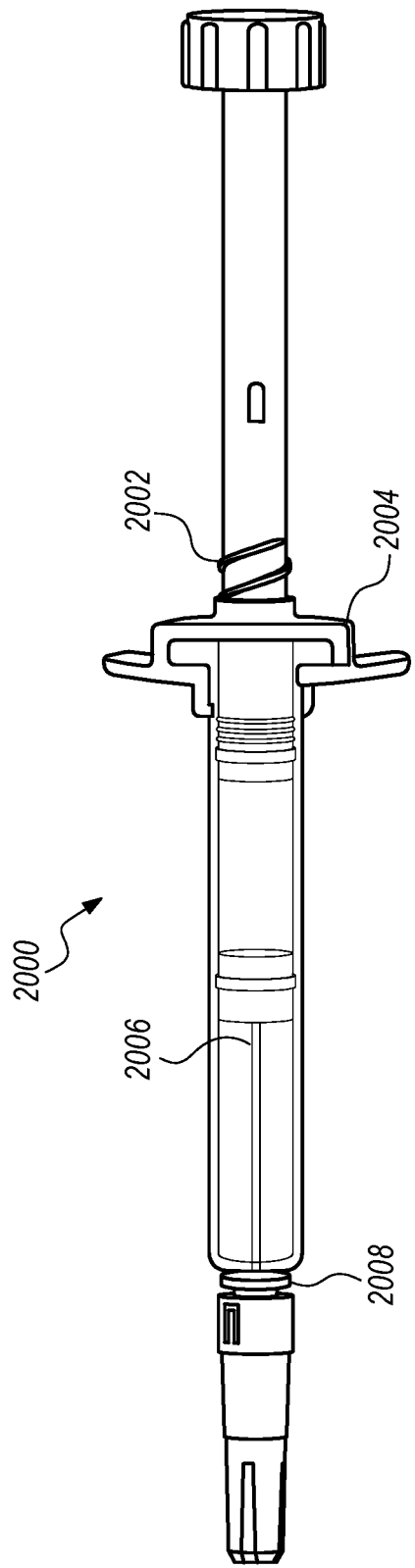
FIGS. 20 and 21 depict a dual chamber safe injection system with a shielded and vented needle cover in sealed and vented configurations, respectively according to some embodiments.

FIG. 20 depicts a dual chamber safe injection system (2000) according to some embodiments. The system (2000) includes a threaded plunger member (2002), a threaded figure flange (2004), a slotted needle proximal opening (2006), and a two position shielded and vented needle cover (2008). The system (2000) depicted in FIG. 20 is in a transport configuration before use. In the transport configuration, the shielded and vented needle cover (2008) is in its sealed configuration (described below).

Figure 21:
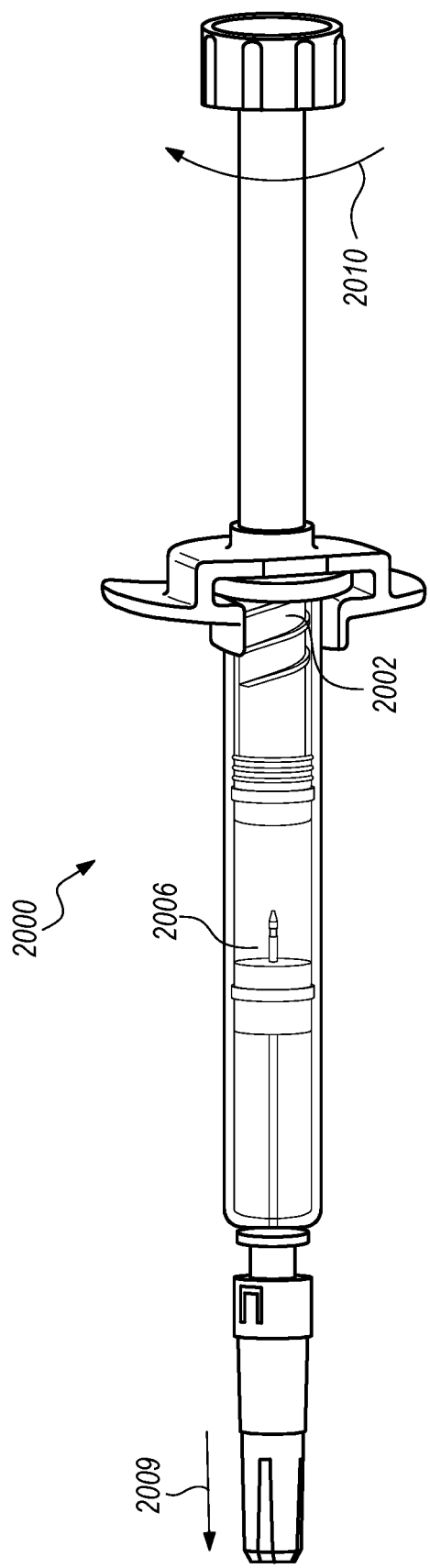

FIG. 21 depicts the dual chamber safe injection system (2000) depicted in FIG. 20 in a fluid transfer configuration. In the fluid transfer configuration, the shielded and vented needle cover (2008) has been pulled distally (2009) on the needle hub to move the shielded and vented needle cover (2008) into its vented configuration (described below). Next, the plunger member (2002) is rotated in a clockwise direction (2010) relative to the syringe body to controllably move the plunger member (2002) and the proximal and distal stopper members distally relative to the syringe body (via threaded interaction with the finger flange (2004). Moving the distal stopper member distally a controlled amount allows the proximal end of the needle to pierce the distal stopper member. This places the proximal needle opening in the proximal chamber, thereby allowing fluid transfer from the proximal chamber to the distal chamber for mixing with the injectable contained in the distal chamber.

Figure 22:
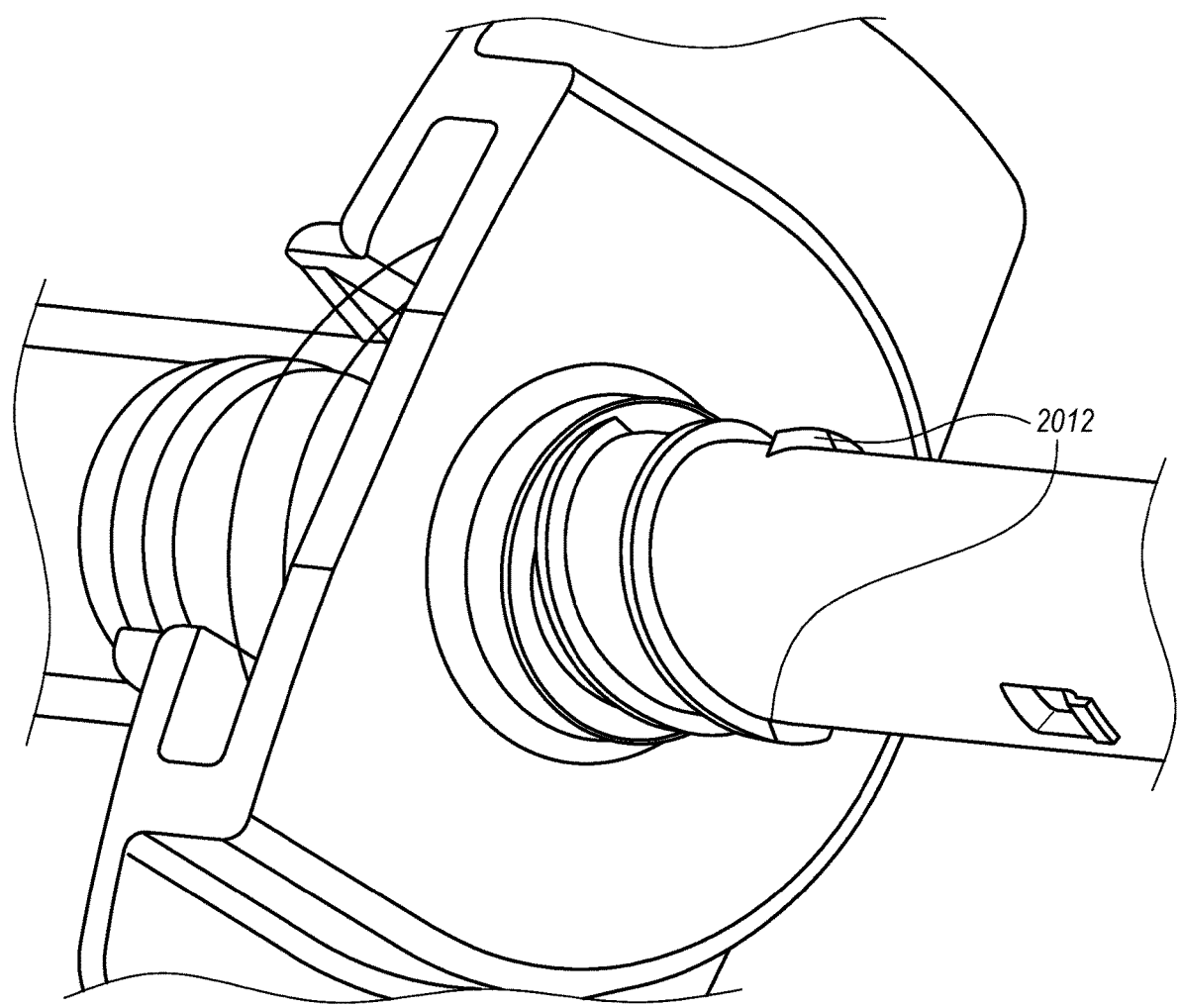
FIG. 22 depicts in detail a threaded plunger member and a finger flange for use with a dual chamber safe injection system according to some embodiments.

FIG. 22 depicts in detail the threaded plunger member (2002) and the finger flange (2004) of the dual chamber safe injection system (2000) depicted in FIG. 20. The threads (2012) on the threaded plunger member (2002) have a relatively large helical thread pitch for a greater amount of axial plunger member (2002) movement per revolution of the plunger member (2002). The thread pitch may be between 5 mm and 25 mm. Preferably, the thread pitch is 8.5 mm. The threads (2012) may form a single helix, or a multi-start helix. The multi-start helix may be: a double helix, a triple helix, a quad helix, etc. Preferably, the threads (2012) are a double helix.

Figure 23:
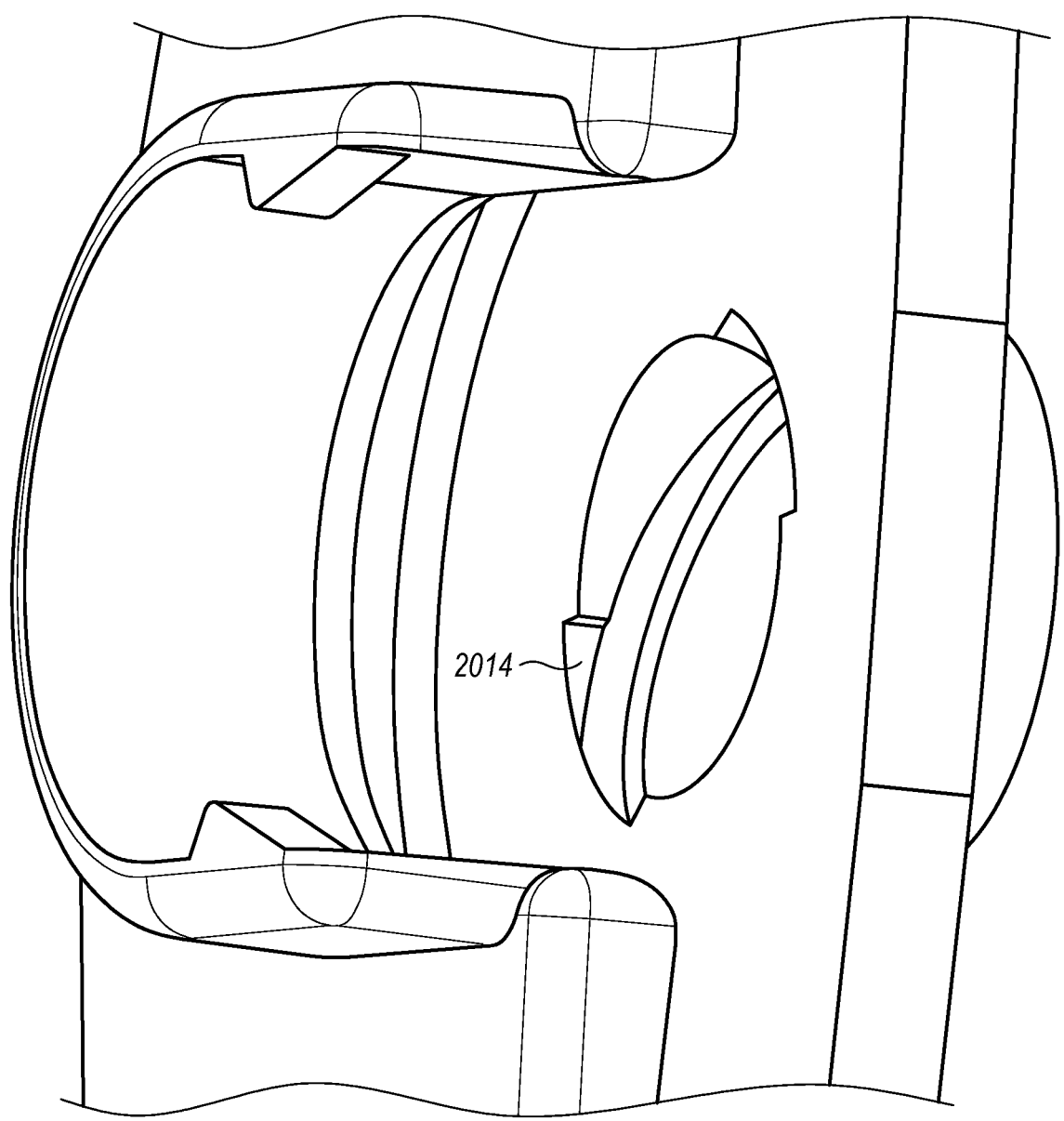
FIG. 23 depicts a finger flange for use with a dual chamber safe injection system according to some embodiments.

FIG. 23 depicts in detail the finger flange (2004) and the threads therein that correspond to the threads (2012) on the plunger member (2002) (see FIG. 22). One wall (2014) of the thread groove in the finger flange (2004) is removed to facilitate the transition between rotation of the plunger member (2002) to punch the proximal end of the needle through the distal stopper member and/or transfer fluid from the proximal chamber to the distal chamber and application of distally directed force to the plunger member (2002) to complete fluid transfer and/or eject/inject the mixed fluid from the distal chamber.

Figure 24:
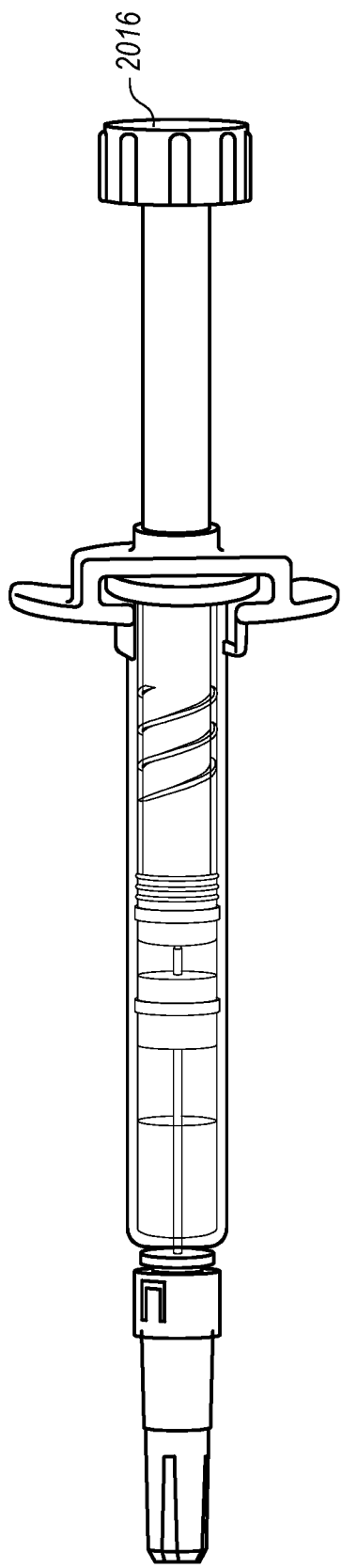
FIG. 24 depicts a dual chamber safe injection system with a shielded and vented needle cover with the system in a transfer configuration according to some embodiments.

FIG. 24 depicts the dual chamber safe injection system (2000) depicted in FIG. 20 in a later stage of the fluid transfer configuration compared to FIG. 34. Because there is still space between the proximal and distal stoppers (and therefore still fluid in the proximal chamber) fluid transfer is still incomplete in the embodiment depicted in FIG. 24. However, the threaded surface of the plunger member (2002) is well distal of the finger flange (2004). Therefore, in this embodiment, rotation of the plunger member only accomplishes penetration of the proximal end of the needle through the distal stopper. Distally directed force (2016) must still be applied to the plunger member (2002) to complete fluid transfer. In other embodiments, the threaded surface on the plunger member (2002) such that rotation of the plunger member (2002) can complete fluid transfer.

Figure 25:
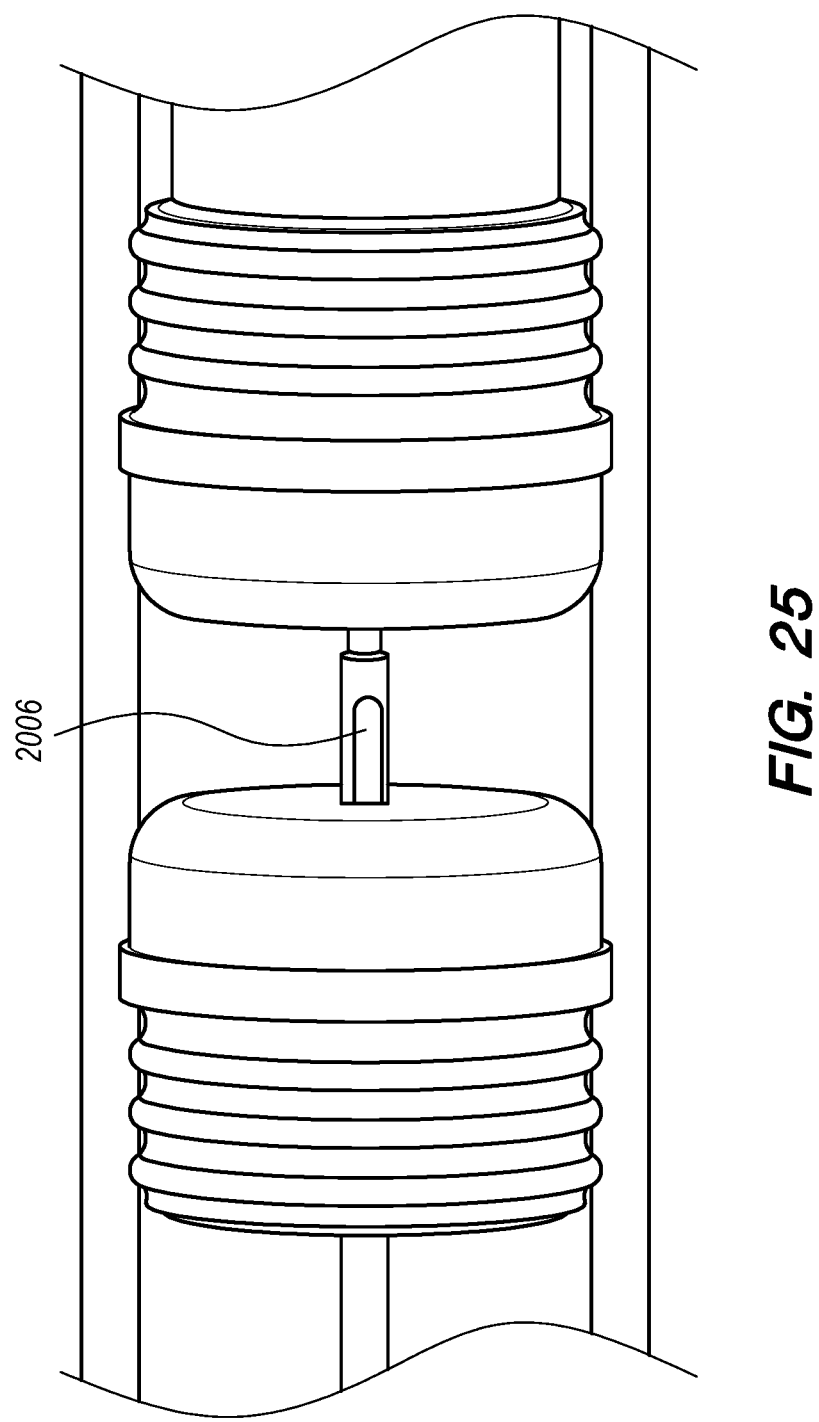
FIG. 25 depicts in detail the proximal and distal stopper members and a proximal opening of a needle for use with a dual chamber safe injection system according to some embodiments.

FIG. 25 depicts in detail the proximal opening (2006) in the needle of the dual chamber safe injection system (2000) depicted in FIG. 20. The proximal opening (2006) is a slot which maintains an open fluid path between the proximal and distal chambers even as the proximal and distal stopper members approach each other and touch to end fluid transfer.

Figure 26:
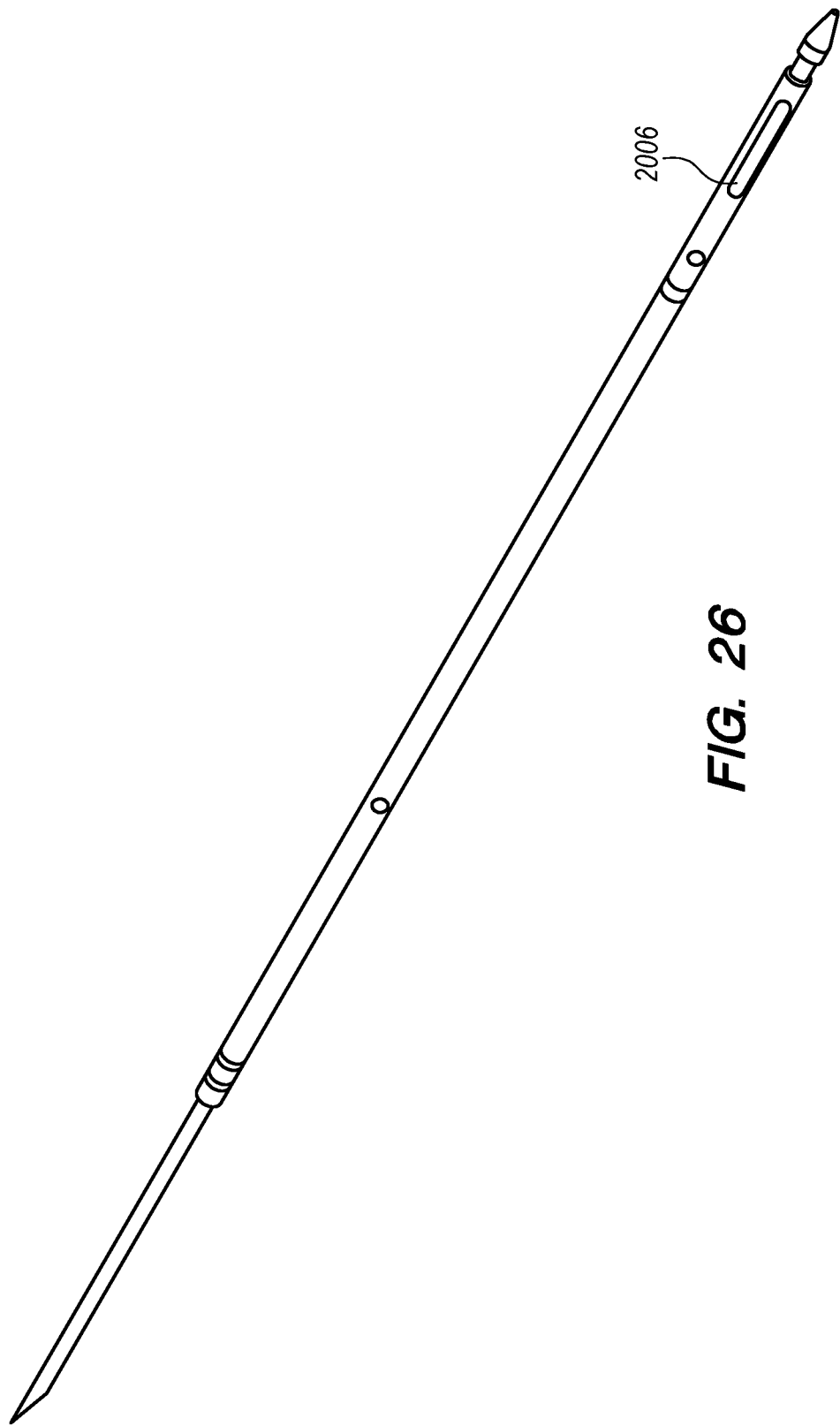
FIG. 26 depicts a needle for use with a dual chamber safe injection system according to some embodiments.

FIG. 26 depicts in detail the needle of the dual chamber safe injection system (2000) depicted in FIG. 20. The slotted proximal opening (2006) can be seen in FIG. 26.

Figure 27:
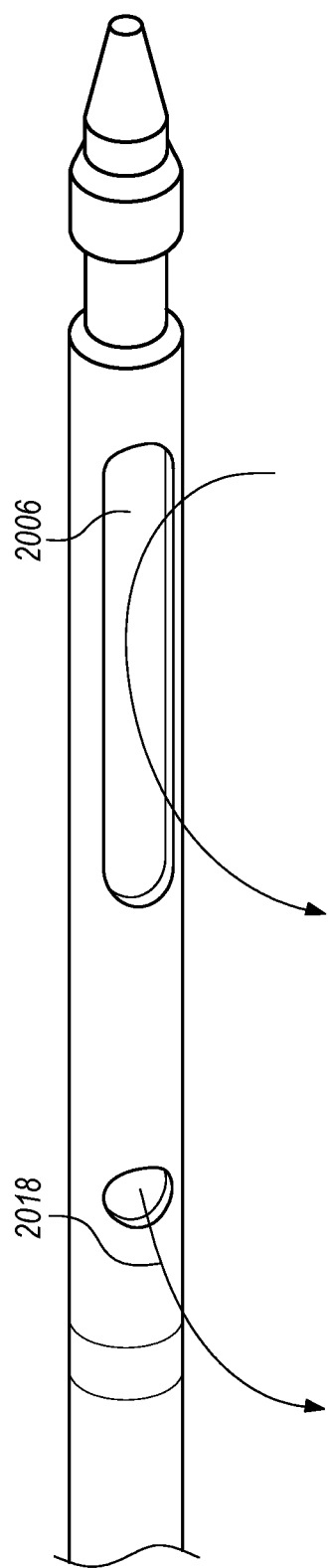
FIG. 27 depicts in detail the proximal end of a needle for use with a dual chamber safe injection system according to some embodiments.

FIG. 27 depicts in greater detail the proximal end of the needle of the dual chamber safe injection system (2000) depicted in FIG. 20. The slotted proximal opening (2006) and the middle opening (2018) can both be seen in FIG. 27. The size of the slotted proximal opening (2006) prevents excessive pressure from building up in the proximal chamber that may otherwise prematurely move the distal stopper member distally. In fact, with a sufficiently long slotted proximal opening (2006), the proximal and distal ends of the slotted proximal opening (2006) may form a fluid path around the proximal stopper member in addition to the fluid path including the middle opening (2018). Alternatively or additionally, the middle opening (2018) may also be a slot.

Figure 28:
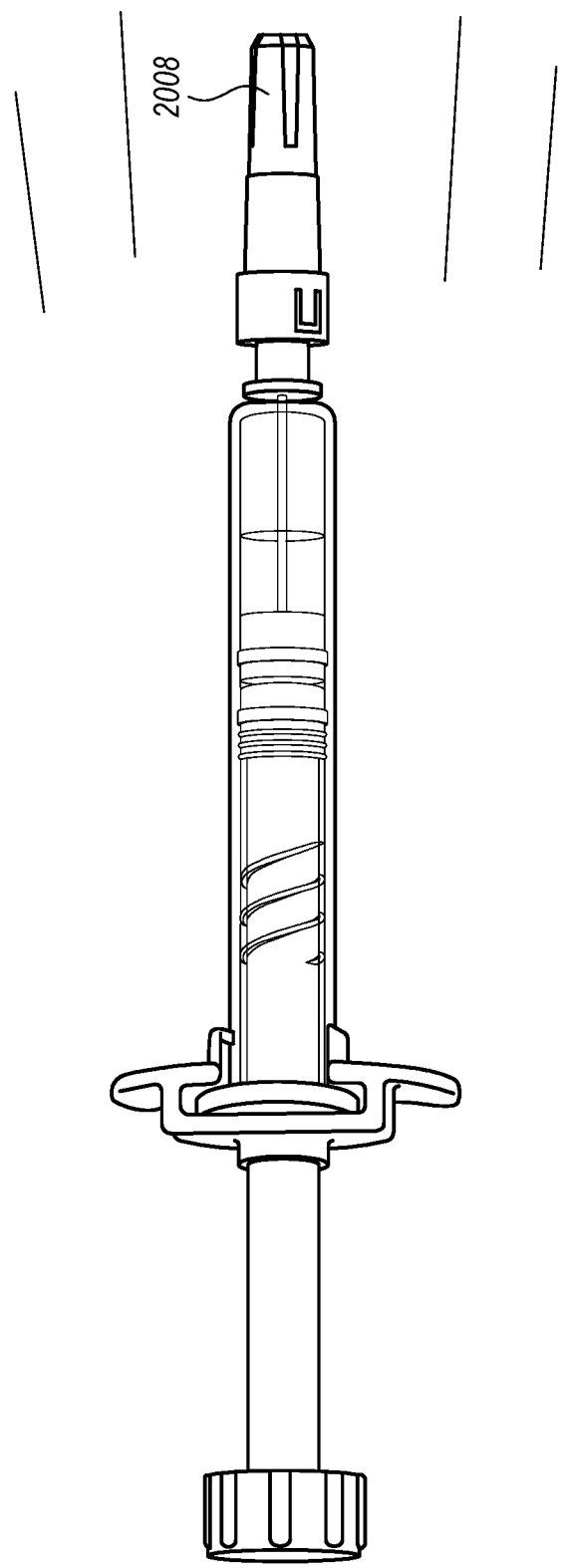
FIG. 28 depicts a dual chamber safe injection system with a shielded and vented needle cover in the vented configuration and with the system in a mixed configuration according to some embodiments.

FIG. 28 depicts the dual chamber safe injection system (2000) depicted in FIG. 20 in a mixed configuration. The proximal and distal stopper members have together thereby terminating fluid transfer. With the fluid from the proximal chamber transferred to the distal chamber, the system (2000) can be agitated (e.g., by shaking) to mix the injectables in the distal chamber. Having a shielded and vented needle cover (2008) protects the needle and the user during mixing agitation.

Figure 29:
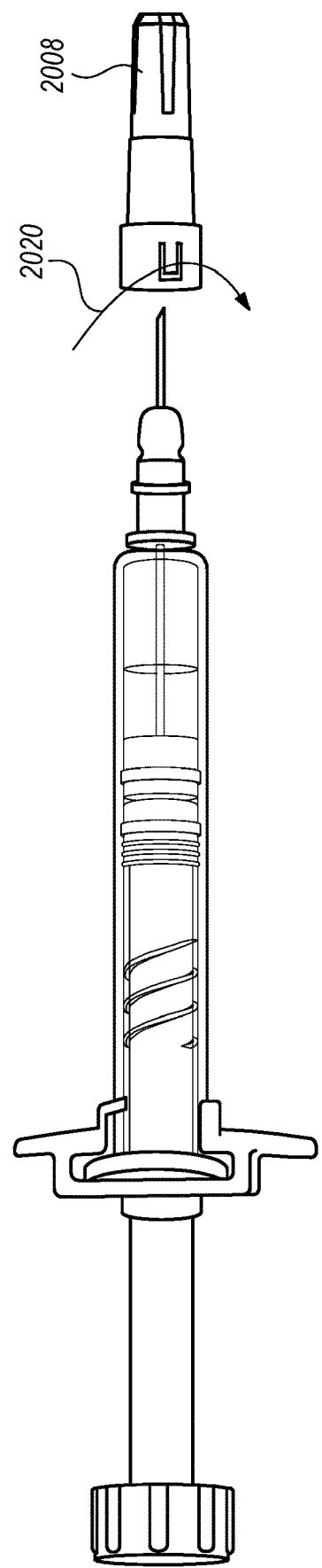
FIG. 29 depicts a dual chamber safe injection system with a shielded and vented needle cover removed for injection and with the system in a mixed configuration according to some embodiments.

FIG. 29 depicts removal of the needle cover (2008) by unscrewing (2020). To prepare the dual chamber safe injection system (2000) for injection.

Shielded and Vented Needle Cover

With a pre-attached needle, without vented needle covers, transferring fluid from the proximal chamber to the distal chamber can result in pressure builds up in the distal chamber. Increased pressure in the distal chamber can cause retrograde flow from the distal chamber to the proximal chamber, which may lead to an incorrect ratio of the injectables in the proximal and distal chambers after mixing. Again the user must be careful to overcome pressure builds up in the distal chamber by applying a constant distally directed force on the plunger member. Even if the user applies such a force, when the needle cover is eventually removed, the increased pressure in the distal chamber may prematurely eject some of the mixed injectable. The shielded and vented needle cover embodiments described herein address the problems described above. Addressing these problems also renders dual chamber safe injection systems more user-friendly for accurate and safe mixed injectables delivery.

Figure 30:
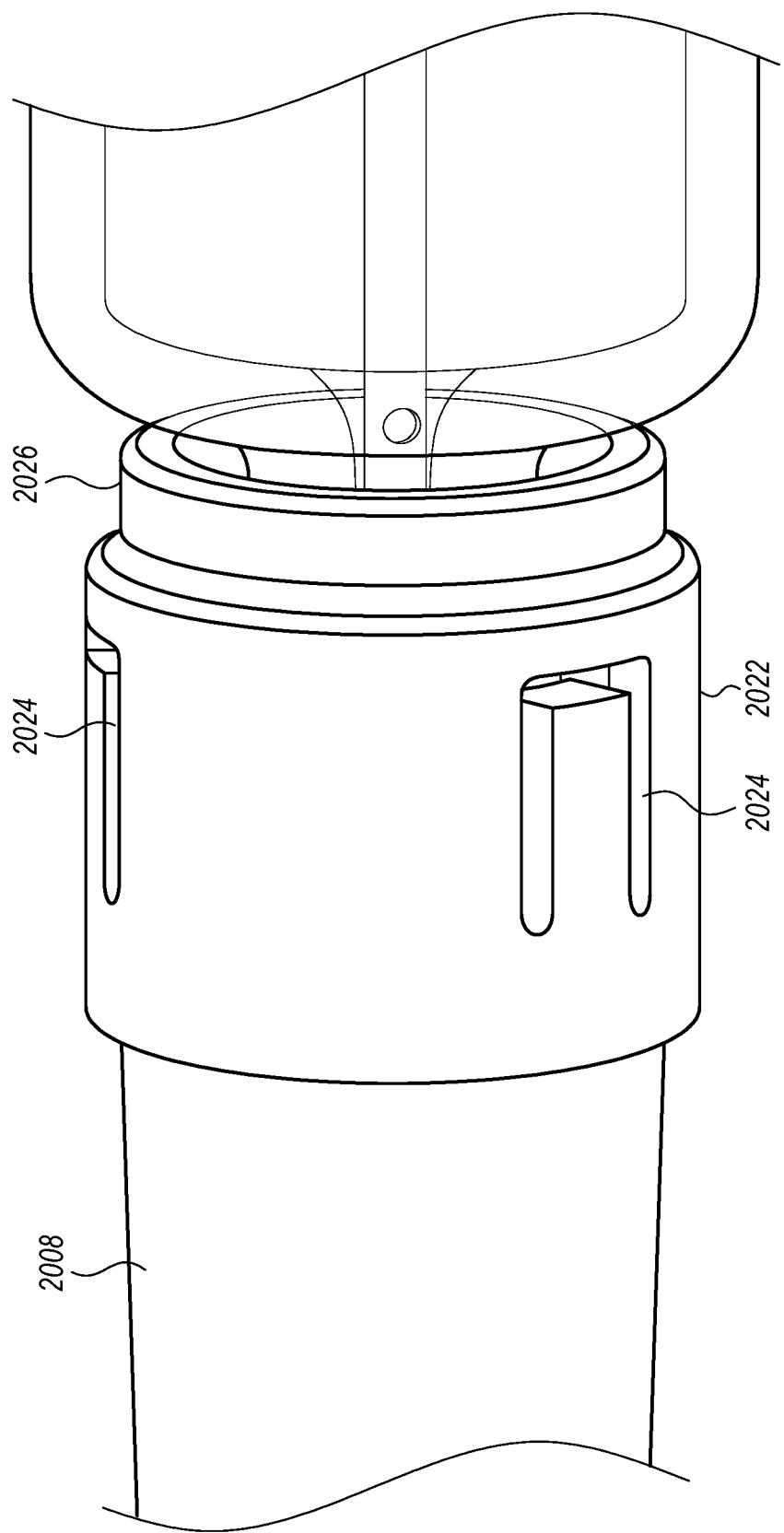
FIG. 30 depicts in detail the proximal end of a shielded and vented needle cover in a sealed configuration for use with a dual chamber safe injection system according to some embodiments.

FIG. 30 depicts a shielded and vented needle cover (2008) for use with the dual chamber safe injection system (2000) depicted in FIG. 20 is a sealed configuration. The needle cover (2008) includes an adapter (2022) having a plurality (e.g., three) of flexible fingers (2024). FIG. 30 also depicts the hub (2026) of the needle assembly on the syringe, which interacts with various components of the needle cover (2008) as described below.

Figure 31:
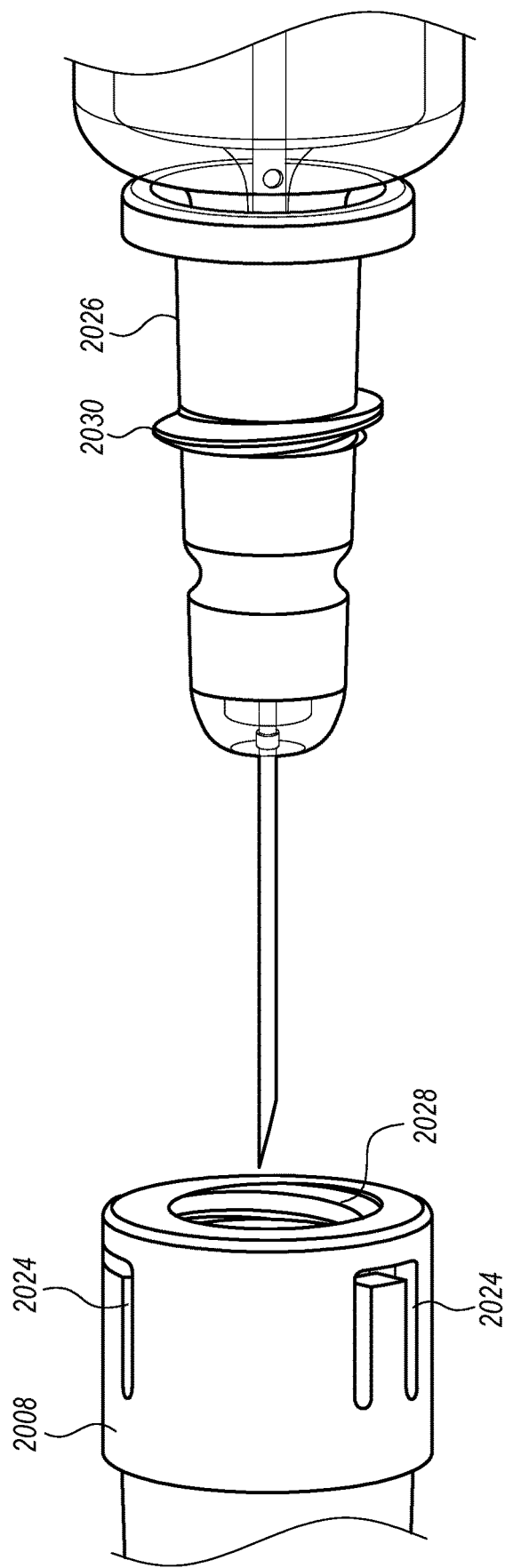
FIG. 31 depicts in detail the proximal end of a shielded and vented needle cover removed from the distal end of a needle hub and for use with a dual chamber safe injection system according to some embodiments.

FIG. 31 depicts the shielded and vented needle cover (2008) depicted in FIG. 30 removed from the hub (2026) to show various components of the needle cover (2008) and the hub (2026). The needle cover (2008) includes a plurality of flexible fingers (2024) and a threaded interior surface (2028). The hub (2026) includes a threaded exterior surface (2030) corresponding to and configured to interact with the threaded interior surface (2028) on the needle cover (2008).

Figure 32:
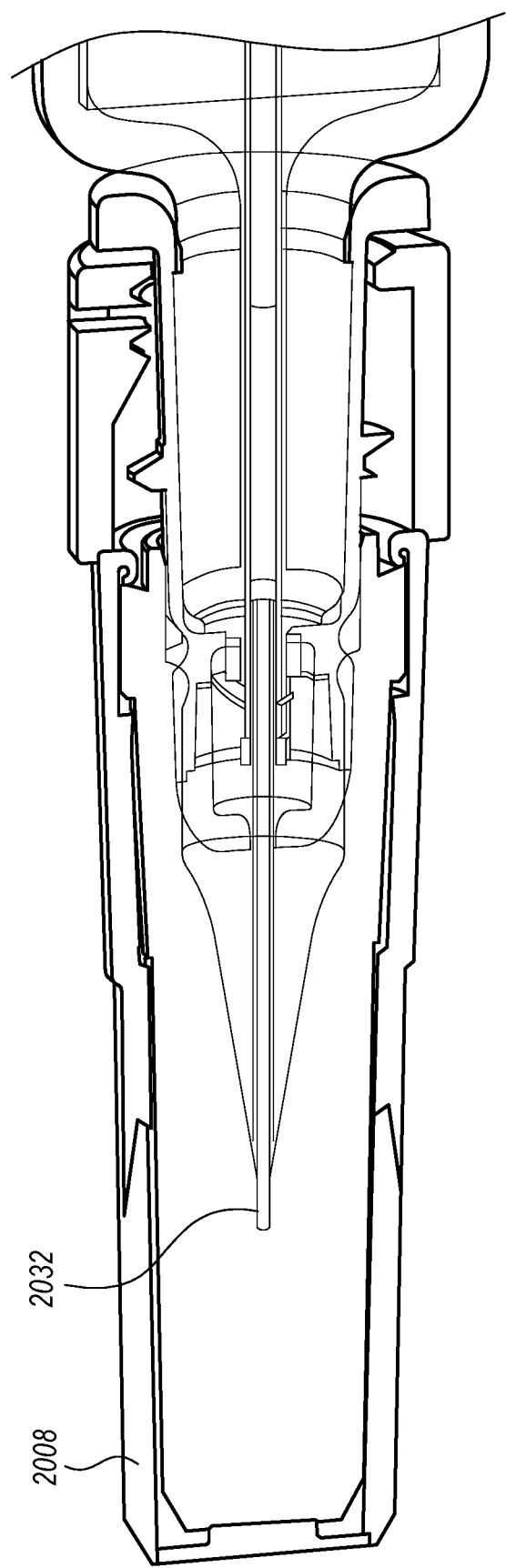
FIG. 32 depicts in cross-sectional detail the proximal end of a shielded and vented needle cover in a sealed configuration for use with a dual chamber safe injection system according to some embodiments.

FIG. 32 depicts in cross-section the shielded and vented needle cover (2008) depicted in FIG. 30 in the sealed configuration. In the sealed configuration, a distal end (2032) of the needle is occluded by an inner material of the needle cover (2008).

Figure 33:
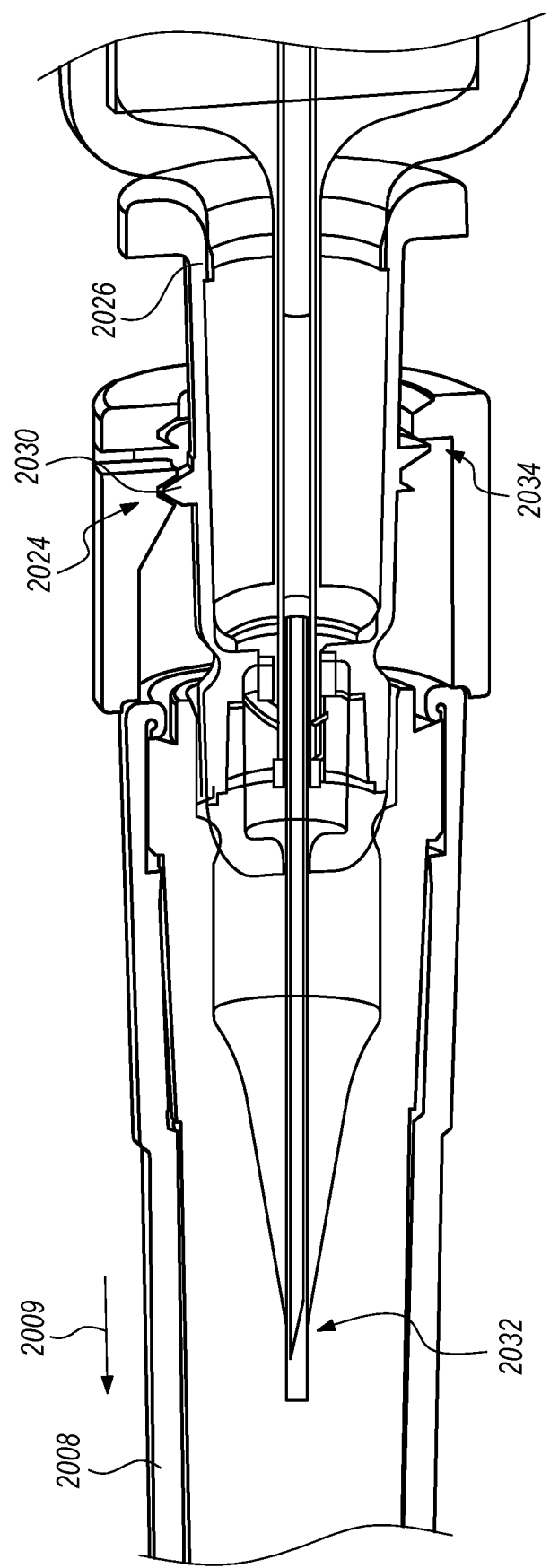
FIG. 33 depicts in cross-sectional detail the proximal end of a shielded and vented needle cover in a vented configuration for use with a dual chamber safe injection system according to some embodiments.

FIG. 33 depicts in cross-section the shielded and vented needle cover (2008) depicted in FIG. 32 in the shielded and vented configuration. As described above, the needle cover (2008) is moved from the sealed configuration to the vented configuration by pulling distally (2009) on the needle cover (2008). Moving the needle cover (2008) distally on the hub (2026) moves the flexible fingers (2024) into engagement with the threaded exterior surface (2030) of the hub (2026). The needle cover (2008) also includes a proximal flange (2034). The interaction between the flexible fingers (2024), the proximal flange (2034), and the threaded exterior surface (2030) prevent further distal pulling (or pushing) of the needle cover (2008) along a longitudinal axis of the system (2000). This locks the needle cover (2008) in the vented configuration where the distal end of the needle (2032) is not occluded and fluid (i.e., gas) is allowed to exit from the needle distal end (2032) and can flow out of the needle cover (2008). In this configuration, the needle remains covered or shielded from the user, while the vented needle cover (2008) allows the pressure in the distal chamber to be reduced by venting fluid (i.e. gas) out of the distal chamber. Shielding the needle covers the sharp needle tip to prevent needle stick injury to the user during mixing and shaking of the dual chamber syringe. After mixing, the needle cover (2008) may be removed from the hub (2026) by rotating (2020) the needle cover (2008) relative to the hub (2026), as shown in FIG. 29.

Figure 34:
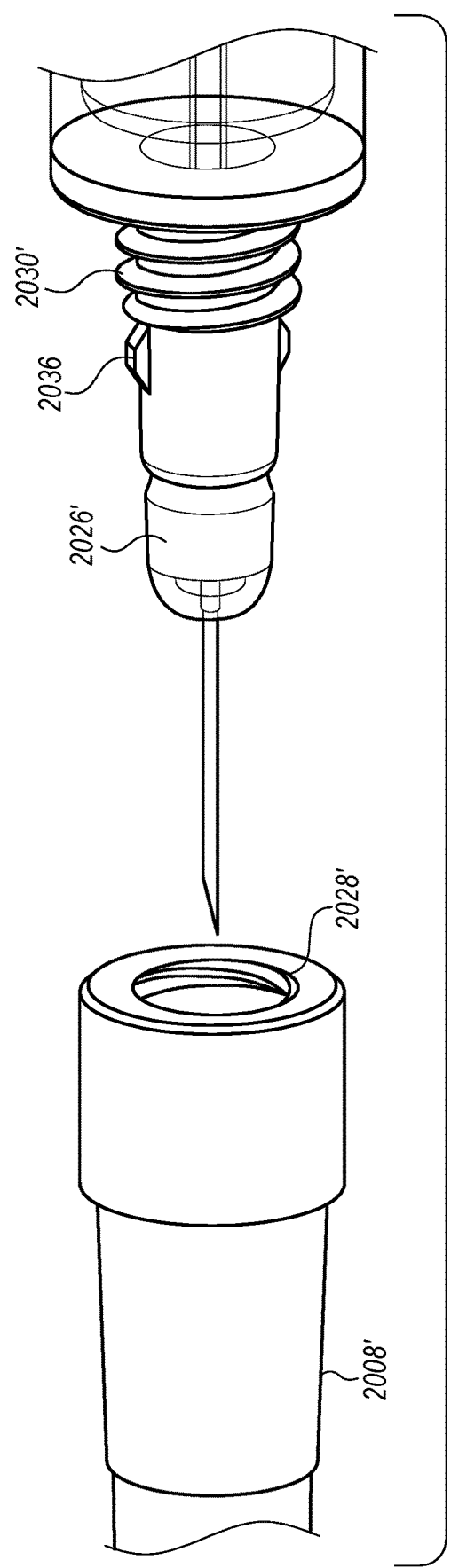
FIG. 34 depicts in detail the proximal end of a shielded and vented needle cover removed from the distal end of a needle hub and for use with a dual chamber safe injection system according to some embodiments.

FIG. 34 depicts a shielded and vented needle cover (2008') and a hub (2026') according to other embodiments. The needle cover (2008') has threaded interior surface (2028'). The hub (2026') includes a threaded exterior surface (2030') corresponding to and configured to interact with the threaded interior surface (2028') on the needle cover (2008'). The needle cover (2008') and the hub (2026') are configured such that rotating the needle cover (2008') relative to the hub (2026') moves the needle cover from the sealed configuration to the vented configuration. The hub (2026') also includes an interference member (2036) that forms a connection between the needle cover (2008') and the hub (2026') in the vented configuration. However, the interference fit between the interference member (2036) and the needle cover (2008') can be overcome to remove the needle cover (2008') from the hub (2026').

While the prefilled dual chamber safety injection systems depicted and described herein include syringes with staked needles, the various configurations/embodiments described herein (e.g., serial injection, detent dual chamber, threaded plunger member, and shielded and vented needle cover) can be used with cartridges an auto injector, and injection systems with Luer connectors, transfer pipes, and no needles such as those described in U.S. Utility patent application Ser. Nos. 15/801,281 and 15/801,259, which were previously incorporated by reference herein.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, PTFE, ETFE, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A system for serially injecting liquids, comprising:
   a syringe body defining a syringe proximal opening and a distal interface at a distal end of the syringe body;
   a proximal stopper member and a distal stopper member disposed in the syringe body, forming a proximal chamber between the proximal stopper member and the distal stopper member and a distal chamber between the distal stopper member and the distal end of the syringe body;
   a first liquid in the distal chamber;
   a second liquid in the proximal chamber;
   a plunger member configured to be manually manipulated to insert the proximal stopper member distally relative to the syringe body; and
   a hub assembly coupled to the distal interface of the syringe body, the hub assembly including
      a transfer pipe having a transfer pipe proximal end and a transfer pipe distal end,
      a hub, and
      a connector fluidly coupled to the transfer pipe distal end,
   wherein manipulating the plunger member to insert the proximal stopper member distally relative to the syringe body initially expels the first liquid from the distal chamber through the transfer pipe, then serially expels the second liquid from the proximal chamber through the transfer pipe,
   wherein the transfer pipe defines a transfer pipe interior, a distal end opening at the transfer pipe distal end, a middle opening, and a proximal opening, wherein the distal end opening, the middle opening, and the proximal opening are fluidly coupled through the transfer pipe interior, and
   wherein a distance between the proximal opening and the distal end of the syringe body is substantially equal to a length of the distal stopper member, such that when the distal stopper member is inserted to the distal end of the syringe body, the proximal stopper member is inserted distally relative to the transfer pipe to position the proximal opening in the proximal chamber.

2. The system of claim 1, wherein first and second sizes of the respective distal and proximal chambers can be modified by movement of the proximal and distal stopper members relative to the syringe body.

3. The system of claim 1, wherein the proximal and distal stopper members and the syringe body are configured such that distally directed force applied to the proximal stopper member is transmitted through the second liquid to the distal stopper member until the proximal stopper member is inserted distally relative to the transfer pipe to position the proximal opening in the proximal chamber.

4. The system of claim 1, wherein the proximal stopper member comprises a first polymer coating on a distal surface of the proximal stopper member, and
   wherein the distal stopper member comprises a second polymer coating on a proximal surface of the distal stopper member, such that the proximal chamber is defined by the syringe body and the first and second polymer coatings.

5. The system of claim 1, the distal stopper member having
   a funnel that tapers in a proximal direction, and
   a space disposed at a tapered proximal end of the funnel.

6. The system of claim 5, wherein the funnel is configured to guide the transfer pipe proximal end into the space at the tapered proximal end of the funnel, to thereby align the transfer pipe with the distal stopper member.

7. The system of claim 6, wherein the funnel is configured to align the transfer pipe with the distal stopper member during assembly of the system.

8. The system of claim 6, wherein the funnel is configured to align the transfer pipe with the distal stopper member during manipulation of the plunger member to insert the proximal stopper member distally relative to the syringe body.

9. The system of claim 1, the distal stopper member having a detent to resist passage of the transfer pipe proximal end through the distal stopper member.

10. The system of claim 9, the detent having a "U" shape.

11. The system of claim 9, the detent having a flattened cross-section.

12. The system of claim 9, the detent having a transfer pipe proximal end receiving feature.

13. The system of claim 12, the transfer pipe proximal end receiving feature having a beveled surface.

14. The system of claim 9, the transfer pipe having a shoulder to resist passage of the transfer pipe through the detent.

15. The system of claim 14, the shoulder and the detent configured such that a resistance to the shoulder passing through the detent is overcome by about 2 lbs. to about 5 lbs. of distally directed force applied to the plunger member.

16. The system of claim 15, wherein the detent is modifiable to modulate the distally directed force required to overcome the resistance.

17. The system of claim 14, the shoulder comprising an angle of about 50 degrees.

18. The system of claim 9, the transfer pipe having a groove to resist passage of the transfer pipe through the detent.

19. The system of claim 18, the groove and the detent configured such that a resistance to the groove passing through the detent is overcome by about 2 lbs. to about 5 lbs. of distally directed force applied to the plunger member.

20. The system of claim 19, wherein the detent is modifiable to modulate the distally directed force required to overcome the resistance.

21. A system for serially injecting liquids, comprising:
a syringe body defining a syringe proximal opening and a distal interface at a distal end of the syringe body;
a proximal stopper member and a distal stopper member disposed in the syringe body, forming a proximal chamber between the proximal stopper member and the distal stopper member and a distal chamber between the distal stopper member and the distal end of the syringe body;
a first liquid in the distal chamber;
a second liquid in the proximal chamber;
a plunger member configured to be manually manipulated to insert the proximal stopper member distally relative to the syringe body; and
a hub assembly coupled to the distal interface of the syringe body, the hub assembly including
a transfer pipe having a transfer pipe proximal end and a transfer pipe distal end,
a hub, and
a connector fluidly coupled to the transfer pipe distal end,
wherein manipulating the plunger member to insert the proximal stopper member distally relative to the syringe body initially expels the first liquid from the distal chamber through the transfer pipe, then serially expels the second liquid from the proximal chamber through the transfer pipe,
wherein the transfer pipe defines a transfer pipe interior, a distal end opening at the transfer pipe distal end, a middle opening, and a proximal opening, wherein the distal end opening, the middle opening, and the proximal opening are fluidly coupled through the transfer pipe interior,
wherein the system has
a first injection configuration wherein the proximal opening is disposed in the distal chamber, and
a second injection configuration wherein the proximal opening is disposed in the proximal chamber, thereby allowing transfer of the second liquid from the proximal chamber, through the proximal opening and the transfer pipe interior, and out the distal end opening,
wherein the distal stopper member obstructs the middle opening when the system is in the second injection configuration.

22. A system for serially injecting liquids, comprising:
a syringe body defining a syringe proximal opening and a distal interface at a distal end of the syringe body;
a proximal stopper member and a distal stopper member disposed in the syringe body, forming a proximal chamber between the proximal stopper member and the distal stopper member and a distal chamber between the distal stopper member and the distal end of the syringe body;
a first liquid in the distal chamber;
a second liquid in the proximal chamber;
a plunger member configured to be manually manipulated to insert the proximal stopper member distally relative to the syringe body; and
a hub assembly coupled to the distal interface of the syringe body, the hub assembly including
a transfer pipe having a transfer pipe proximal end and a transfer pipe distal end,
a hub, and
a connector fluidly coupled to the transfer pipe distal end,
wherein manipulating the plunger member to insert the proximal stopper member distally relative to the syringe body initially expels the first liquid from the distal chamber through the transfer pipe, then serially expels the second liquid from the proximal chamber through the transfer pipe,
wherein the distal stopper member has a detent to resist passage of the transfer pipe proximal end through the distal stopper member, and
wherein the detent is configured such that a resistance to the transfer pipe proximal end passing through the detent is overcome by about 2 lbs. to about 5 lbs. of distally directed force applied to the plunger member.

23. The system of claim 22, wherein the detent is modifiable to modulate the distally directed force required to overcome the resistance.

24. A system for serially injecting liquids, comprising:
a syringe body defining a syringe proximal opening and a distal interface at a distal end of the syringe body;
a proximal stopper member and a distal stopper member disposed in the syringe body, forming a proximal chamber between the proximal stopper member and the distal stopper member and a distal chamber between the distal stopper member and the distal end of the syringe body;
a first liquid in the distal chamber;
a second liquid in the proximal chamber;
a plunger member configured to be manually manipulated to insert the proximal stopper member distally relative to the syringe body; and
a hub assembly coupled to the distal interface of the syringe body, the hub assembly including
a transfer pipe having a transfer pipe proximal end and a transfer pipe distal end,
a hub, and
a connector fluidly coupled to the transfer pipe distal end,
wherein manipulating the plunger member to insert the proximal stopper member distally relative to the syringe body initially expels the first liquid from the distal chamber through the transfer pipe, then serially expels the second liquid from the proximal chamber through the transfer pipe,
wherein the distal stopper member has a detent to resist passage of the transfer pipe proximal end through the distal stopper member, and
wherein the detent comprises a bent wire.

25. A system for serially injecting liquids, comprising:
a syringe body defining a syringe proximal opening and a distal interface at a distal end of the syringe body;
a proximal stopper member and a distal stopper member disposed in the syringe body, forming a proximal chamber between the proximal stopper member and the distal stopper member and a distal chamber between the distal stopper member and the distal end of the syringe body;
a first liquid in the distal chamber;
a second liquid in the proximal chamber;
a plunger member configured to be manually manipulated to insert the proximal stopper member distally relative to the syringe body; and
a hub assembly coupled to the distal interface of the syringe body, the hub assembly including
 a transfer pipe having a transfer pipe proximal end and a transfer pipe distal end,
 a hub, and
 a connector fluidly coupled to the transfer pipe distal end,
wherein manipulating the plunger member to insert the proximal stopper member distally relative to the syringe body initially expels the first liquid from the distal chamber through the transfer pipe, then serially expels the second liquid from the proximal chamber through the transfer pipe,
wherein the distal stopper member has a detent to resist passage of the transfer pipe proximal end through the distal stopper member, and
wherein the detent comprises an annealed stainless alloy.

26. A system for serially injecting liquids, comprising:
a syringe body defining a syringe proximal opening and a distal interface at a distal end of the syringe body;
a proximal stopper member and a distal stopper member disposed in the syringe body, forming a proximal chamber between the proximal stopper member and the distal stopper member and a distal chamber between the distal stopper member and the distal end of the syringe body;
a first liquid in the distal chamber;
a second liquid in the proximal chamber;
a plunger member configured to be manually manipulated to insert the proximal stopper member distally relative to the syringe body; and
a hub assembly coupled to the distal interface of the syringe body, the hub assembly including
 a transfer pipe having a transfer pipe proximal end and a transfer pipe distal end,
 a hub, and
 a connector fluidly coupled to the transfer pipe distal end,
wherein manipulating the plunger member to insert the proximal stopper member distally relative to the syringe body initially expels the first liquid from the distal chamber through the transfer pipe, then serially expels the second liquid from the proximal chamber through the transfer pipe,
wherein the distal stopper member has a detent to resist passage of the transfer pipe proximal end through the distal stopper member, and
wherein the transfer pipe proximal end comprises a transfer pipe proximal end feature having an angle of about 30 degrees.

* * * * *